(12) United States Patent
Arnold et al.

(10) Patent No.: US 8,603,949 B2
(45) Date of Patent: Dec. 10, 2013

(54) LIBRARIES OF OPTIMIZED CYTOCHROME P450 ENZYMES AND THE OPTIMIZED P450 ENZYMES

(75) Inventors: Frances H. Arnold, La Cañada, CA (US); Christopher R. Otey, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 2297 days.

(21) Appl. No.: 10/869,813

(22) Filed: Jun. 15, 2004

(65) Prior Publication Data

US 2005/0059045 A1    Mar. 17, 2005

Related U.S. Application Data

(60) Provisional application No. 60/479,005, filed on Jun. 17, 2003.

(51) Int. Cl.
*C40B 50/02* (2006.01)

(52) U.S. Cl.
USPC ............... 506/24; 506/18; 530/401; 435/189

(58) Field of Classification Search
None
See application file for complete search history.

(56) References Cited

U.S. PATENT DOCUMENTS

| | | |
|---|---|---|
| 5,605,793 A | 2/1997 | Stemmer |
| 5,733,907 A | 3/1998 | Alexander et al. |
| 5,741,691 A | 4/1998 | Arnold et al. |
| 5,811,238 A | 9/1998 | Stemmer et al. |
| 5,830,721 A | 11/1998 | Stemmer et al. |
| 5,906,930 A | 5/1999 | Arnold et al. |
| 5,942,423 A | 8/1999 | Demain et al. |
| 5,945,325 A | 8/1999 | Arnold et al. |
| 6,274,360 B1 | 8/2001 | Demain et al. |
| 6,361,988 B1 | 3/2002 | Arnold et al. |
| 6,524,837 B1 | 2/2003 | Arnold et al. |
| 6,537,746 B2 | 3/2003 | Arnold et al. |
| 6,540,895 B1 | 4/2003 | Spence et al. |
| 6,566,120 B2 | 5/2003 | Demain et al. |
| 6,643,591 B1 | 11/2003 | Korzekwa et al. |
| 6,902,918 B1 | 6/2005 | Arnold et al. |
| 7,202,266 B2 | 4/2007 | Arnold et al. |
| 7,205,304 B2 | 4/2007 | Van Emelen et al. |
| 7,214,298 B2 | 5/2007 | Spence et al. |
| 7,226,768 B2 | 6/2007 | Farinas et al. |
| 7,348,338 B2 | 3/2008 | Arnold et al. |
| 7,435,570 B2 | 10/2008 | Arnold et al. |
| 2003/0077795 A1 | 4/2003 | Wilson et al. |
| 2003/0077796 A1 | 4/2003 | Croteau et al. |
| 2003/0100744 A1 | 5/2003 | Farinas et al. |

FOREIGN PATENT DOCUMENTS

| | | |
|---|---|---|
| WO | WO 95/22625 | 8/1995 |
| WO | WO 97/20078 | 6/1997 |
| WO | WO 98/27230 | 6/1998 |
| WO | WO 98/42832 | 10/1998 |

OTHER PUBLICATIONS

Serioukova et al (1999 PNAS 96:1863-1868).*
Brock et al (1999 Archives of Biochemistry and Biophysics 373:401-408).*
Affholter et al. "Engineering a Revolution." *Chembytes e-zine* [Website] printed Apr. 14, 2004. http://www.chemsoc.org/chembytes/ezine/1999/arnold_apr99.htm Apr. 1999, 10 pages.
Meyer et al. "Library analysis of SCHEMA-guided protein recombination." *Protein Science* (2003), 12:1686-1693.
Otey et al. "Functional Evolution and Structural Conservation in Chimeric Cytochromes P450: Calibrating a Structure-Guided Approach." Chemistry & Biology, Mar. 2004: vol. 11, 309-318.
"Superfamily name: Cytochrome P450." From the Cytochrome P450 Webpage, printed Apr. 5, 2004 http://drnelson.utmem.edu/PIR.P450.description.html 2 pages.
Voigt et al: "Protein building blocks preserved by recombination." Nature Structural Biology, Jul. 2002: vol. 9 No. 7, 553-558.
Abecassis et al., "Design and characterization of a novel "family-shuffling" technology adapted to membrane enzyme: application to P450s involved in xenobiotic metabolism," Adv. Exp. Med. Biol. 500, 2001, pp. 319-322.
Abecassis et al., "Exploration of natural and artificial sequence spaces: Towards a functional remodeling of membrane-bound cytochrome P450," Biocatal. Biotransform, 2003, vol. 21, No. 2, pp. 55-66.
Assis et al., "Hydrocarbon oxidation with iodosylbenzene catalysed by the sterically hindered iron(III) 5-(pentafluorophenyl)-10, 15, 20-tris(2,6-dichlorophenyl) porphyrin in homogeneous solution and covalently bound to silica," Journal of The Chemical Society-Perkin Transactions 2, 1998, vol. 10, pp. 2221-2226.
Barnes et al., "Expression and enzymatic activity of recombinant cytochrome P450 17α-hydroxylase in *Escherichia coli*," Proc. Natl. Acad. Sci. USA, Jul. 1991, vol. 88, pp. 5597-5601.
Bell et al., "Butane and propane oxidation by engineered cytochrome P450(cam)," Chemical Communications, 2002, vol. 5, pp. 490-491.
Bell et al., "Engineering cytochrome P450cam into an alkane hydroxylase," Dalton Transactions, 2003, vol. 11, pp. 2133-2140.
Blay et al., "Alkane oxidation by a carbonxylate-bridged dimanganese(III) complex," Chemical Comuunications, 2001, vol. 20, pp. 2102-2103.

(Continued)

*Primary Examiner* — Christopher M Gross
(74) *Attorney, Agent, or Firm* — Knobbe, Martens, Olson & Bear LLP

(57) ABSTRACT

The present disclosure teaches that the recombination of homologous sequences of P450 enzymes, with the aid of SCHEMA to predict a resulting protein structure, is able to generate libraries of chimeras with significant functional diversity. Additionally, the members of these libraries demonstrate superior or unexpected new properties, which correlate with other factors that are observable in the library. Thus, the making of libraries of optimized P450 enzymes, the analysis of libraries to identify an optimized subset, and the optimized chimeras with improved or altered functionalities are all taught in the present disclosure.

15 Claims, 14 Drawing Sheets

(56) References Cited

OTHER PUBLICATIONS

Boddupalli et al., "Fatty acid monooxygenation by cytochrome P-450$_{BM-3}$," The Journal of Biological Chemistry, Mar. 15, 1990, vol. 265, No. 8, pp. 4233-4239.
Branden et al., "Introduction to protein structure," 1991, pp. 247, Garland Publishing Inc., New York.
Campbell et al., "Chimeric proteins can exceed the sum of their parts: Implication for evolution and protein design," Nat. Biotechnol, May 1997, vol. 15, pp. 439-443.
Capdevila et al., "The highly stereoselective oxidation of polyunsaturated fatty acids by cytochrome P450BM-3," The Journal of Biological Chemistry, Sep. 13, 1996, vol. 271, No. 37, pp. 22663-22671.
Chavez et al., "Syntheses, structures, and reactivities of cobalt(III)-alkylperoxo complexes and their role in stoichiometric and catalytic oxidation of hydrocarbons," Journal of the American Chemical Society, 1998, vol. 120, No. 35, pp. 9015-9027.
Chen et al., "Sterospecific alkane hydroxylation by non-heme iron catalysts: mechanistic evidence for an Fe-V = O active speices," Journal of the American Chemical Society, 2001, vol. 123, No. 26, pp. 6327-6337.
Christians et al., Directed evolution of thymidine kinase for AZT phosphorylation using DNA family shuffling, 1999, Nat. Biotechnol, vol. 17, pp. 259-264.
Cirino et al., "Exploring the diversity of heme enzymes through directed evolution," in *Directed Molecular Evolution of Proteins*, 2002, pp. 215-243, S. Brakmann and K. Johnsson, eds. (Germany: Wiley-VCH).
Crameri et al., "DNA shuffling of a family of genes from diverse species accelerates directed evolution," Nature, 1998, vol. 391, pp. 288-291.
Cui et al., "Recombinatoric exploration of novel folded structures: a heteropolymer-based model of protein evolutionary landscapes," Proc Natl Acad Sci USA, 2002, vol. 99, pp. 809-814.
de Visser et al., "Hydrogen bonding modulates the selectivity of enzymatic oxidation by P450: Chameleon oxidant behavior by compound I," Angewandte Chemie-International Edition, 2002, vol. 41, No. 11, pp. 1947-+.
de Visser et al., "What factors affect the regioselectivity of oxidation by cytochrome P450? A DFT study of allylic hydroxylation and double bond epoxidation in a model reaction," Journal of the American Chemical Society, 2002, vol. 124, No. 39, pp. 11809-11826.
Elliot et al., "Regio- and stereoselectivity of particulate methane monooxygenase from Methylococcus capsulatus (Bath)," Journal of the American Chemical Society, 1997, vol. 199, No. 42, pp. 9949-9955.
Farinas et al., "Directed evolution of a cytochrome P450 monooxygenase for alkane oxidation," Adv. Synth. Catal., 2001, vol. 343, pp. 601-606.
Fisher et al., "Positional specificity of rabbit CYP4B1 for omega-hydroxylation of short-medium chain fatty acids and hydrocarbons," Biochemical and Biophysical Research Communications, 1998, vol. 248, No. 2, pp. 352-355.
Gibbs et al., "Degenerate oligonucleotide gene shuffling (DOGS): a method for enhancing the frequency of recombination with family shuffling," Gene, 2001, vol. 271, pp. 13-20.
Glieder et al., High-throughput screens based on NAD(P)H depletion, Directed Enzyme Evolution: Screening and Selection Methods, 2003, vol. 230.
Glieder et al., "Laboratory evolution of a soluble, self-sufficient, highly active alkane hydroxylase," Nature Biotechnology, Nov. 2002, vol. 20, pp. 1-5.
Graham-Lorence et al., "An active site substitution, F87V, converts cytochrome P450 BM-3 into a region- and stereoselective (14S, 15R)-arachidonic acid epoxygenase," The Journal of Biological Chemistry, Jan. 10, 1997, vol. 272, No. 2, pp. 1127-1135.
Grogan, G., "Biocatalytic oxidation—an overview," University of York, Powerpoint presentation, Undated, 6 pages.
Hiraga et al., "General method for sequence-independent site-directed chimeragenesis," J. Mol. Biol., 2003, vol. 330, pp. 287-296.
Hopps, H.B., "Purpaid: a reagent that turns aldehydes purple," Aldrichim. Acta, 2000, vol. 33, pp. 28-30.
Horton et al., "Engineering hybrid genes without the use of restriction enzymes: gene splicing by overlap extention," Gene, 1989, vol. 77, pp. 61-68.
Jaeger et al., "Enantioselective biocatalysts optimized by directed evolution," Current Opinion in Biotechnology, 2004, vol. 15, No. 4, pp. 305-313.
Kumamaru et al., "Enhanced degradation of polychlorinated biphenyls by directed evolution of biphenyl dioxygenase," Nat. Biotechnol., 1998, vol. 16, pp. 663-666.
Li et al., "Residue size at position 87 of cytochrome P450 BM-3 determines its stereoselectivity in propylbenzene and 3-chlorostyrene oxidation," FEBS Lett 508, 2001, pp. 249-252.
Munro et al., "P450 BM3: The very model of a modern flavocytochrome," TRENDS Biochem. Sci., 2002, vol. 27, pp. 250-257.
Narhi et al., "Characterization of catalytically self-sufficient 119,000-dalton cytochrome P-450 monooxygenase induced by barbiturates in *Bacillus megaterium*," The Journal of Biological Chemistry, Jun. 5, 1986, vol. 261, No. 16, pp. 7160-7169.
Narhi et al., "Identification and characterization of two functional domains in cytochrome P-450$_{BM-3}$, a catalytically self-sufficient monooxygenase induced by barbiturates in *Bacillus megaterium*," The Journal of Biological Chemistry, May 15, 1987, vol. 262, No. 14, pp. 6683-6690.
Neylon, C., "Chemical and biochemical strategies for the randomization of protein encoding DNA sequences: library construction methods for directed evolution," Nucleic Acids Res., 2004, vol. 32, No. 4, pp. 1448-1459.
Ohkuma et al., "Cyp52 (Cytochrome-P450a1k) multigene family in candida-maltosa—Identification and characterization of 8 members," DNA and Cell Biology, 1995, vol. 14, No. 2, pp. 163-173.
Oliver et al., "Engineering the substrate specificity of *Bacillus megaterium* cytochrome P-450 BM3: hydroxylation of alkyl trimethylammonium compounds," Biochem. J., 1997, vol. 327, pp. 537-577.
O'Maille et al., Structure-based combinatorial protein engineering (SCOPE), J. Mol. Biol., 2002, vol. 321, pp. 677-691.
Peterson et al., "The many faces of P450s and their structural and functional implications," Sixth International Symposium on Cytochrome P450 Biodiversity: University of California, Los Angeles, 2002.
Pompon et al., Protein engineering by cDNA recombination in yeasts: shuffling of mammalian cytochrome P-450 functions, Gene, 1989, vol. 83, pp. 15-24.
Ramarao et al., "Identification by in Vitro mutagenesis of the interaction of two segments of C2MstC1, a chimera of cytochromes P450 2C2 and P450 2C1," The Journal of Biological Chemistry, Jan. 27, 1995, vol. 270, No. 4, pp. 1873-1880.
Ruettinger et al., "Epoxidation of unsaturated fatty acids by a soluble cytochrome P-450-dependent system from *Bacillus megaterium*," The Journal of Biological Chemistry, Jun. 10, 1981, vol. 256, No. 11, pp. 5728-5734.
Schneider et al., "Controlled regioselectivity of fatty acid oxidation by whole cells producing cytochrome P450(BM-3) monooxygenase under varied dissolved oxygen concentrations," Biotech. Bioeng., 1999, vol. 64, No. 3, pp. 333-340.
Schneider et al., "Production of chiral hydroxyl long chain fatty acids by whole cell biocatalysis of pentadecanoic acid with an *E. coli* recombinant containing cytochrome P450(BM-3) monooxygenase," Tetrahedron Asymmetry, 1998, vol. 9, No. 16, pp. 2833-2844.
Schwaneberg et al., "Cost-effective whole-cell assay for laboratory evolution of hydroxylases in *Escherichia coli*.," Journal of Biomolecular Screening, 2001, vol. 6, No. 2, pp. 111-117.
Seghezzi et al., "Identification of characterization of additional members of the cytochrome-P450 multigene family Cyp52 of candida-tropicalis," DNA and Cell Biology, 1992, vol. 11, No. 10, pp. 767-780.
Stevenson et al., "Engineering molecular recognition in alkane oxidation catalysed by cytochrome P450(cam)," New Journal of Chemistry, 1998, vol. 22, No. 6, pp. 551-552.

(56) References Cited

OTHER PUBLICATIONS

Stevenson et al., "The catalytic oxidation of linear and branched alkanes by cytochrome P450cam.," J. Am. Chem. Soc., 1996, vol. 118, pp. 12846-12847.
Taly et al., "A combinatorial approach to substrate discrimination in the P450 CYP1A subfamily," Biochimica et Biophysica Acta, 2007, vol. 1770, pp. 446-457.
Tsotsou et al., "High throughput assay for cytochrome P450BM3 for screening libraries of substrates and combinatorial mutants," Biosensors & Bioelectronics, 2002, vol. 17, No. 1-2, pp. 119-131.
Urlacher et al., "Biotransformations using prokaryotic P450 monooxygenases," Current Opinion in Biotechnology, 2002, vol. 13, pp. 557-564.
Wubbolts et al., "Enantioselective oxidation by non-heme iron monooxygenases from Pseudomonas," CHIMIA, 1996, vol. 50, No. 9, pp. 436-437.
Abecassis et al., Nucleic Acids Res 28:E88 (2000).
Appel et al., "A P450 BM-3 mutant hydroxylates alkanes, cycloalkanes, arenes and heteroarenes," *J. Biotechnol.*, 88:167-171 (Jun. 15, 2001).
Cirino et al., "Protein Engineering of Oxygenases for Biocatalysis," Current Opinion in Chemical Engineering, California Institute of Technology, Pasadena, 130-135 )(2002).
Cirino et al., "Regioselectivity and Activity of Cytochrome P450 BM-3 and Mutant F87A in Reactions Driven by Hydrogen Peroxide" *Adv. Synth. Catal.* 344, No. 9, 932-937 (2002).
Cirino et al., Angew Chem Int Ed Engl 42, 3299-3301 (2003).
Coco et al., Nat. Biotechnol., 19:3540359 (2001).
Glieder et al., Nat. Biotechnol. 20:1135-1139 (2002).
Glieder et al., "Laboratory Evolution of a Soluble, Self-Sufficient, Highly Active Alkane Hydroxylase," *Nature Biotechnology*, vol. 43, No. 7 (2004).
Gonzalez et al., "Evolution of the P450 gene superfamily: animal-plant 'warfare', molecular drive and human genetic differences in drug oxidation," *Trends Genet*, 6:182-186 (1990).
Gotoh, O., Cytochrome P450, $2^{nd}$ Edition, pp. 255-272 (1993).
Grogan, G., "Biocatalytic Oxidation—An Overview," York Structural Biology Laboratory, The University of York.
Hansson et al., J. Mol. Biol. 287:265-276 (1999).
Joo et al., Nature, 399:670-673 (1999).
Kikuchi et al., Gene, 243:133-137 (2000).
Li et al., Chemistry, 6:1531-1536 (2000).
Li et al., Biochem Biophys. Acta., 1545-114-121 (2001).
Lutz et al., Proc Natl Acad Sci USA 98:11248-1253 (2001).
Mauersberger et al., Z Alig Mikrobiol., 121:313-321 (1981).
Mayhew, "Benzycycloarene Hydroxylation by P450 Biocatalysis," New J. Chem., 26, 35-42 (2002).
Murataliev et al., "Chimeragenesis of the Fatty Acid Binding Site of Cytochrome P450BM3. Replacement of Residues 73-84 with the Homologous Residues from the Insect Cytochrome P450 CYP4C7," *Biochemistry* 43, 1771-1780 (2004).
Porter, Todd D., Ph.D., "Cytochrome P450 Reductase" printed Apr. 5, 2004 http://www.uky.edu/Pharmacy/ps/porter/CPR.htm.
Porter et al., J. Biol. Chem., 266:13469-13472 (1991).
Sieber et al. Nat Biotechnol. 19:456-460 (2001).
Sono et al., "Heme-Containing Oxygenases," *Chem Rev* 96, 2841-2888 (1996).
Stemmer, W.P., Proc. Natl. Acad. Sci. USA, 91:10747-10751 (1994).
Volkov et al., Nucleic Acids Res., 27, e18 (1999).
Zhao et al. Nat. Biotechnol. (1998).
"Enzymology of Cytochrome P450 Reductase" printed Apr. 5, 2004 http://www.uky.edu/Pharmacy/ps/porter/CPR_enzymology.htm.
"Researchers Break Electronics Speed Record. *New Diode May Lead to New Generation of Faster, Cheaper, Smaller Electronics*" printed Apr. 14, 2004 http://www.nsf.gov/od/lpa/news/04/tip040115.htm.
Beguin, P. Hybrid enzymes. Curr Opin Biotechnol, 1999, 10: 336-340.

Bogarad et al. A hierarchical approach to protein molecular evolution. Proc Natl Acad Sci USA, Mar. 1999, 96: 2591-2595.
Childs et al. The Steady-State Kinetics of Peroxidase with 2,2'-Azino-di-(3-ethyl=benzthiazoline-6-sulphonic acid) as Chromogen. Biochem J. 1997, 145: 93-103.
Eichhorn et al., Heme Proteins 7, New York, NY: Elsevier Science Publishing Co., Inc. (1988).
Haines et al. Pivotal Role of Water in the Mechanism of P450BM-3, Biochemistry 2001, 40: 13456-13465.
Li et al. The structure of the cytochrome p450BM-3 haem domain complexed with the fatty acid substrate, palmitoleic acid. Nat Struct Biol, Feb. 1997, 4(2):140-146.
Mansuy, D., The great diversity of reactions catalyzed by cytochromes P450. Comp Biochem Physiol Part C, 1998, 121, 5-14.
Martinis et al. Probing the Heme Iron Coordination Structure of Pressure-Indyced Cytochrome $P420_{cam}$. Biochemistry, 1996, 35: 14530-14536.
Modi et al. The catalytic mechanism of cytochrome P450 BM3 involves a 6 Å movement of the bound substrate on reduction. Nat Struct Biol. May 1996, 3(5): 414-417.
Moore et al. Strategies for the in vitro Evolution of Protein Function: Enzyme Evolution by Random Recombination of Improved Sequences. J Mol Biol, 1997, 272: 336-347.
Nakagawa et al. Construction of Catalase Deficient *Escherichia coli* Strains for the Production of Uricase. Biosci Biotechnol Biochem, 1996, 60(3): 415-420.
Narhi et al. Partial characterization of a barbiturate-induced cytochrome P-450-dependant fatty acid monooxygenase from Bacillus megaterium. Biochem Biophys Res Commun Nov. 15, 1983, 116 (3): 851-858.
Omura et al. The Carbon Monoxide-binding Pigment of Liver Microsomes. J. Biol. Chem, Jul. 1964, 239(7): 2370-2378.
Ortiz De Montellano, P.R., Cytochrome P450: Structure, Mechanism, and Biochemistry (New York: Plenum Press)(1995) pp. xi-xii and 83-305.
Otey et al., High-throughput screen for aromatic hydroxylation. In Directed Enzyme Evolution: Screening and Selection Methods, 2003, F.H. Arnold and G. Georiou, eds. (Totowa, NJ: Humana Press), pp. 141-148.
Paulsen et al. Dramatic differences in the motions of the mouth of open and closed cytochrome P450BM-3 by molecular dynamics simulations. Proteins, Mar. 1995, 21: 237-243.
Raillard et al. Novel enzyme activities and functional plasticity revealed by recombining highly homologous enzymes. Chem Biol, 2001, 8, 891-898.
Ravichandran et al. Crystal Structure of Hemoprotein Domain of P450BM-3, a Protoype for Microsomal P450's. Science, Aug. 6, 1993, 261: 731-736.
Schwaneberg et al. A Continuous Spectrophotometric Assay for P450 BM-3, a Fatty Acid Hydroxylating Enzyme, and Its Mutant F87A. Analytical Biochemistry, 1999, 269: 359-366.
Wells et al. Resonance Raman Investigations of *Escherichia coli*-Expressed *Pseudomonas putida* Cytochrome P450 and P420. Biochemistry, 1992, 31: 4384-4393.
Zha et al. Complete reversal of enantioselectivity of an enzyme-catalyzed reaction by directed evolution. Chem. Commun. 2001, 24, 2664-2665.
Zhang et al. Directed evolution of a fucosidase from a galactosidase by DNA shuffling and screening. Proc Natl Acad Sci USA, Apr. 1997, 94: 4504-4509.
Brock et al. The Use of Random Chimeragenesis to Study Structure/ Function Properties of Rat and Human P450c17. Archives of Biochemistry and Biophysics, Jan. 15, 2000, 373 (2): 401-408.
Otey et al. Structure-Guided Recombination Creates an Artificial Family of Cytochromes P450. PLoS Biology, May 2006, 4(5): el 12, p. 0789-0798.

* cited by examiner

```
                              SEQUENCE LISTING

<160> NUMBER OF SEQ ID NOS: 108

<210> SEQ ID NO 1
<211> LENGTH: 1392
<212> TYPE: DNA
<213> ORGANISM: Bacillus megaterium

<400> SEQUENCE: 1
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag gagacgggtt ggccactagt tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggcttttaac   480 tatcgcttta acagctttta ccgagatcag cctcatccat ttattacaag tatggtccgt     540
gcactggatg aagcaatgaa caagctgcag cgagcaaatc cagacgaccc agcttatgat     600
gaaaacaagc gccagtttca agaagatatc aaggtgatga acgacctagt agataaaatt     660
attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaac taatggttct gattcctcag    1080
cttcaccgtg ataaaacaat tgggagagac gatgtggaag agttccgtcc agagcgtttt    1140
gaaaatccaa gtgcgattcc gcagcatgcg tttaaaccgt tggaaacgg tcagcgtgcg     1200 tgtatcggtc agcagttcgc tcttcatgaa gcaacgctgg tacttggtat gatgctaaaa    1260
cactttgact ttgaagatca tacaaactac gagctggata ttaaagaaac tttaacgtta    1320
aaacctgaag gctttgtggt aaaagcaaaa tcgaaaaaaa ttccgcttgg cggtattcct    1380
tcacctagca ct                                                       1392

<210> SEQ ID NO 2
<211> LENGTH: 463
```

<212> TYPE: PRT
<213> ORGANISM: Bacillus megaterium

<400> SEQUENCE: 2

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
         35                  40                  45

Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Phe Val Arg Asp
 65                  70                  75                  80

Phe Ala Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400
```

```
Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr
            450                 455                 460

<210> SEQ ID NO 3
<211> LENGTH: 1401
<212> TYPE: DNA
<213> ORGANISM: Bacillus subtilis

<400> SEQUENCE: 3
atgaaggaaa caagcccgat tcctcagccg aagacgtttg gccgctcgg caatttgcct      60
ttaattgata agacaaaacc gacgctttcg ctgatcaaac tggcggaaga cagggcccg    120
atttttcaaa tccatacacc cgcgggcacg accattgtag tgtccggcca tgaattggtg    180
aaagaggttt gtgatgaaga cggtttgat aaaagcattg aaggcgcctt ggaaaaggtt    240
cgcgcatttt ccggtgacgg attggccact agttggacgc atgagcctaa ctggagaaaa    300
gcgcacaaca ttctgatgcc gacgttcagc cagcgggcca tgaaggacta tcatgagaaa    360
atggtcgata tcgctgttca gctcattcaa aaatgggcaa ggctcaaccc gaatgaagca    420
gtcgatgtcc cgggagatat gacccggctg acgctcgaca ccattgggct atgcgggttt    480
aactaccgct ttaacagtta ctacagagaa cgccccacc cgtttatcaa cagcatggtg    540
cgggcgcttg atgaagcgat gcatcaaatg cagcggcttg atgttcaaga taagcttatg    600
gtcagaacaa agcggcaatt ccgctatgat attcaaacga tgttttcgtt agtcgacagc    660
attattgcag agcgcagggc gaatggagac caggatgaaa aagatttgct cgcccgcatg    720
ctgaatgtgg aagatccgga aactggtgaa aagctcgacg acgaaaatat ccgctttcag    780
atcatcacgt ttttgattgc cggccatgaa acaacgagcg gcctgctttc ctttgcgact    840
tacttttat tgaagcatcc tgacaaactg aaaaaggcgt atgaagaggt cgatcgggtg    900
ctgacggatg cagcgccgac ctataaacaa gtgctggagc ttacatacat acggatgatt    960
ttaaatgaat cactgcgctt atggccgaca gctccggctt tcagccttta tccaaaagaa   1020
gacacagtca ttggcggaaa atttccgatc acgacgaatg acagaatttc tgtgctgatt   1080
ccgcagcttc atcgtgatcg agacgcttgg ggaaaggacg cagaagagtt ccggccggaa   1140
cggtttgagc atcaggacca agtgcctcat catgcgtaca aaccattcgg aaatggacaa   1200
cgggcctgta tcggcatgca gtttgcccctt catgaagcca cacttgtgtt aggcatgatt   1260
ctaaaatatt tcacattgat tgatcatgag aattatgagc ttgatatcaa acaaacctta   1320
acacttaagc cgggcgattt tcacatcagt gttcaaagcc gtcatcagga agccattcat   1380
gcagacgtcc aggcagctga a                                              1401

<210> SEQ ID NO 4
<211> LENGTH: 466
<212> TYPE: PRT
<213> ORGANISM: Bacillus subtilis

<400> SEQUENCE: 4

Lys Glu Thr Ser Pro Ile Pro Gln Pro Lys Thr Phe Gly Pro Leu Gly
  1               5                  10                  15

Asn Leu Pro Leu Ile Asp Lys Asp Lys Pro Thr Leu Ser Leu Ile Lys
```

```
             20                  25                  30
Leu Ala Glu Glu Gln Gly Pro Ile Phe Gln Ile His Thr Pro Ala Gly
         35                  40                  45

Thr Thr Ile Val Val Ser Gly His Glu Leu Val Lys Glu Val Cys Asp
 50                  55                  60

Glu Glu Arg Phe Asp Lys Ser Ile Glu Gly Ala Leu Glu Lys Val Arg
 65                  70                  75                  80

Ala Phe Ser Gly Asp Gly Leu Ala Thr Ser Trp Thr His Glu Pro Asn
                 85                  90                  95

Trp Arg Lys Ala His Asn Ile Leu Met Pro Thr Phe Ser Gln Arg Ala
                 100                 105                 110

Met Lys Asp Tyr His Glu Lys Met Val Asp Ile Ala Val Gln Leu Ile
                 115                 120                 125

Gln Lys Trp Ala Arg Leu Asn Pro Asn Glu Ala Val Asp Val Pro Gly
         130                 135                 140

Asp Met Thr Arg Leu Thr Leu Asp Thr Ile Gly Leu Cys Gly Phe Asn
145                 150                 155                 160

Tyr Arg Phe Asn Ser Tyr Tyr Arg Glu Thr Pro His Pro Phe Ile Asn
                 165                 170                 175

Ser Met Val Arg Ala Leu Asp Glu Ala Met His Gln Met Gln Arg Leu
                 180                 185                 190

Asp Val Gln Asp Lys Leu Met Val Arg Thr Lys Arg Gln Phe Arg Tyr
                 195                 200                 205

Asp Ile Gln Thr Met Phe Ser Leu Val Asp Ser Ile Ile Ala Glu Arg
         210                 215                 220

Arg Ala Asn Gly Asp Gln Asp Glu Lys Asp Leu Leu Ala Arg Met Leu
225                 230                 235                 240

Asn Val Glu Asp Pro Glu Thr Gly Glu Lys Leu Asp Asp Glu Asn Ile
                 245                 250                 255

Arg Phe Gln Ile Ile Thr Phe Leu Ile Ala Gly His Glu Thr Thr Ser
                 260                 265                 270

Gly Leu Leu Ser Phe Ala Thr Tyr Phe Leu Leu Lys His Pro Asp Lys
         275                 280                 285

Leu Lys Lys Ala Tyr Glu Glu Val Asp Arg Val Leu Thr Asp Ala Ala
 290                 295                 300

Pro Thr Tyr Lys Gln Val Leu Glu Leu Thr Tyr Ile Arg Met Ile Leu
305                 310                 315                 320

Asn Glu Ser Leu Arg Leu Trp Pro Thr Ala Pro Ala Phe Ser Leu Tyr
                 325                 330                 335

Pro Lys Glu Asp Thr Val Ile Gly Gly Lys Phe Pro Ile Thr Thr Asn
                 340                 345                 350

Asp Arg Ile Ser Val Leu Ile Pro Gln Leu His Arg Asp Arg Asp Ala
                 355                 360                 365

Trp Gly Lys Asp Ala Glu Glu Phe Arg Pro Glu Arg Phe Glu His Gln
         370                 375                 380

Asp Gln Val Pro His His Ala Tyr Lys Pro Phe Gly Asn Gly Gln Arg
385                 390                 395                 400

Ala Cys Ile Gly Met Gln Phe Ala Leu His Glu Ala Thr Leu Val Leu
                 405                 410                 415

Gly Met Ile Leu Lys Tyr Phe Thr Leu Ile Asp His Glu Asn Tyr Glu
                 420                 425                 430

Leu Asp Ile Lys Gln Thr Leu Thr Leu Lys Pro Gly Asp Phe His Ile
         435                 440                 445
```

-continued

```
Ser Val Gln Ser Arg His Gln Glu Ala Ile His Ala Asp Val Gln Ala
450                 455                 460

Ala Glu
465

<210> SEQ ID NO 5
<211> LENGTH: 463
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 5

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Thr Tyr Phe Leu Leu Lys His Pro Asp Lys Leu Lys
        275                 280                 285

Lys Ala Tyr Glu Glu Val Asp Arg Val Leu Thr Asp Ala Ala Pro Thr
    290                 295                 300

Tyr Lys Gln Val Leu Glu Leu Thr Tyr Ile Arg Met Ile Leu Asn Glu
305                 310                 315                 320

Ser Leu Arg Leu Trp Pro Thr Ala Pro Ala Phe Ser Leu Tyr Pro Lys
                325                 330                 335
```

```
Glu Asp Thr Val Ile Gly Gly Lys Phe Pro Ile Thr Thr Asn Asp Arg
            340                 345                 350

Ile Ser Val Leu Ile Pro Gln Leu His Arg Asp Arg Asp Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr
450                 455                 460
```

<210> SEQ ID NO 6
<211> LENGTH: 464
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 6

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
             35                  40                  45

Thr Arg Tyr Leu Ser Ser Gln Arg Leu Ile Lys Glu Ala Cys Asp Glu
         50                  55                  60

Glu Arg Phe Asp Lys Ser Ile Glu Gly Ala Leu Glu Lys Val Arg Ala
 65                  70                  75                  80

Phe Ser Gly Asp Gly Leu Ala Thr Ser Trp Thr His Glu Pro Asn Trp
                 85                  90                  95

Arg Lys Ala His Asn Ile Leu Met Pro Thr Phe Ser Gln Arg Ala Met
            100                 105                 110

Lys Asp Tyr His Glu Lys Met Val Asp Ile Ala Val Gln Leu Ile Gln
            115                 120                 125

Lys Trp Ala Arg Leu Asn Pro Asn Glu Ala Val Asp Val Pro Gly Asp
130                 135                 140

Met Thr Arg Leu Thr Leu Asp Thr Ile Gly Leu Cys Gly Phe Asn Tyr
145                 150                 155                 160

Arg Phe Asn Ser Tyr Tyr Arg Glu Thr Pro His Pro Phe Ile Asn Ser
                165                 170                 175

Met Val Arg Ala Leu Asp Glu Ala Met His Gln Met Gln Arg Leu Asp
            180                 185                 190

Val Gln Asp Lys Leu Met Val Arg Thr Lys Arg Gln Phe Arg Tyr Asp
            195                 200                 205

Ile Gln Thr Met Phe Ser Leu Val Asp Ser Ile Ile Ala Glu Arg Arg
            210                 215                 220

Ala Asn Gly Asp Gln Asp Glu Lys Asp Leu Leu Ala Arg Met Leu Asn
225                 230                 235                 240
```

-continued

```
Val Glu Asp Pro Glu Thr Gly Glu Lys Leu Asp Asp Glu Asn Ile Arg
                245                 250                 255

Phe Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460
```

<210> SEQ ID NO 7
<211> LENGTH: 466
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 7

```
Lys Glu Thr Ser Pro Ile Pro Gln Pro Lys Thr Phe Gly Pro Leu Gly
1               5                   10                  15

Asn Leu Pro Leu Ile Asp Lys Asp Lys Pro Thr Leu Ser Leu Ile Lys
            20                  25                  30

Leu Ala Glu Glu Gln Gly Pro Ile Phe Gln Ile His Thr Pro Ala Gly
        35                  40                  45

Thr Thr Ile Val Val Ser Gly His Glu Leu Val Lys Glu Val Cys Asp
    50                  55                  60

Glu Glu Arg Phe Asp Lys Ser Ile Glu Gly Ala Leu Glu Lys Val Arg
65                  70                  75                  80

Ala Phe Ser Gly Asp Gly Leu Ala Thr Ser Trp Thr His Glu Pro Asn
                85                  90                  95

Trp Arg Lys Ala His Asn Ile Leu Met Pro Thr Phe Ser Gln Arg Ala
            100                 105                 110

Met Lys Asp Tyr His Glu Lys Met Val Asp Ile Ala Val Gln Leu Ile
        115                 120                 125

Gln Lys Trp Ala Arg Leu Asn Pro Asn Glu Ala Val Asp Val Pro Gly
    130                 135                 140
```

```
Asp Met Thr Arg Leu Thr Leu Asp Thr Ile Gly Leu Cys Gly Phe Asn
145                 150                 155                 160

Tyr Arg Phe Asn Ser Tyr Tyr Arg Glu Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Met Val Arg Thr Lys Arg Gln Phe Arg Tyr
        195                 200                 205

Asp Ile Gln Thr Met Phe Ser Leu Val Asp Ser Ile Ile Ala Glu Arg
210                 215                 220

Arg Ala Asn Gly Asp Gln Asp Glu Lys Asp Leu Leu Ala Arg Met Leu
225                 230                 235                 240

Asn Val Glu Asp Pro Glu Thr Gly Glu Lys Leu Asp Asp Glu Asn Ile
                245                 250                 255

Arg Phe Gln Ile Ile Thr Phe Leu Ile Ala Gly His Glu Thr Thr Ser
                260                 265                 270

Gly Leu Leu Ser Phe Ala Thr Tyr Phe Leu Leu Lys His Pro Asp Lys
            275                 280                 285

Leu Lys Lys Ala Tyr Glu Glu Val Asp Arg Val Leu Thr Asp Ala Ala
        290                 295                 300

Pro Thr Tyr Lys Gln Val Leu Glu Leu Thr Tyr Ile Arg Met Ile Leu
305                 310                 315                 320

Asn Glu Ser Leu Arg Leu Trp Pro Thr Ala Pro Ala Phe Ser Leu Tyr
                325                 330                 335

Pro Lys Glu Asp Thr Val Ile Gly Gly Lys Phe Pro Ile Thr Thr Asn
                340                 345                 350

Asp Arg Ile Ser Val Leu Ile Pro Gln Leu His Arg Asp Arg Asp Ala
            355                 360                 365

Trp Gly Lys Asp Ala Glu Glu Phe Arg Pro Glu Arg Phe Glu His Gln
        370                 375                 380

Asp Gln Val Pro His His Ala Tyr Lys Pro Phe Gly Asn Gly Gln Arg
385                 390                 395                 400

Ala Cys Ile Gly Met Gln Phe Ala Leu His Glu Ala Thr Leu Val Leu
                405                 410                 415

Gly Met Ile Leu Lys Tyr Phe Thr Leu Ile Asp His Glu Asn Tyr Glu
                420                 425                 430

Leu Asp Ile Lys Gln Thr Leu Thr Leu Lys Pro Gly Asp Phe His Ile
            435                 440                 445

Ser Val Gln Ser Arg His Gln Glu Ala Ile His Ala Asp Val Gln Ala
        450                 455                 460

Ala Glu
465

<210> SEQ ID NO 8
<211> LENGTH: 464
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 8

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30
```

-continued

```
Ala Asp Glu Leu Gly Glu Ile Phe Lys Phe Glu Ala Pro Gly Arg Val
         35                  40                  45
Thr Arg Tyr Leu Ser Ser Gln Arg Leu Ile Lys Glu Ala Cys Asp Glu
 50                  55                  60
Ser Arg Phe Asp Lys Ser Ile Glu Gly Ala Leu Glu Lys Val Arg Ala
 65                  70                  75                  80
Phe Ser Gly Asp Gly Leu Ala Thr Ser Trp Thr His Glu Pro Asn Trp
                 85                  90                  95
Arg Lys Ala His Asn Ile Leu Met Pro Thr Phe Ser Gln Arg Ala Met
             100                 105                 110
Lys Asp Tyr His Glu Lys Met Val Asp Ile Ala Val Gln Leu Ile Gln
             115                 120                 125
Lys Trp Ala Arg Leu Asn Pro Asn Glu Ala Val Asp Val Pro Gly Asp
130                 135                 140
Met Thr Arg Leu Thr Leu Asp Thr Ile Gly Leu Cys Gly Phe Asn Tyr
145                 150                 155                 160
Arg Phe Asn Ser Tyr Tyr Arg Glu Thr Pro His Pro Phe Ile Asn Ser
                165                 170                 175
Met Val Arg Ala Leu Asp Glu Ala Met His Gln Met Gln Arg Leu Asp
             180                 185                 190
Val Gln Asp Lys Leu Met Val Arg Thr Lys Arg Gln Phe Arg Tyr Asp
             195                 200                 205
Ile Gln Thr Met Phe Ser Leu Val Asp Ser Ile Ile Ala Glu Arg Arg
210                 215                 220
Ala Asn Gly Asp Gln Asp Glu Lys Asp Leu Leu Ala Arg Met Leu Asn
225                 230                 235                 240
Val Glu Asp Pro Glu Thr Gly Glu Lys Leu Asp Asp Glu Asn Ile Arg
                245                 250                 255
Phe Gln Ile Ile Thr Phe Leu Ile Ala Gly His Glu Thr Thr Ser Gly
             260                 265                 270
Leu Leu Ser Phe Ala Thr Tyr Phe Leu Leu Lys His Pro Asp Lys Leu
             275                 280                 285
Lys Lys Ala Tyr Glu Glu Val Asp Arg Val Leu Thr Asp Pro Val Pro
290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
             340                 345                 350
Glu Leu Met Val Leu Ile Pro Gln Leu His Arg Asp Lys Thr Ile Trp
             355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
             420                 425                 430
Asp Ile Lys Glu Thr Leu Thr Leu Lys Pro Glu Gly Phe Val Val Lys
             435                 440                 445
Ala Lys Ser Lys Lys Ile Pro Leu Gly Gly Ile Pro Ser Pro Ser Thr
450                 455                 460
```

<210> SEQ ID NO 9
<211> LENGTH: 463
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 9

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Val Arg Asp
 65                  70                  75                  80

Phe Ala Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Arg Asp Ala Trp Gly
        355                 360                 365
```

```
Lys Asp Ala Glu Glu Phe Arg Pro Glu Arg Phe Glu His Gln Asp Gln
    370                 375                 380

Val Pro His His Ala Tyr Lys Pro Phe Gly Asn Gly Gln Arg Ala Cys
385                 390                 395                 400

Ile Gly Met Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr
450                 455                 460
```

<210> SEQ ID NO 10
<211> LENGTH: 463
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 10

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Phe Val Arg Asp
 65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Thr Pro His Pro Phe Ile Asn Ser
                165                 170                 175

Met Val Arg Ala Leu Asp Glu Ala Met His Gln Met Gln Arg Leu Asp
            180                 185                 190

Val Gln Asp Lys Leu Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270
```

```
Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr
        450                 455                 460

<210> SEQ ID NO 11
<211> LENGTH: 463
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 11

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175
```

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro Asp Lys Leu Lys
        275                 280                 285

Lys Ala Tyr Glu Glu Val Asp Arg Val Leu Thr Asp Ala Ala Pro Thr
290                 295                 300

Tyr Lys Gln Val Leu Glu Leu Thr Tyr Ile Arg Met Ile Leu Asn Glu
305                 310                 315                 320

Ser Leu Arg Leu Trp Pro Thr Ala Pro Ala Phe Ser Leu Tyr Pro Lys
                325                 330                 335

Glu Asp Thr Val Ile Gly Gly Val Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr
450                 455                 460

<210> SEQ ID NO 12
<211> LENGTH: 463
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 12

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

```
Phe Ala Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Lys Met Val Asp Ile Ala Val Gln Leu Ile Gln
            115                 120                 125

Lys Trp Ala Arg Leu Asn Pro Asn Glu Ala Val Asp Val Pro Gly Asp
        130                 135                 140

Met Thr Arg Leu Thr Leu Asp Thr Ile Gly Leu Cys Gly Phe Asn Tyr
145                 150                 155                 160

Arg Phe Asn Ser Tyr Tyr Arg Glu Thr Pro His Pro Phe Ile Asn Ser
                165                 170                 175

Met Val Arg Ala Leu Asp Glu Ala Met His Gln Met Gln Arg Leu Asp
            180                 185                 190

Val Gln Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
                305                 310                 315                 320

Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
        340                 345                 350

Leu Met Val Leu Ile Pro Gln Leu His Arg Asp Lys Thr Ile Trp Gly
    355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr
    450                 455                 460

<210> SEQ ID NO 13
<211> LENGTH: 465
<212> TYPE: PRT
<213> ORGANISM: Artificial Sequence
<220> FEATURE:
<223> OTHER INFORMATION: Chimeric Cytochrome P450 heme group sequence
``` from Bacillus megaterium and Bacillus subtilis

<400> SEQUENCE: 13

```
Lys Glu Thr Ser Pro Ile Pro Gln Pro Lys Thr Phe Gly Pro Leu Gly
1               5                   10                  15

Asn Leu Pro Leu Ile Asp Lys Asp Lys Pro Thr Leu Ser Leu Ile Lys
            20                  25                  30

Leu Ala Glu Glu Gln Gly Pro Ile Phe Gln Ile His Thr Pro Ala Gly
        35                  40                  45

Thr Thr Ile Val Val Ser Gly His Glu Leu Val Lys Glu Val Cys Asp
    50                  55                  60

Glu Glu Arg Phe Asp Lys Ser Ile Glu Gly Ala Leu Glu Lys Val Arg
65                  70                  75                  80

Ala Phe Ser Gly Asp Gly Leu Ala Thr Ser Trp Thr His Glu Pro Asn
                85                  90                  95

Trp Arg Lys Ala His Asn Ile Leu Met Pro Thr Phe Ser Gln Arg Ala
            100                 105                 110

Met Lys Asp Tyr His Glu Lys Met Val Asp Ile Ala Val Gln Leu Ile
        115                 120                 125

Gln Lys Trp Ala Arg Leu Asn Pro Asn Glu Ala Val Asp Val Pro Gly
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Thr Tyr Phe Leu Leu Lys His Pro Asp Lys Leu
        275                 280                 285

Lys Lys Ala Tyr Glu Glu Val Asp Arg Val Leu Thr Asp Ala Ala Pro
    290                 295                 300

Thr Tyr Lys Gln Val Leu Glu Leu Thr Tyr Ile Arg Met Ile Leu Asn
305                 310                 315                 320

Glu Ser Leu Arg Leu Trp Pro Thr Ala Pro Ala Phe Ser Leu Tyr Pro
                325                 330                 335

Lys Glu Asp Thr Val Ile Gly Gly Lys Phe Pro Ile Thr Thr Asn Asp
            340                 345                 350

Arg Ile Ser Val Leu Ile Pro Gln Leu His Arg Asp Arg Asp Ala Trp
        355                 360                 365

Gly Lys Asp Ala Glu Glu Phe Arg Pro Glu Arg Phe Glu His Gln Asp
    370                 375                 380

Gln Val Pro His His Ala Tyr Lys Pro Phe Gly Asn Gly Gln Arg Ala
385                 390                 395                 400

Cys Ile Gly Met Gln Phe Ala Leu His Glu Ala Thr Leu Val Leu Gly
```

```
                    405                 410                 415
Met Ile Leu Lys Tyr Phe Thr Leu Ile Asp His Glu Asn Tyr Glu Leu
                420                 425                 430

Asp Ile Lys Gln Thr Leu Thr Leu Lys Pro Gly Asp Phe His Ile Ser
            435                 440                 445

Val Gln Ser Arg His Gln Glu Ala Ile His Ala Asp Val Gln Ala Ala
        450                 455                 460

Glu
465

<210> SEQ ID NO 14
<211> LENGTH: 463
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 14

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Ile Val Val Ser Gly His Glu Leu Val Lys Glu Val Cys Asp Glu
        50                  55                  60

Glu Arg Phe Asp Lys Ser Ile Glu Gly Ala Leu Glu Lys Val Arg Ala
65                  70                  75                  80

Phe Ser Gly Asp Gly Leu Ala Thr Ser Trp Thr His Glu Pro Asn Trp
                85                  90                  95

Arg Lys Ala His Asn Ile Leu Met Pro Thr Phe Ser Gln Arg Ala Met
                100                 105                 110

Lys Asp Tyr His Glu Lys Met Val Asp Ile Ala Val Gln Leu Ile Gln
            115                 120                 125

Lys Trp Ala Arg Leu Asn Pro Asn Glu Ala Val Asp Val Pro Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
```

```
                290                 295                 300
Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Leu Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr
450                 455                 460

<210> SEQ ID NO 15
<211> LENGTH: 464
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 15

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
                35                  40                  45

Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Phe Val Arg Asp
 65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Pro Glu Asp
                130                 135                 140

Met Thr Arg Leu Thr Leu Asp Thr Ile Gly Leu Cys Gly Phe Asn Tyr
145                 150                 155                 160

Arg Phe Asn Ser Tyr Tyr Arg Glu Thr Pro His Pro Phe Ile Asn Ser
                165                 170                 175

Met Val Arg Ala Leu Asp Glu Ala Met His Gln Met Gln Arg Leu Asp
                180                 185                 190

Val Gln Asp Lys Leu Met Val Arg Thr Lys Arg Gln Phe Arg Tyr Asp
```

```
            195                 200                 205
Ile Gln Thr Met Phe Ser Leu Val Asp Ser Ile Ile Ala Glu Arg Arg
210                 215                 220

Ala Asn Gly Asp Gln Asp Glu Lys Asp Leu Leu Ala Arg Met Leu Asn
225                 230                 235                 240

Val Glu Asp Pro Glu Thr Gly Glu Lys Leu Asp Asp Glu Asn Ile Arg
                245                 250                 255

Phe Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Ala Ala Glu Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
        450                 455                 460

<210> SEQ ID NO 16
<211> LENGTH: 464
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 16

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
```

```
                    100                 105                 110
Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Leu Asp
            180                 185                 190

Val Gln Asp Lys Leu Met Val Arg Thr Lys Arg Gln Phe Arg Tyr Asp
        195                 200                 205

Ile Gln Thr Met Phe Ser Leu Val Asp Ser Ile Ile Ala Glu Arg Arg
    210                 215                 220

Ala Asn Gly Asp Gln Asp Glu Lys Asp Leu Leu Ala Arg Met Leu Asn
225                 230                 235                 240

Val Glu Asp Pro Glu Thr Gly Glu Lys Leu Asp Asp Glu Asn Ile Arg
                245                 250                 255

Phe Gln Ile Ile Thr Phe Leu Ile Ala Gly His Glu Thr Thr Ser Gly
            260                 265                 270

Leu Leu Ser Phe Ala Thr Tyr Phe Leu Leu Lys His Pro Asp Lys Leu
        275                 280                 285

Lys Lys Ala Tyr Glu Glu Val Asp Arg Val Leu Thr Asp Ala Ala Pro
    290                 295                 300

Thr Tyr Lys Gln Val Leu Glu Leu Thr Tyr Ile Arg Met Ile Leu Asn
305                 310                 315                 320

Glu Ser Leu Arg Leu Trp Pro Thr Ala Pro Ala Phe Ser Leu Tyr Pro
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460
```

<210> SEQ ID NO 17
<211> LENGTH: 463
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 17

Thr Ile Lys Glu Met Pro Gln Pro Lys Thr Phe Gly Glu Leu Lys Asn

-continued

```
        1               5                  10                 15
Leu Pro Leu Leu Asn Thr Asp Lys Pro Val Gln Ala Leu Met Lys Ile
                 20                  25                  30

Ala Asp Glu Leu Gly Glu Ile Phe Lys Phe His Thr Pro Ala Gly Thr
             35                  40                  45

Thr Ile Val Val Ser Gly His Glu Leu Val Lys Glu Val Cys Asp Glu
         50                  55                  60

Glu Arg Phe Asp Lys Ser Ile Glu Gly Ala Leu Glu Lys Val Arg Ala
 65                  70                  75                  80

Phe Ser Gly Asp Gly Leu Ala Thr Ser Trp Thr His Glu Pro Asn Trp
                 85                  90                  95

Arg Lys Ala His Asn Ile Leu Met Pro Thr Phe Ser Gln Arg Ala Met
                100                 105                 110

Lys Asp Tyr His Glu Lys Met Val Asp Ile Ala Val Gln Leu Ile Gln
                115                 120                 125

Lys Trp Ala Arg Leu Asn Pro Asp Glu His Ile Glu Val Pro Glu Asp
            130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
                180                 185                 190

Pro Asp Asp Pro Ala Tyr Asp Glu Asn Lys Arg Gln Phe Gln Glu Asp
                195                 200                 205

Ile Lys Val Met Asn Asp Leu Val Asp Lys Ile Ile Ala Asp Arg Lys
            210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
            275                 280                 285

Lys Ala Ala Glu Glu Ala Ala Arg Val Leu Val Asp Pro Val Pro Ser
            290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430
```

```
Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr
450                 455                 460
```

<210> SEQ ID NO 18
<211> LENGTH: 463
<212> TYPE: PRT
<213> ORGANISM: Artificial Sequence
<220> FEATURE:
<223> OTHER INFORMATION: Chimeric Cytochrome P450 heme group sequence
      from Bacillus megaterium and Bacillus subtilis

<400> SEQUENCE: 18

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Ala Gly Thr
         35                  40                  45

Thr Ile Val Val Ser Gly His Glu Leu Val Lys Glu Val Cys Asp Glu
     50                  55                  60

Glu Arg Phe Asp Lys Ser Ile Glu Gly Ala Leu Lys Phe Val Arg Asp
 65                  70                  75                  80

Phe Ala Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335
```

```
Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr
        450                 455                 460

<210> SEQ ID NO 19
<211> LENGTH: 1401
<212> TYPE: DNA
<213> ORGANISM: Bacillus subtilis

<400> SEQUENCE: 19
```

| | | | | | |
|---|---|---|---|---|---|
| atgaaacagg | caagcgcaat | acctcagccc | aaaacatacg | gacctttaaa | aaatcttccg       60 |
| catctggaaa | agaacagct  | ttctcaatcc | ttatggcgga | tagctgatga | attgggaccg     120 |
| attttccgtt | ttgattttcc | gggagtatcc | agtgtttttg | tgtccggcca | caatcttgtg     180 |
| gctgaagtgt | gtgatgaaaa | acgctttgac | aagaaccttg | gcaaaggctt | gcaaaggtg      240 |
| cgtgagttcg | ggggagatgg | cttagccact | agttggacgc | acgaaccgaa | ctggcaaaaa     300 |
| gcccaccgca | ttttgctgcc | gagttttagt | caaaaagcga | tgaaaggcta | tcattctatg     360 |
| atgctggata | tcgcaaccca | gctgattcaa | aagtggagcc | ggttaaaccc | taatgaagaa     420 |
| attgatgtag | cggacgatat | gacacgtctg | acgcttgata | cgattgggtt | atgcgggttt     480 |
| aactatcgat | tcaacagctt | ttaccgtgat | tcacagcatc | cgtttatcac | cagtatgctc     540 |
| cgtgccttaa | aagaggcgat | gaatcaatcg | aaaagactgg | gcctgcaaga | taaaatgatg     600 |
| gtgaaaacga | agctgcagtt | ccaaaaggat | atagaagtca | tgaactccct | ggttgataga     660 |
| atgatagcgg | agcgaaaggc | gaatccggat | gaaaacatta | aggatctctt | gtctctcatg     720 |
| ctttatgcca | aagatccagt | aacgggtgaa | acgctggatg | acgaaaacat | tcgataccaa     780 |
| atcatcacat | ttttaattgc | tggacatgag | acaacaagcg | ggttgctatc | ctttgcgatt     840 |
| tattgtctgc | ttacacatcc | ggaaaaactg | aaaaaagctc | aggaggaagc | ggatcgcgtg     900 |
| ttaacggatg | acacgcctga | atataaacaa | atccagcagc | tcaaatacat | tcggatggtt     960 |
| ttaaatgaaa | ccctcagact | gtatccaaca | gctccggctt | tttctctata | tgcgaaggag    1020 |
| gatactgttc | taggcgggga | atatccgatc | agcaaggggc | agccagtcac | tgttttaatt    1080 |
| ccaaaactgc | accgggatca | aaacgcttgg | ggaccggatg | cggaagattt | ccgtccggaa    1140 |
| cggtttgaag | atccttcaag | tatccctcac | catgcgtata | agccgtttgg | aaacggacag    1200 |
| cgcgcttgta | ttggcatgca | gtttgctctt | caagaagcga | caatggttct | cggtcttgta    1260 |
| ttaaagcatt | ttgaattgat | aaaccatact | ggctacgaac | taaaaatcaa | agaagcatta    1320 |
| acgatcaagc | cggatgattt | taaaattact | gtgaaaccgc | gaaaaacagc | ggcaatcaat    1380 |
| gtacagagaa | aagaacaggc | a                                                1401 |

<210> SEQ ID NO 20
<211> LENGTH: 466
<212> TYPE: PRT
<213> ORGANISM: Bacillus subtilis

<400> SEQUENCE: 20

```
Lys Gln Ala Ser Ala Ile Pro Gln Pro Lys Thr Tyr Gly Pro Leu Lys
  1               5                  10                  15

Asn Leu Pro His Leu Glu Lys Glu Gln Leu Ser Gln Ser Leu Trp Arg
             20                  25                  30

Ile Ala Asp Glu Leu Gly Pro Ile Phe Arg Phe Asp Phe Pro Gly Val
         35                  40                  45

Ser Ser Val Phe Val Ser Gly His Asn Leu Val Ala Glu Val Cys Asp
 50                  55                  60

Glu Lys Arg Phe Asp Lys Asn Leu Gly Lys Gly Leu Gln Lys Val Arg
 65                  70                  75                  80

Glu Phe Gly Gly Asp Gly Leu Ala Thr Ser Trp Thr His Glu Pro Asn
                 85                  90                  95

Trp Gln Lys Ala His Arg Ile Leu Leu Pro Ser Phe Ser Gln Lys Ala
            100                 105                 110

Met Lys Gly Tyr His Ser Met Met Leu Asp Ile Ala Thr Gln Leu Ile
        115                 120                 125

Gln Lys Trp Ser Arg Leu Asn Pro Asn Glu Glu Ile Asp Val Ala Asp
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Ser Gln His Pro Phe Ile Thr
                165                 170                 175

Ser Met Leu Arg Ala Leu Lys Glu Ala Met Asn Gln Ser Lys Arg Leu
            180                 185                 190

Gly Leu Gln Asp Lys Met Met Val Lys Thr Lys Leu Gln Phe Gln Lys
        195                 200                 205

Asp Ile Glu Val Met Asn Ser Leu Val Asp Arg Met Ile Ala Glu Arg
    210                 215                 220

Lys Ala Asn Pro Asp Glu Asn Ile Lys Asp Leu Leu Ser Leu Met Leu
225                 230                 235                 240

Tyr Ala Lys Asp Pro Val Thr Gly Glu Thr Leu Asp Asp Glu Asn Ile
                245                 250                 255

Arg Tyr Gln Ile Ile Thr Phe Leu Ile Ala Gly His Glu Thr Thr Ser
            260                 265                 270

Gly Leu Leu Ser Phe Ala Ile Tyr Cys Leu Leu Thr His Pro Glu Lys
        275                 280                 285

Leu Lys Lys Ala Gln Glu Glu Ala Asp Arg Val Leu Thr Asp Asp Thr
    290                 295                 300

Pro Glu Tyr Lys Gln Ile Gln Gln Leu Lys Tyr Ile Arg Met Val Leu
305                 310                 315                 320

Asn Glu Thr Leu Arg Leu Tyr Pro Thr Ala Pro Ala Phe Ser Leu Tyr
                325                 330                 335

Ala Lys Glu Asp Thr Val Leu Gly Gly Glu Tyr Pro Ile Ser Lys Gly
            340                 345                 350

Gln Pro Val Thr Val Leu Ile Pro Lys Leu His Arg Asp Gln Asn Ala
        355                 360                 365

Trp Gly Pro Asp Ala Glu Asp Phe Arg Pro Glu Arg Phe Glu Asp Pro
    370                 375                 380
```

```
Ser Ser Ile Pro His His Ala Tyr Lys Pro Phe Gly Asn Gly Gln Arg
385                 390                 395                 400

Ala Cys Ile Gly Met Gln Phe Ala Leu Gln Glu Ala Thr Met Val Leu
            405                 410                 415

Gly Leu Val Leu Lys His Phe Glu Leu Ile Asn His Thr Gly Tyr Glu
        420                 425                 430

Leu Lys Ile Lys Glu Ala Leu Thr Ile Lys Pro Asp Asp Phe Lys Ile
    435                 440                 445

Thr Val Lys Pro Arg Lys Thr Ala Ala Ile Asn Val Gln Arg Lys Glu
450                 455                 460

Gln Ala
465

<210> SEQ ID NO 21
<211> LENGTH: 33
<212> TYPE: DNA
<213> ORGANISM: Artificial Sequence
<220> FEATURE:
<223> OTHER INFORMATION: Synthetic oligonucleotide tag sequence

<400> SEQUENCE: 21
gaatgaagta ctacctgtcc tccgctagct gaa                                33

<210> SEQ ID NO 22
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 22
ggaggtacca gatctatcga tgcttaggag gtcatatg                           38

<210> SEQ ID NO 23
<211> LENGTH: 50
<212> TYPE: DNA
<213> ORGANISM: Artificial Sequence
<220> FEATURE:
<223> OTHER INFORMATION: Synthetic oligonucleotide primer sequence

<400> SEQUENCE: 23
gtactacctg tcctccgcta gctgaatcac gctttgataa aaacttaagt              50

<210> SEQ ID NO 24
<211> LENGTH: 49
<212> TYPE: DNA
<213> ORGANISM: Artificial Sequence
<220> FEATURE:
<223> OTHER INFORMATION: Synthetic oligonucleotide primer sequence

<400> SEQUENCE: 24
agcggaggac aggtagtact tcattcatcg catgcttctt taattagac               49

<210> SEQ ID NO 25
<211> LENGTH: 48
<212> TYPE: DNA
<213> ORGANISM: Artificial Sequence
<220> FEATURE:
<223> OTHER INFORMATION: Synthetic oligonucleotide primer sequence

<400> SEQUENCE: 25
gtactacctg tcctccgcta gctgaagaac ggtttgataa aagcattg                48

<210> SEQ ID NO 26
```

```
<211> LENGTH: 46
<212> TYPE: DNA
<213> ORGANISM: Artificial Sequence
<220> FEATURE:
<223> OTHER INFORMATION: Synthetic oligonucleotide primer sequence

<400> SEQUENCE: 26
agcggaggac aggtagtact tcattcatca caaacctctt tcacca                46

<210> SEQ ID NO 27
<211> LENGTH: 46
<212> TYPE: DNA
<213> ORGANISM: Artificial Sequence
<220> FEATURE:
<223> OTHER INFORMATION: Synthetic oligonucleotide primer sequence

<400> SEQUENCE: 27
gtactacctg tcctccgcta gctgaaaaac gctttgacaa gaacct                46

<210> SEQ ID NO 28
<211> LENGTH: 44
<212> TYPE: DNA
<213> ORGANISM: Artificial Sequence
<220> FEATURE:
<223> OTHER INFORMATION: Synthetic oligonucleotide primer sequence

<400> SEQUENCE: 28
agcggaggac aggtagtact tcattcatca cacacttcag ccac                  44

<210> SEQ ID NO 29
<211> LENGTH: 33
<212> TYPE: DNA
<213> ORGANISM: Artificial Sequence
<220> FEATURE:
<223> OTHER INFORMATION: Synthetic oligonucleotide tag sequence

<400> SEQUENCE: 29
atctaaaggc ctacatactc tccgctagca atc                              33

<210> SEQ ID NO 30
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 30
ggcctacata ctctccgcta gcaatcgccg tgcagcttgt tc                    42

<210> SEQ ID NO 31
<211> LENGTH: 46
<212> TYPE: DNA
<213> ORGANISM: Artificial Sequence
<220> FEATURE:
<223> OTHER INFORMATION: Synthetic oligonucleotide primer sequence

<400> SEQUENCE: 31
agcggagagt atgtaggcct ttagatatcg accatcatcg catgat                46

<210> SEQ ID NO 32
<211> LENGTH: 49
<212> TYPE: DNA
<213> ORGANISM: Artificial Sequence
<220> FEATURE:
<223> OTHER INFORMATION: Synthetic oligonucleotide primer sequence

<400> SEQUENCE: 32
```

```
ggcctacata ctctccgcta gcaatcgctg ttcagctcat tcaaaaatg            49

<210> SEQ ID NO 33
<211> LENGTH: 50
<212> TYPE: DNA
<213> ORGANISM: Artificial Sequence
<220> FEATURE:
<223> OTHER INFORMATION: Synthetic oligonucleotide primer sequence

<400> SEQUENCE: 33
agcggagagt atgtaggcct ttagatatcg accattttct catgatagtc           50

<210> SEQ ID NO 34
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 34
ggcctacata ctctccgcta gcaatcgcaa cccagctgat tc                   42

<210> SEQ ID NO 35
<211> LENGTH: 49
<212> TYPE: DNA
<213> ORGANISM: Artificial Sequence
<220> FEATURE:
<223> OTHER INFORMATION: Synthetic oligonucleotide primer sequence

<400> SEQUENCE: 35
agcggagagt atgtaggcct ttagatatcc agcatcatag aatgatagc            49

<210> SEQ ID NO 36
<211> LENGTH: 33
<212> TYPE: DNA
<213> ORGANISM: Artificial Sequence
<220> FEATURE:
<223> OTHER INFORMATION: Synthetic oligonucleotide tag sequence

<400> SEQUENCE: 36
tactgatcgc gaacaattac tccgctagct tac                             33

<210> SEQ ID NO 37
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 37
cgcgaacaat tactccgcta gcttaccgag atcagcctca tcc                  43

<210> SEQ ID NO 38
<211> LENGTH: 50
<212> TYPE: DNA
<213> ORGANISM: Artificial Sequence
<220> FEATURE:
<223> OTHER INFORMATION: Synthetic oligonucleotide primer sequence

<400> SEQUENCE: 38
agcggagtaa ttgttcgcga tcagtaaaag ctgttaaagc gatagttaaa           50

<210> SEQ ID NO 39
<211> LENGTH: 42
<212> TYPE: DNA
<213> ORGANISM: Artificial Sequence
<220> FEATURE:
```

<223> OTHER INFORMATION: Synthetic oligonucleotide primer sequence

<400> SEQUENCE: 39
cgcgaacaat tactccgcta gcttacagag aaacgcccca cc        42

<210> SEQ ID NO 40
<211> LENGTH: 50
<212> TYPE: DNA
<213> ORGANISM: Artificial Sequence
<220> FEATURE:
<223> OTHER INFORMATION: Synthetic oligonucleotide primer sequence

<400> SEQUENCE: 40
agcggagtaa ttgttcgcga tcagtagtaa ctgttaaagc ggtagttaaa        50

<210> SEQ ID NO 41
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 41
cgcgaacaat tactccgcta gcttaccgtg attcacagca tcc        43

<210> SEQ ID NO 42
<211> LENGTH: 50
<212> TYPE: DNA
<213> ORGANISM: Artificial Sequence
<220> FEATURE:
<223> OTHER INFORMATION: Synthetic oligonucleotide primer sequence

<400> SEQUENCE: 42
agcggagtaa ttgttcgcga tcagtaaaag ctgttgaatc gatagttaaa        50

<210> SEQ ID NO 43
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 43
cgaggtaccg tcgacaaaat tattgcagat cgcaaagc        38

<210> SEQ ID NO 44
<211> LENGTH: 34
<212> TYPE: DNA
<213> ORGANISM: Artificial Sequence
<220> FEATURE:
<223> OTHER INFORMATION: Synthetic oligonucleotide primer sequence

<400> SEQUENCE: 44
ccgctcgagg tcgactaggt cgttcatcac cttg        34

<210> SEQ ID NO 45
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 45
cgaggtaccg tcgacagcat tattgcagag        30

<210> SEQ ID NO 46

```
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 46
ccgctcgagg tcgactaacg aaaacatcgt ttg                              33

<210> SEQ ID NO 47
<211> LENGTH: 36
<212> TYPE: DNA
<213> ORGANISM: Artificial Sequence
<220> FEATURE:
<223> OTHER INFORMATION: Synthetic oligonucleotide primer sequence

<400> SEQUENCE: 47
cgaggtaccg tcgacagaat gatagcggag cgaaag                           36

<210> SEQ ID NO 48
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 48
ccgctcgagg tcgaccaggg agttcatgac ttc                              33

<210> SEQ ID NO 49
<211> LENGTH: 33
<212> TYPE: DNA
<213> ORGANISM: Artificial Sequence
<220> FEATURE:
<223> OTHER INFORMATION: Synthetic oligonucleotide tag sequence

<400> SEQUENCE: 49
acatgaacgc gtacttattc tccgctagct aca                              33

<210> SEQ ID NO 50
<211> LENGTH: 49
<212> TYPE: DNA
<213> ORGANISM: Artificial Sequence
<220> FEATURE:
<223> OTHER INFORMATION: Synthetic oligonucleotide primer sequence

<400> SEQUENCE: 50
cgcgtactta ttctccgcta gctacaacaa gtggtctttt atcatttgc             49

<210> SEQ ID NO 51
<211> LENGTH: 45
<212> TYPE: DNA
<213> ORGANISM: Artificial Sequence
<220> FEATURE:
<223> OTHER INFORMATION: Synthetic oligonucleotide primer sequence

<400> SEQUENCE: 51
agcggagaat aagtacgcgt tcatgtttcg tgtcccgcaa ttaag                 45

<210> SEQ ID NO 52
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 52
```

```
cgcgtactta ttctccgcta gctacaacga gcggcctgct tt                    42
```

<210> SEQ ID NO 53
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 53

```
agcggagaat aagtacgcgt tcatgtttca tggccggcaa tc                    42
```

<210> SEQ ID NO 54
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 54

```
cgcgtactta ttctccgcta gctacaacaa gcgggttgct atc                   43
```

<210> SEQ ID NO 55
<211> LENGTH: 49
<212> TYPE: DNA
<213> ORGANISM: Artificial Sequence
<220> FEATURE:
<223> OTHER INFORMATION: Synthetic oligonucleotide primer sequence

<400> SEQUENCE: 55

```
agcggagaat aagtacgcgt tcatgtctca tgtccagcaa ttaaaaatg             49
```

<210> SEQ ID NO 56
<211> LENGTH: 33
<212> TYPE: DNA
<213> ORGANISM: Artificial Sequence
<220> FEATURE:
<223> OTHER INFORMATION: Synthetic oligonucleotide tag sequence

<400> SEQUENCE: 56

```
gcttaagtat acaccatccc tccgctagca gct                              33
```

<210> SEQ ID NO 57
<211> LENGTH: 45
<212> TYPE: DNA
<213> ORGANISM: Artificial Sequence
<220> FEATURE:
<223> OTHER INFORMATION: Synthetic oligonucleotide primer sequence

<400> SEQUENCE: 57

```
tatacaccat ccctccgcta gcagctcctg cgttttccct atatg                 45
```

<210> SEQ ID NO 58
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 58

```
agcggaggga tggtgtatac ttaagcagtt ggccataagc gc                    42
```

<210> SEQ ID NO 59
<211> LENGTH: 45
<212> TYPE: DNA
<213> ORGANISM: Artificial Sequence
<220> FEATURE:

<223> OTHER INFORMATION: Synthetic oligonucleotide primer sequence

<400> SEQUENCE: 59
tatacaccat ccctccgcta gcagctccgg ctttcagcct ttatc         45

<210> SEQ ID NO 60
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 60
agcggaggga tggtgtatac ttaagctgtc ggccataagc gc            42

<210> SEQ ID NO 61
<211> LENGTH: 46
<212> TYPE: DNA
<213> ORGANISM: Artificial Sequence
<220> FEATURE:
<223> OTHER INFORMATION: Synthetic oligonucleotide primer sequence

<400> SEQUENCE: 61
tatacaccat ccctccgcta gcagctccgg ctttttctct atatgc        46

<210> SEQ ID NO 62
<211> LENGTH: 45
<212> TYPE: DNA
<213> ORGANISM: Artificial Sequence
<220> FEATURE:
<223> OTHER INFORMATION: Synthetic oligonucleotide primer sequence

<400> SEQUENCE: 62
agcggaggga tggtgtatac ttaagctgtt ggatacagtc tgagg         45

<210> SEQ ID NO 63
<211> LENGTH: 33
<212> TYPE: DNA
<213> ORGANISM: Artificial Sequence
<220> FEATURE:
<223> OTHER INFORMATION: Synthetic oligonucleotide tag sequence

<400> SEQUENCE: 63
cagtgattcg aaaccattac tccgctagct cag                      33

<210> SEQ ID NO 64
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 64
tcgaaaccat tactccgcta gctcagttcg ctcttcatga agc           43

<210> SEQ ID NO 65
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 65
agcggagtaa tggtttcgaa tcactgctga ccgatacacg cac           43

<210> SEQ ID NO 66

```
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 66
tcgaaaccat tactccgcta gctcagtttg cccttcatga agc                    43

<210> SEQ ID NO 67
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 67
agcggagtaa tggtttcgaa tcactgcatg ccgatacagg cc                     42

<210> SEQ ID NO 68
<211> LENGTH: 44
<212> TYPE: DNA
<213> ORGANISM: Artificial Sequence
<220> FEATURE:
<223> OTHER INFORMATION: Synthetic oligonucleotide primer sequence

<400> SEQUENCE: 68
tcgaaaccat tactccgcta gctcagtttg ctcttcaaga agcg                   44

<210> SEQ ID NO 69
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 69
agcggagtaa tggtttcgaa tcactgcatg ccaatacaag cgc                    43

<210> SEQ ID NO 70
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 70
caacaattgt taagtgctag gtgaaggaat acc                               33

<210> SEQ ID NO 71
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 71
caacaattgt tattcagctg cctggacgtc                                   30

<210> SEQ ID NO 72
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 72
```

-continued

```
caacaattgt tatgcctgtt cttttctctg tac                                     33
```

<210> SEQ ID NO 73
<211> LENGTH: 34
<212> TYPE: DNA
<213> ORGANISM: Artificial Sequence
<220> FEATURE:
<223> OTHER INFORMATION: Synthetic oligonucleotide primer sequence

<400> SEQUENCE: 73

```
ccacatcgtc accccaaatt gttttatcac ggtg                                    34
```

<210> SEQ ID NO 74
<211> LENGTH: 31
<212> TYPE: DNA
<213> ORGANISM: Artificial Sequence
<220> FEATURE:
<223> OTHER INFORMATION: Synthetic oligonucleotide primer sequence

<400> SEQUENCE: 74

```
caatttgggg tgacgatgtg gaagagttcc g                                       31
```

<210> SEQ ID NO 75
<211> LENGTH: 466
<212> TYPE: PRT
<213> ORGANISM: Artificial Sequence
<220> FEATURE:
<223> OTHER INFORMATION: Chimeric Cytochrome P450 heme group polypeptide
      sequence from CYP102A1 (Bacillus megaterium);
      CYP102A2 (Bacillus subtilis) and CYP102A3
      (Bacillus subtilis)

<400> SEQUENCE: 75

Lys Gln Ala Ser Ala Ile Pro Gln Pro Lys Thr Tyr Gly Pro Leu Lys
 1               5                  10                  15

Asn Leu Pro His Leu Glu Lys Glu Gln Leu Ser Gln Ser Leu Trp Arg
             20                  25                  30

Ile Ala Asp Glu Leu Gly Pro Ile Phe Arg Phe Asp Phe Pro Gly Val
         35                  40                  45

Ser Ser Val Phe Val Ser Gly His Asn Leu Val Ala Glu Val Cys Asp
     50                  55                  60

Glu Glu Arg Phe Asp Lys Ser Ile Glu Gly Ala Leu Glu Lys Val Arg
 65                  70                  75                  80

Ala Phe Ser Gly Asp Gly Leu Ala Thr Ser Trp Thr His Glu Pro Asn
                 85                  90                  95

Trp Arg Lys Ala His Asn Ile Leu Met Pro Thr Phe Ser Gln Arg Ala
            100                 105                 110

Met Lys Asp Tyr His Glu Lys Met Val Asp Ile Ala Thr Gln Leu Ile
        115                 120                 125

Gln Lys Trp Ser Arg Leu Asn Pro Asn Glu Glu Ile Asp Val Ala Asp
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Arg Met Ile Ala Glu Arg
    210                 215                 220

```
Lys Ala Asn Pro Asp Glu Asn Ile Lys Asp Leu Leu Ser Leu Met Leu
225                 230                 235                 240

Tyr Ala Lys Asp Pro Val Thr Gly Glu Thr Leu Asp Asp Glu Asn Ile
            245                 250                 255

Arg Tyr Gln Ile Ile Thr Phe Leu Ile Ala Gly His Glu Thr Thr Ser
                260                 265                 270

Gly Leu Leu Ser Phe Ala Thr Tyr Phe Leu Leu Lys His Pro Asp Lys
        275                 280                 285

Leu Lys Lys Ala Tyr Glu Glu Val Asp Arg Val Leu Thr Asp Ala Ala
    290                 295                 300

Pro Thr Tyr Lys Gln Val Leu Glu Leu Thr Tyr Ile Arg Met Ile Leu
305                 310                 315                 320

Asn Glu Ser Leu Arg Leu Trp Pro Thr Ala Pro Ala Phe Ser Leu Tyr
                325                 330                 335

Ala Lys Glu Asp Thr Val Leu Gly Gly Glu Tyr Pro Ile Ser Lys Gly
                340                 345                 350

Gln Pro Val Thr Val Leu Ile Pro Lys Leu His Arg Asp Gln Asn Ala
            355                 360                 365

Trp Gly Pro Asp Ala Glu Asp Phe Arg Pro Glu Arg Phe Glu Asp Pro
        370                 375                 380

Ser Ser Ile Pro His His Ala Tyr Lys Pro Phe Gly Asn Gly Gln Arg
385                 390                 395                 400

Ala Cys Ile Gly Met Gln Phe Ala Leu Gln Glu Ala Thr Met Val Leu
                405                 410                 415

Gly Leu Val Leu Lys His Phe Glu Leu Ile Asn His Thr Gly Tyr Glu
                420                 425                 430

Leu Lys Ile Lys Glu Ala Leu Thr Ile Lys Pro Asp Asp Phe Lys Ile
            435                 440                 445

Thr Val Lys Pro Arg Lys Thr Ala Ala Ile Asn Val Gln Arg Lys Glu
            450                 455                 460

Gln Ala
465

<210> SEQ ID NO 76
<211> LENGTH: 466
<212> TYPE: PRT
<213> ORGANISM: Artificial Sequence
<220> FEATURE:
<223> OTHER INFORMATION: Chimeric Cytochrome P450 heme group polypeptide
      sequence from CYP102A1 (Bacillus megaterium);
      CYP102A2 (Bacillus subtilis) and CYP102A3
      (Bacillus subtilis)

<400> SEQUENCE: 76

Lys Gln Ala Ser Ala Ile Pro Gln Pro Lys Thr Tyr Gly Pro Leu Lys
1               5                   10                  15

Asn Leu Pro His Leu Glu Lys Glu Gln Leu Ser Gln Ser Leu Trp Arg
                20                  25                  30

Ile Ala Asp Glu Leu Gly Pro Ile Phe Arg Phe Asp Phe Pro Gly Val
            35                  40                  45

Ser Ser Val Phe Val Ser Gly His Asn Leu Val Ala Glu Val Cys Asp
    50                  55                  60

Glu Lys Arg Phe Asp Lys Asn Leu Gly Lys Gly Leu Gln Lys Val Arg
65                  70                  75                  80

Glu Phe Gly Gly Asp Gly Leu Ala Thr Ser Trp Thr His Glu Pro Asn
                85                  90                  95
```

```
Trp Gln Lys Ala His Arg Ile Leu Leu Pro Ser Phe Ser Gln Lys Ala
                100                 105                 110
Met Lys Gly Tyr His Ser Met Met Leu Asp Ile Ala Val Gln Leu Ile
            115                 120                 125
Gln Lys Trp Ala Arg Leu Asn Pro Asn Glu Ala Val Asp Val Pro Gly
130                 135                 140
Asp Met Thr Arg Leu Thr Leu Asp Thr Ile Gly Leu Cys Gly Phe Asn
145                 150                 155                 160
Tyr Arg Phe Asn Ser Tyr Tyr Arg Asp Gln Pro His Pro Phe Ile Thr
                165                 170                 175
Ser Met Val Arg Ala Leu Asp Glu Ala Met Asn Lys Leu Gln Arg Ala
            180                 185                 190
Asn Pro Asp Asp Pro Ala Tyr Asp Glu Asn Lys Arg Gln Phe Gln Glu
        195                 200                 205
Asp Ile Lys Val Met Asn Asp Leu Val Asp Ser Ile Ile Ala Glu Arg
210                 215                 220
Arg Ala Asn Gly Asp Gln Asp Glu Lys Asp Leu Leu Ala Arg Met Leu
225                 230                 235                 240
Asn Val Glu Asp Pro Glu Thr Gly Glu Lys Leu Asp Asp Glu Asn Ile
                245                 250                 255
Arg Phe Gln Ile Ile Thr Phe Leu Ile Ala Gly His Glu Thr Thr Ser
            260                 265                 270
Gly Leu Leu Ser Phe Ala Thr Tyr Phe Leu Leu Lys His Pro Asp Lys
        275                 280                 285
Leu Lys Lys Ala Tyr Glu Glu Val Asp Arg Val Leu Thr Asp Ala Ala
290                 295                 300
Pro Thr Tyr Lys Gln Val Leu Glu Leu Thr Tyr Ile Arg Met Ile Leu
305                 310                 315                 320
Asn Glu Ser Leu Arg Leu Trp Pro Thr Ala Pro Ala Phe Ser Leu Tyr
                325                 330                 335
Ala Lys Glu Asp Thr Val Leu Gly Gly Glu Tyr Pro Leu Glu Lys Gly
            340                 345                 350
Asp Glu Leu Met Val Leu Ile Pro Gln Leu His Arg Asp Lys Thr Ile
        355                 360                 365
Trp Gly Asp Asp Val Glu Glu Phe Arg Pro Glu Arg Phe Glu Asn Pro
370                 375                 380
Ser Ala Ile Pro Gln His Ala Phe Lys Pro Phe Gly Asn Gly Gln Arg
385                 390                 395                 400
Ala Cys Ile Gly Gln Gln Phe Ala Leu Gln Glu Ala Thr Met Val Leu
                405                 410                 415
Gly Leu Val Leu Lys His Phe Glu Leu Ile Asn His Thr Gly Tyr Glu
            420                 425                 430
Leu Lys Ile Lys Glu Ala Leu Thr Ile Lys Pro Asp Asp Phe Lys Ile
        435                 440                 445
Thr Val Lys Pro Arg Lys Thr Ala Ala Ile Asn Val Gln Arg Lys Glu
450                 455                 460
Gln Ala
465

<210> SEQ ID NO 77
<211> LENGTH: 466
<212> TYPE: PRT
<213> ORGANISM: Artificial Sequence
<220> FEATURE:
<223> OTHER INFORMATION: Chimeric Cytochrome P450 heme group polypeptide
      sequence from CYP102A1 (Bacillus megaterium);
```

CYP102A2 (Bacillus subtilis) and CYP102A3
(Bacillus subtilis)

<400> SEQUENCE: 77

```
Lys Gln Ala Ser Ala Ile Pro Gln Pro Lys Thr Tyr Gly Pro Leu Lys
1               5                   10                  15

Asn Leu Pro His Leu Glu Lys Glu Gln Leu Ser Gln Ser Leu Trp Arg
            20                  25                  30

Ile Ala Asp Glu Leu Gly Pro Ile Phe Arg Phe Asp Phe Pro Gly Val
        35                  40                  45

Ser Ser Val Phe Val Ser Gly His Asn Leu Val Ala Glu Val Cys Asp
    50                  55                  60

Glu Glu Arg Phe Asp Lys Ser Ile Glu Gly Ala Leu Glu Lys Val Arg
65                  70                  75                  80

Ala Phe Ser Gly Asp Gly Leu Ala Thr Ser Trp Thr His Glu Pro Asn
                85                  90                  95

Trp Arg Lys Ala His Asn Ile Leu Met Pro Thr Phe Ser Gln Arg Ala
            100                 105                 110

Met Lys Asp Tyr His Glu Lys Met Val Asp Ile Ala Thr Gln Leu Ile
        115                 120                 125

Gln Lys Trp Ser Arg Leu Asn Pro Asn Glu Glu Ile Asp Val Ala Asp
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Arg Met Ile Ala Glu Arg
    210                 215                 220

Lys Ala Asn Pro Asp Glu Asn Ile Lys Asp Leu Leu Ser Leu Met Leu
225                 230                 235                 240

Tyr Ala Lys Asp Pro Val Thr Gly Glu Thr Leu Asp Asp Glu Asn Ile
                245                 250                 255

Arg Tyr Gln Ile Ile Thr Phe Leu Ile Ala Gly His Glu Thr Thr Ser
            260                 265                 270

Gly Leu Leu Ser Phe Ala Ile Tyr Cys Leu Leu Thr His Pro Glu Lys
        275                 280                 285

Leu Lys Lys Ala Gln Glu Glu Ala Asp Arg Val Leu Thr Asp Asp Thr
    290                 295                 300

Pro Glu Tyr Lys Gln Ile Gln Gln Leu Lys Tyr Ile Arg Met Val Leu
305                 310                 315                 320

Asn Glu Thr Leu Arg Leu Tyr Pro Thr Ala Pro Ala Phe Ser Leu Tyr
                325                 330                 335

Ala Lys Glu Asp Thr Val Leu Gly Gly Glu Tyr Pro Ile Ser Lys Gly
            340                 345                 350

Gln Pro Val Thr Val Leu Ile Pro Lys Leu His Arg Asp Gln Asn Ala
        355                 360                 365

Trp Gly Pro Asp Ala Glu Asp Phe Arg Pro Glu Arg Phe Glu Asp Pro
    370                 375                 380

Ser Ser Ile Pro His His Ala Tyr Lys Pro Phe Gly Asn Gly Gln Arg
385                 390                 395                 400
```

```
Ala Cys Ile Gly Met Gln Phe Ala Leu Gln Glu Ala Thr Met Val Leu
            405                 410                 415

Gly Leu Val Leu Lys His Phe Glu Leu Ile Asn His Thr Gly Tyr Glu
            420                 425                 430

Leu Lys Ile Lys Glu Ala Leu Thr Ile Lys Pro Asp Asp Phe Lys Ile
            435                 440                 445

Thr Val Lys Pro Arg Lys Thr Ala Ala Ile Asn Val Gln Arg Lys Glu
450                 455                 460

Gln Ala
465

<210> SEQ ID NO 78
<211> LENGTH: 465
<212> TYPE: PRT
<213> ORGANISM: Artificial Sequence
<220> FEATURE:
<223> OTHER INFORMATION: Chimeric Cytochrome P450 heme group polypeptide
      sequence from CYP102A1 (Bacillus megaterium);
      CYP102A2 (Bacillus subtilis) and CYP102A3
      (Bacillus subtilis)

<400> SEQUENCE: 78

Lys Glu Thr Ser Pro Ile Pro Gln Pro Lys Thr Phe Gly Pro Leu Gly
1               5                   10                  15

Asn Leu Pro Leu Ile Asp Lys Asp Lys Pro Thr Leu Ser Leu Ile Lys
            20                  25                  30

Leu Ala Glu Glu Gln Gly Pro Ile Phe Gln Ile His Thr Pro Ala Gly
            35                  40                  45

Thr Thr Ile Val Val Ser Gly His Glu Leu Val Lys Glu Val Cys Asp
50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ala Thr Ser Trp Thr His Glu Lys Asn
            85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
            115                 120                 125

Gln Lys Trp Ala Arg Leu Asn Pro Asn Glu Ala Val Asp Val Pro Gly
            130                 135                 140

Asp Met Thr Arg Leu Thr Leu Asp Thr Ile Gly Leu Cys Gly Phe Asn
145                 150                 155                 160

Tyr Arg Phe Asn Ser Tyr Tyr Arg Asp Ser Gln His Pro Phe Ile Thr
            165                 170                 175

Ser Met Leu Arg Ala Leu Lys Glu Ala Met Asn Gln Ser Lys Arg Leu
            180                 185                 190

Gly Leu Gln Asp Lys Met Met Val Lys Thr Lys Leu Gln Phe Gln Lys
            195                 200                 205

Asp Ile Glu Val Met Asn Ser Leu Val Asp Lys Ile Ile Ala Asp Arg
            210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
            260                 265                 270

Leu Leu Ser Phe Ala Thr Tyr Phe Leu Leu Lys His Pro Asp Lys Leu
```

```
                275                 280                 285
Lys Lys Ala Tyr Glu Glu Val Asp Arg Val Leu Thr Asp Ala Ala Pro
    290                 295                 300

Thr Tyr Lys Gln Val Leu Glu Leu Thr Tyr Ile Arg Met Ile Leu Asn
305                 310                 315                 320

Glu Ser Leu Arg Leu Trp Pro Thr Ala Pro Ala Phe Ser Leu Tyr Ala
                325                 330                 335

Lys Glu Asp Thr Val Leu Gly Gly Glu Tyr Pro Ile Ser Lys Gly Gln
            340                 345                 350

Pro Val Thr Val Leu Ile Pro Lys Leu His Arg Asp Gln Asn Ala Trp
        355                 360                 365

Gly Pro Asp Ala Glu Asp Phe Arg Pro Glu Arg Phe Glu Asp Pro Ser
370                 375                 380

Ser Ile Pro His His Ala Tyr Lys Pro Phe Gly Asn Gly Gln Arg Ala
385                 390                 395                 400

Cys Ile Gly Met Gln Phe Ala Leu Gln Glu Ala Thr Met Val Leu Gly
                405                 410                 415

Leu Val Leu Lys His Phe Glu Leu Ile Asn His Thr Gly Tyr Glu Leu
            420                 425                 430

Lys Ile Lys Glu Ala Leu Thr Ile Lys Pro Asp Asp Phe Lys Ile Thr
        435                 440                 445

Val Lys Pro Arg Lys Thr Ala Ala Ile Asn Val Gln Arg Lys Glu Gln
    450                 455                 460

Ala
465

<210> SEQ ID NO 79
<211> LENGTH: 36
<212> TYPE: DNA
<213> ORGANISM: Artificial Sequence
<220> FEATURE:
<223> OTHER INFORMATION: Synthetic oligonucleotide probe sequence

<400> SEQUENCE: 79
gacaattaaa gaaatgcctc agccaaaaac gtttgg                              36

<210> SEQ ID NO 80
<211> LENGTH: 27
<212> TYPE: DNA
<213> ORGANISM: Artificial Sequence
<220> FEATURE:
<223> OTHER INFORMATION: Synthetic oligonucleotide probe sequence

<400> SEQUENCE: 80
gaaggaaaca agcccgattc ctcagcc                                        27

<210> SEQ ID NO 81
<211> LENGTH: 27
<212> TYPE: DNA
<213> ORGANISM: Artificial Sequence
<220> FEATURE:
<223> OTHER INFORMATION: Synthetic oligonucleotide probe sequence

<400> SEQUENCE: 81
gaaacaggca agcgcaatac ctcagcc                                        27

<210> SEQ ID NO 82
<211> LENGTH: 34
<212> TYPE: DNA
<213> ORGANISM: Artificial Sequence
<220> FEATURE:
```

```
<223> OTHER INFORMATION: Synthetic oligonucleotide probe sequence

<400> SEQUENCE: 82
gcgcataata tcttacttcc aagcttcagt cagc                                   34

<210> SEQ ID NO 83
<211> LENGTH: 27
<212> TYPE: DNA
<213> ORGANISM: Artificial Sequence
<220> FEATURE:
<223> OTHER INFORMATION: Synthetic oligonucleotide probe sequence

<400> SEQUENCE: 83
gcgcacaaca ttctgatgcc gacgttc                                           27

<210> SEQ ID NO 84
<211> LENGTH: 28
<212> TYPE: DNA
<213> ORGANISM: Artificial Sequence
<220> FEATURE:
<223> OTHER INFORMATION: Synthetic oligonucleotide probe sequence

<400> SEQUENCE: 84
cccaccgcat tttgctgccg agttttag                                          28

<210> SEQ ID NO 85
<211> LENGTH: 36
<212> TYPE: DNA
<213> ORGANISM: Artificial Sequence
<220> FEATURE:
<223> OTHER INFORMATION: Synthetic oligonucleotide probe sequence

<400> SEQUENCE: 85
gagcgtctaa atgcagatga gcatattgaa gtaccg                                 36

<210> SEQ ID NO 86
<211> LENGTH: 27
<212> TYPE: DNA
<213> ORGANISM: Artificial Sequence
<220> FEATURE:
<223> OTHER INFORMATION: Synthetic oligonucleotide probe sequence

<400> SEQUENCE: 86
gcaaggctca acccgaatga agcagtc                                           27

<210> SEQ ID NO 87
<211> LENGTH: 35
<212> TYPE: DNA
<213> ORGANISM: Artificial Sequence
<220> FEATURE:
<223> OTHER INFORMATION: Synthetic oligonucleotide probe sequence

<400> SEQUENCE: 87
gagccggtta accccaatg aagaaattga tgtag                                   35

<210> SEQ ID NO 88
<211> LENGTH: 31
<212> TYPE: DNA
<213> ORGANISM: Artificial Sequence
<220> FEATURE:
<223> OTHER INFORMATION: Synthetic oligonucleotide probe sequence

<400> SEQUENCE: 88
ccagacgacc cagcttatga tgaaaacaag c                                      31

<210> SEQ ID NO 89
```

```
<211> LENGTH: 34
<212> TYPE: DNA
<213> ORGANISM: Artificial Sequence
<220> FEATURE:
<223> OTHER INFORMATION: Synthetic oligonucleotide probe sequence

<400> SEQUENCE: 89
gttcaagata agcttatggt cagaacaaag cggc                                 34

<210> SEQ ID NO 90
<211> LENGTH: 36
<212> TYPE: DNA
<213> ORGANISM: Artificial Sequence
<220> FEATURE:
<223> OTHER INFORMATION: Synthetic oligonucleotide probe sequence

<400> SEQUENCE: 90
ctgcaagata aaatgatggt gaaaacgaag ctgcag                               36

<210> SEQ ID NO 91
<211> LENGTH: 34
<212> TYPE: DNA
<213> ORGANISM: Artificial Sequence
<220> FEATURE:
<223> OTHER INFORMATION: Synthetic oligonucleotide probe sequence

<400> SEQUENCE: 91
gcaagcggtg aacaaagcga tgatttatta acgc                                 34

<210> SEQ ID NO 92
<211> LENGTH: 33
<212> TYPE: DNA
<213> ORGANISM: Artificial Sequence
<220> FEATURE:
<223> OTHER INFORMATION: Synthetic oligonucleotide probe sequence

<400> SEQUENCE: 92
gcgaatggag accaggatga aaaagatttg ctc                                  33

<210> SEQ ID NO 93
<211> LENGTH: 35
<212> TYPE: DNA
<213> ORGANISM: Artificial Sequence
<220> FEATURE:
<223> OTHER INFORMATION: Synthetic oligonucleotide probe sequence

<400> SEQUENCE: 93
gcgaatccgg atgaaaacat taaggatctc ttgtc                                35

<210> SEQ ID NO 94
<211> LENGTH: 29
<212> TYPE: DNA
<213> ORGANISM: Artificial Sequence
<220> FEATURE:
<223> OTHER INFORMATION: Synthetic oligonucleotide probe sequence

<400> SEQUENCE: 94
gcagcacgag ttctagtaga tcctgttcc                                       29

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide probe sequence

<400> SEQUENCE: 95
```

-continued gtcgatcggg tgctgacgga tgcag                                              25

<210> SEQ ID NO 96
<211> LENGTH: 26
<212> TYPE: DNA
<213> ORGANISM: Artificial Sequence
<220> FEATURE:
<223> OTHER INFORMATION: Synthetic oligonucleotide probe sequence

<400> SEQUENCE: 96
gcggatcgcg tgttaacgga tgacac                                             26

<210> SEQ ID NO 97
<211> LENGTH: 24
<212> TYPE: DNA
<213> ORGANISM: Artificial Sequence
<220> FEATURE:
<223> OTHER INFORMATION: Synthetic oligonucleotide probe sequence

<400> SEQUENCE: 97
ccaagtgcga ttccgcagca tgcg                                               24

<210> SEQ ID NO 98
<211> LENGTH: 27
<212> TYPE: DNA
<213> ORGANISM: Artificial Sequence
<220> FEATURE:
<223> OTHER INFORMATION: Synthetic oligonucleotide probe sequence

<400> SEQUENCE: 98
caggaccaag tgcctcatca tgcgtac                                            27

<210> SEQ ID NO 99
<211> LENGTH: 31
<212> TYPE: DNA
<213> ORGANISM: Artificial Sequence
<220> FEATURE:
<223> OTHER INFORMATION: Synthetic oligonucleotide probe sequence

<400> SEQUENCE: 99
ccttcaagta tccctcacca tgcgtataag c                                       31

<210> SEQ ID NO 100
<211> LENGTH: 35
<212> TYPE: DNA
<213> ORGANISM: Artificial Sequence
<220> FEATURE:
<223> OTHER INFORMATION: Synthetic oligonucleotide probe sequence

<400> SEQUENCE: 100
atcgaaaaaa attccgcttg gcggtattcc ttcac                                   35

<210> SEQ ID NO 101
<211> LENGTH: 28
<212> TYPE: DNA
<213> ORGANISM: Artificial Sequence
<220> FEATURE:
<223> OTHER INFORMATION: Synthetic oligonucleotide probe sequence

<400> SEQUENCE: 101
gccgtcatca ggaagccatt catgcaga                                           28

<210> SEQ ID NO 102
<211> LENGTH: 31
<212> TYPE: DNA
<213> ORGANISM: Artificial Sequence
<220> FEATURE:

<223> OTHER INFORMATION: Synthetic oligonucleotide probe sequence

<400> SEQUENCE: 102
cgcgaaaaac agcggcaatc aatgtacaga g    31

<210> SEQ ID NO 103
<211> LENGTH: 3147
<212> TYPE: DNA
<213> ORGANISM: Bacillus megaterium

<400> SEQUENCE: 103

| | | | | | |
|---|---|---|---|---|---|
| atgacaatta | aagaaatgcc | tcagccaaaa | acgtttggag | agcttaaaaa | tttaccgtta | 60 |
| ttaaacacag | ataaaccggt | tcaagctttg | atgaaaattg | cggatgaatt | aggagaaatc | 120 |
| tttaaattcg | aggcgcctgg | tcgtgtaacg | cgctacttat | caagtcagcg | tctaattaaa | 180 |
| gaagcatgcg | atgaatcacg | ctttgataaa | aacttaagtc | aagcgcttaa | atttgtacgt | 240 |
| gattttgcag | gagacgggtt | ggccactagt | tggacgcatg | aaaaaaattg | gaaaaaagcg | 300 |
| cataatatct | tacttccaag | cttcagtcag | caggcaatga | aaggctatca | tgcgatgatg | 360 |
| gtcgatatcg | ccgtgcagct | tgttcaaaag | tgggagcgtc | taaatgcaga | tgagcatatt | 420 |
| gaagtaccgg | aagacatgac | acgtttaacg | cttgatacaa | ttggtctttg | cggctttaac | 480 |
| tatcgcttta | acagctttta | ccgagatcag | cctcatccat | ttattacaag | tatggtccgt | 540 |
| gcactggatg | aagcaatgaa | caagctgcag | cgagcaaatc | cagacgaccc | agcttatgat | 600 |
| gaaaacaagc | gccagtttca | agaagatatc | aaggtgatga | cgacctagt | agataaaatt | 660 |
| attgcagatc | gcaaagcaag | cggtgaacaa | agcgatgatt | tattaacgca | tatgctaaac | 720 |
| ggaaaagatc | cagaaacggg | tgagccgctt | gatgacgaga | acattcgcta | tcaaattatt | 780 |
| acattcttaa | ttgcgggaca | cgaaacaaca | agtggtcttt | tatcatttgc | gctgtatttc | 840 |
| ttagtgaaaa | atccacatgt | attacaaaaa | gcagcagaag | aagcagcacg | agttctagta | 900 |
| gatcctgttc | caagctacaa | acaagtcaaa | cagcttaaat | atgtcggcat | ggtcttaaac | 960 |
| gaagcgctgc | gcttatggcc | aactgctcct | gcgttttccc | tatatgcaaa | agaagatacg | 1020 |
| gtgcttggag | gagaatatcc | tttagaaaaa | ggcgacgaac | taatggttct | gattcctcag | 1080 |
| cttcaccgtg | ataaaacaat | ttggggagac | gatgtggaag | agttccgtcc | agagcgtttt | 1140 |
| gaaaatccaa | gtgcgattcc | gcagcatgcg | tttaaaccgt | tggaaacgg | tcagcgtgcg | 1200 |
| tgtatcggtc | agcagttcgc | tcttcatgaa | gcaacgctgg | tacttggtat | gatgctaaaa | 1260 |
| cactttgact | tgaagatca | tacaaactac | gagctggata | ttaaagaaac | tttaacgtta | 1320 |
| aaacctgaag | gctttgtggt | aaaagcaaaa | tcgaaaaaaa | ttccgcttgg | cggtattcct | 1380 |
| tcacctagca | ctgaacagtc | tgctaaaaaa | gtacgcaaaa | aggcagaaaa | cgctcataat | 1440 |
| acgccgctgc | ttgtgctata | cggttcaaat | atgggaacag | ctgaaggaac | ggcgcgtgat | 1500 |
| ttagcagata | ttgcaatgag | caaaggattt | gcaccgcagg | tcgcaacgct | tgattcacac | 1560 |
| gccggaaatc | ttccgcgcga | aggagctgta | ttaattgtaa | cggcgtctta | taacggtcat | 1620 |
| ccgcctgata | acgcaaagca | atttgtcgac | tggttagacc | aagcgtctgc | tgatgaagta | 1680 |
| aaaggcgttc | gctactccgt | atttggatgc | ggcgataaaa | actgggctac | tacgtatcaa | 1740 |
| aaagtgcctg | cttttatcga | tgaaacgctt | gccgctaaag | ggcagaaaaa | catcgctgac | 1800 |
| cgcggtgaag | cagatgcaag | cgacgacttt | gaaggcacat | atgaagaatg | gcgtgaacat | 1860 |
| atgtggagtg | acgtagcagc | ctactttaac | ctcgacattg | aaaacagtga | agataataaa | 1920 |
| tctactcttt | cacttcaatt | tgtcgacagc | gccgcggata | tgccgcttgc | gaaaatgcac | 1980 |

-continued

```
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctggg                                        3147
```

<210> SEQ ID NO 104
<211> LENGTH: 1047
<212> TYPE: PRT
<213> ORGANISM: Bacillus megaterium

<400> SEQUENCE: 104

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Val Arg Asp
 65                  70                  75                  80

Phe Ala Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175
```

```
Met Val Arg Ala Leu Asp Glu Ala Met Asn Lys Leu Gln Arg Ala Asn
            180                 185                 190

Pro Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
            245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
```

-continued

```
                595                 600                 605
    Phe Glu Gly Thr Tyr Glu Glu Trp Arg Glu His Met Trp Ser Asp Val
            610                 615                 620
    Ala Ala Tyr Phe Asn Leu Asp Ile Glu Asn Ser Glu Asp Asn Lys Ser
    625                 630                 635                 640
    Thr Leu Ser Leu Gln Phe Val Asp Ser Ala Ala Asp Met Pro Leu Ala
                    645                 650                 655
    Lys Met His Gly Ala Phe Ser Thr Asn Val Val Ala Ser Lys Glu Leu
                660                 665                 670
    Gln Gln Pro Gly Ser Ala Arg Ser Thr Arg His Leu Glu Ile Glu Leu
                675                 680                 685
    Pro Lys Glu Ala Ser Tyr Gln Glu Gly Asp His Leu Gly Val Ile Pro
            690                 695                 700
    Arg Asn Tyr Glu Gly Ile Val Asn Arg Val Thr Ala Arg Phe Gly Leu
    705                 710                 715                 720
    Asp Ala Ser Gln Gln Ile Arg Leu Glu Ala Glu Glu Lys Leu Ala
                    725                 730                 735
    His Leu Pro Leu Ala Lys Thr Val Ser Val Glu Glu Leu Leu Gln Tyr
                740                 745                 750
    Val Glu Leu Gln Asp Pro Val Thr Arg Thr Gln Leu Arg Ala Met Ala
                755                 760                 765
    Ala Lys Thr Val Cys Pro Pro His Lys Val Glu Leu Glu Ala Leu Leu
            770                 775                 780
    Glu Lys Gln Ala Tyr Lys Glu Gln Val Leu Ala Lys Arg Leu Thr Met
    785                 790                 795                 800
    Leu Glu Leu Leu Glu Lys Tyr Pro Ala Cys Glu Met Lys Phe Ser Glu
                    805                 810                 815
    Phe Ile Ala Leu Leu Pro Ser Ile Arg Pro Arg Tyr Tyr Ser Ile Ser
                820                 825                 830
    Ser Ser Pro Arg Val Asp Glu Lys Gln Ala Ser Ile Thr Val Ser Val
                835                 840                 845
    Val Ser Gly Glu Ala Trp Ser Gly Tyr Gly Glu Tyr Lys Gly Ile Ala
            850                 855                 860
    Ser Asn Tyr Leu Ala Glu Leu Gln Glu Gly Asp Thr Ile Thr Cys Phe
    865                 870                 875                 880
    Ile Ser Thr Pro Gln Ser Glu Phe Thr Leu Pro Lys Asp Pro Glu Thr
                    885                 890                 895
    Pro Leu Ile Met Val Gly Pro Gly Thr Gly Val Ala Pro Phe Arg Gly
                900                 905                 910
    Phe Val Gln Ala Arg Lys Gln Leu Lys Glu Gln Gly Gln Ser Leu Gly
                915                 920                 925
    Glu Ala His Leu Tyr Phe Gly Cys Arg Ser Pro His Glu Asp Tyr Leu
            930                 935                 940
    Tyr Gln Glu Glu Leu Glu Asn Ala Gln Ser Glu Gly Ile Ile Thr Leu
    945                 950                 955                 960
    His Thr Ala Phe Ser Arg Met Pro Asn Gln Pro Lys Thr Tyr Val Gln
                    965                 970                 975
    His Val Met Glu Gln Asp Gly Lys Lys Leu Ile Glu Leu Leu Asp Gln
                980                 985                 990
    Gly Ala His Phe Tyr Ile Cys Gly Asp Gly Ser Gln Met Ala Pro Ala
                995                 1000                1005
    Val Glu Ala Thr Leu Met Lys Ser Tyr Ala Asp Val His Gln Val Ser
            1010                1015                1020
```

-continued

Glu Ala Asp Ala Arg Leu Trp Leu Gln Gln Leu Glu Glu Lys Gly Arg
1025                1030                1035                1040

Tyr Ala Lys Asp Val Trp Ala
            1045

<210> SEQ ID NO 105
<211> LENGTH: 3183
<212> TYPE: DNA
<213> ORGANISM: Bacillus subtilis

<400> SEQUENCE: 105

| | | | | |
|---|---|---|---|---|
| atgaaggaaa | caagcccgat | tcctcagccg | aagacgtttg | ggccgctcgg caatttgcct | 60 |
| ttaattgata | aagacaaacc | gacgctttcg | ctgatcaaac | tggcggaaga acagggcccg | 120 |
| attttcaaa | tccatacacc | cgcgggcacg | accattgtag | tgtccggcca tgaattggtg | 180 |
| aaagaggttt | gtgatgaaga | acggtttgat | aaaagcattg | aaggcgcctt ggaaaaggtt | 240 |
| cgcgcatttt | ccggtgacgg | attggccact | agttggacgc | atgagcctaa ctggagaaaa | 300 |
| gcgcacaaca | ttctgatgcc | gacgttcagc | cagcgggcca | tgaaggacta tcatgagaaa | 360 |
| atggtcgata | tcgctgttca | gctcattcaa | aaatgggcaa | ggctcaaccc gaatgaagca | 420 |
| gtcgatgtcc | cgggagatat | gacccggctg | acgctcgaca | ccattgggct atgcgggttt | 480 |
| aactaccgct | ttaacagtta | ctacagagaa | acgccccacc | cgtttatcaa cagcatggtg | 540 |
| cgggcgcttg | atgaagcgat | gcatcaaatg | cagcggcttg | atgttcaaga taagcttatg | 600 |
| gtcagaacaa | agcggcaatt | ccgctatgat | attcaaacga | tgttttcgtt agtcgacagc | 660 |
| attattgcag | agcgcagggc | gaatggagac | caggatgaaa | aagatttgct cgcccgcatg | 720 |
| ctgaatgtgg | aagatccgga | aactggtgaa | aagctcgacg | acgaaaatat ccgctttcag | 780 |
| atcatcacgt | ttttgattgc | cggccatgaa | acaacgagcg | gcctgctttc ctttgcgact | 840 |
| tacttttat | tgaagcatcc | tgacaaactg | aaaaaggcgt | atgaagaggt cgatcgggtg | 900 |
| ctgacggatg | cagcgccgac | ctataaacaa | gtgctggagc | ttacatacat acggatgatt | 960 |
| ttaaatgaat | cactgcgctt | atggccgaca | gctccggctt | tcagcccttta tccaaaagaa | 1020 |
| gacacagtca | ttggcggaaa | atttccgatc | acgacgaatg | cagaatttc tgtgctgatt | 1080 |
| ccgcagcttc | atcgtgatcg | agacgcttgg | ggaaaggacg | cagaagagtt ccggccggaa | 1140 |
| cggtttgagc | atcaggacca | agtgcctcat | catgcgtaca | aaccattcgg aaatggacaa | 1200 |
| cgggcctgta | tcggcatgca | gtttgcccctt | catgaagcca | cacttgtgtt aggcatgatt | 1260 |
| ctaaatatt | tcacattgat | tgatcatgag | aattatgagc | ttgatatcaa acaaaccctta | 1320 |
| acacttaagc | cgggcgattt | tcacatcagt | gttcaaagcc | gtcatcagga agccattcat | 1380 |
| gcagacgtcc | aggcagctga | aaaagccgcg | cctgatgagc | aaaaggagaa aacgaaagca | 1440 |
| aagggtgcat | cggtcatcgg | tcttaacaac | cgcccgcttc | tcgtgctgta cggctcagat | 1500 |
| accggcaccg | cagaaggcgt | cgcccgggag | cttgctgata | ctgccagtct tcacggcgta | 1560 |
| aggacaaaga | cagcacctct | gaacgaccgg | attggaaagc | tgccgaaaga gggagcggtt | 1620 |
| gtcattgtga | cctcgtctta | taatggaaag | ccgccaagca | atgccggaca attcgtgcag | 1680 |
| tggcttcaag | aaatcaaacc | gggtgagctt | gagggcgtcc | attacgcggt atttggctgc | 1740 |
| ggcgaccaca | actgggcgag | cacgtatcaa | tacgtgccga | gattcattga tgagcagctt | 1800 |
| gcggagaaag | gcgcgactcg | gttttctgcg | cgcgggaag | gggatgtgag cggtgatttt | 1860 |
| gaagggcagc | ttgacgagtg | gaaaaaaagc | atgtgggcgg | atgccatcaa agcattcgga | 1920 |
| cttgagctta | tgaaaacgc | tgataaggaa | cgaagcacgc | tgagccttca gtttgtcaga | 1980 |

-continued

```
gggctgggcg agtctccgct cgctagatcg tacgaagcct ctcacgcatc cattgccgaa    2040
aatcgtgaac tccagtccgc agacagcgat cgaagcactc gccatatcga aattgcattg    2100
ccgccggatg ttgaatatca agagggcgac catcttggcg tattgccaaa aaacagccaa    2160
accaatgtca gccggattct tcacagattc ggtctgaagg gaaccgacca agtgacattg    2220
tcggcaagcg gccgcagtgc ggggcatctg ccattgggcc gtcctgtcag cctgcatgat    2280
cttctcagct acagcgtcga ggtgcaggaa gcagccacaa gagcgcaaat acgtgaactg    2340
gcgtcattta cagtgtgtcc gccgcatagg cgcgaattag aagaactgtc agcagagggt    2400
gtttatcagg agcaaatatt gaaaaaacga atttccatgc tggatctgct tgaaaagtat    2460
gaagcgtgtg acatgccgtt tgaacgattt ttagagcttt tacggccgtt aaaaccgaga    2520
tactattcga tttcaagctc tccaagagtg aatccgcggc aagcatcgat acagtcggt    2580 gtcgtgcgcg gcccggcgtg gagcggccgt ggcgaataca ggggtgtggc atcaaatgat    2640
ttagctgagc gtcaagccgg tgatgatgtc gtgatgttta ccgcacacc ggaatcccgg    2700 tttcagcttc cgaaagaccc tgaaacgcca attattatgg tcgggccagg cacgggagtc    2760
gcgccatttc gcggtttcct tcaagcccgc gatgtttaa agcgggaggg caaaacgctc    2820
ggtgaggctc atctctattt tggatgcagg aacgatcggg atttattta ccgagatgag    2880 cttgagcggt tgaaaaaga cggaatcgtc actgtccaca cagcctttc ccgaaaagag    2940 ggcatgccga aaacatatgt ccagcatctc atggctgacc aagcagatac attaatatca    3000
atccttgacc gcggtggcag gctttatgta tgcggtgatg gcagcaaaat ggccccggat    3060
gtggaggcgg cacttcaaaa agcgtatcag gctgtccatg gaaccgggga acaagaagcg    3120
caaaactggc tgagacatct gcaggatacc ggtatgtacg ctaaggatgt ctgggcaggg    3180
ata                                                                   3183
```

<210> SEQ ID NO 106
<211> LENGTH: 1059
<212> TYPE: PRT
<213> ORGANISM: Bacillus subtilis

<400> SEQUENCE: 106

```
Lys Glu Thr Ser Pro Ile Pro Gln Pro Lys Thr Phe Gly Pro Leu Gly
 1               5                  10                  15

Asn Leu Pro Leu Ile Asp Lys Asp Lys Pro Thr Leu Ser Leu Ile Lys
            20                  25                  30

Leu Ala Glu Glu Gln Gly Pro Ile Phe Gln Ile His Thr Pro Ala Gly
        35                  40                  45

Thr Thr Ile Val Val Ser Gly His Glu Leu Val Lys Glu Val Cys Asp
    50                  55                  60

Glu Glu Arg Phe Asp Lys Ser Ile Glu Gly Ala Leu Glu Lys Val Arg
65                  70                  75                  80

Ala Phe Ser Gly Asp Gly Leu Ala Thr Ser Trp Thr His Glu Pro Asn
                85                  90                  95

Trp Arg Lys Ala His Asn Ile Leu Met Pro Thr Phe Ser Gln Arg Ala
            100                 105                 110

Met Lys Asp Tyr His Glu Lys Met Val Asp Ile Ala Val Gln Leu Ile
        115                 120                 125

Gln Lys Trp Ala Arg Leu Asn Pro Asn Glu Ala Val Asp Val Pro Gly
    130                 135                 140

Asp Met Thr Arg Leu Thr Leu Asp Thr Ile Gly Leu Cys Gly Phe Asn
145                 150                 155                 160
```

-continued

```
Tyr Arg Phe Asn Ser Tyr Tyr Arg Glu Thr Pro His Pro Phe Ile Asn
                165                 170                 175

Ser Met Val Arg Ala Leu Asp Glu Ala Met His Gln Met Gln Arg Leu
            180                 185                 190

Asp Val Gln Asp Lys Leu Met Val Arg Thr Lys Arg Gln Phe Arg Tyr
            195                 200                 205

Asp Ile Gln Thr Met Phe Ser Leu Val Asp Ser Ile Ile Ala Glu Arg
        210                 215                 220

Arg Ala Asn Gly Asp Gln Asp Glu Lys Asp Leu Leu Ala Arg Met Leu
225                 230                 235                 240

Asn Val Glu Asp Pro Glu Thr Gly Glu Lys Leu Asp Asp Glu Asn Ile
            245                 250                 255

Arg Phe Gln Ile Ile Thr Phe Leu Ile Ala Gly His Glu Thr Thr Ser
            260                 265                 270

Gly Leu Leu Ser Phe Ala Thr Tyr Phe Leu Leu Lys His Pro Asp Lys
            275                 280                 285

Leu Lys Lys Ala Tyr Glu Glu Val Asp Arg Val Leu Thr Asp Ala Ala
            290                 295                 300

Pro Thr Tyr Lys Gln Val Leu Glu Leu Thr Tyr Ile Arg Met Ile Leu
305                 310                 315                 320

Asn Glu Ser Leu Arg Leu Trp Pro Thr Ala Pro Ala Phe Ser Leu Tyr
                325                 330                 335

Pro Lys Glu Asp Thr Val Ile Gly Gly Lys Phe Pro Ile Thr Thr Asn
                340                 345                 350

Asp Arg Ile Ser Val Leu Ile Pro Gln Leu His Arg Asp Arg Asp Ala
                355                 360                 365

Trp Gly Lys Asp Ala Glu Glu Phe Arg Pro Glu Arg Phe Glu His Gln
370                 375                 380

Asp Gln Val Pro His His Ala Tyr Lys Pro Phe Gly Asn Gly Gln Arg
385                 390                 395                 400

Ala Cys Ile Gly Met Gln Phe Ala Leu His Glu Ala Thr Leu Val Leu
                405                 410                 415

Gly Met Ile Leu Lys Tyr Phe Thr Leu Ile Asp His Glu Asn Tyr Glu
            420                 425                 430

Leu Asp Ile Lys Gln Thr Leu Thr Leu Lys Pro Gly Asp Phe His Ile
            435                 440                 445

Ser Val Gln Ser Arg His Gln Glu Ala Ile His Ala Asp Val Gln Ala
        450                 455                 460

Ala Glu Lys Ala Ala Pro Asp Glu Gln Lys Lys Thr Glu Ala Lys
465                 470                 475                 480

Gly Ala Ser Val Ile Gly Leu Asn Asn Arg Pro Leu Leu Val Leu Tyr
            485                 490                 495

Gly Ser Asp Thr Gly Thr Ala Glu Gly Val Ala Arg Glu Leu Ala Asp
            500                 505                 510

Thr Ala Ser Leu His Gly Val Arg Thr Lys Thr Ala Pro Leu Asn Asp
            515                 520                 525

Arg Ile Gly Lys Leu Pro Lys Glu Gly Ala Val Ile Val Thr Ser
            530                 535                 540

Ser Tyr Asn Gly Lys Pro Pro Ser Asn Ala Gly Gln Phe Val Gln Trp
545                 550                 555                 560

Leu Gln Glu Ile Lys Pro Gly Glu Leu Glu Gly Val His Tyr Ala Val
                565                 570                 575

Phe Gly Cys Gly Asp His Asn Trp Ala Ser Thr Tyr Gln Tyr Val Pro
            580                 585                 590
```

```
Arg Phe Ile Asp Glu Gln Leu Ala Glu Lys Gly Ala Thr Arg Phe Ser
        595                 600                 605

Ala Arg Gly Glu Gly Asp Val Ser Gly Asp Phe Glu Gly Gln Leu Asp
    610                 615                 620

Glu Trp Lys Lys Ser Met Trp Ala Asp Ala Ile Lys Ala Phe Gly Leu
625                 630                 635                 640

Glu Leu Asn Glu Asn Ala Asp Lys Glu Arg Ser Thr Leu Ser Leu Gln
            645                 650                 655

Phe Val Arg Gly Leu Gly Glu Ser Pro Leu Ala Arg Ser Tyr Glu Ala
        660                 665                 670

Ser His Ala Ser Ile Ala Glu Asn Arg Glu Leu Gln Ser Ala Asp Ser
    675                 680                 685

Asp Arg Ser Thr Arg His Ile Glu Ile Ala Leu Pro Pro Asp Val Glu
690                 695                 700

Tyr Gln Glu Gly Asp His Leu Gly Val Leu Pro Lys Asn Ser Gln Thr
705                 710                 715                 720

Asn Val Ser Arg Ile Leu His Arg Phe Gly Leu Lys Gly Thr Asp Gln
            725                 730                 735

Val Thr Leu Ser Ala Ser Gly Arg Ser Ala Gly His Leu Pro Leu Gly
        740                 745                 750

Arg Pro Val Ser Leu His Asp Leu Leu Ser Tyr Ser Val Glu Val Gln
    755                 760                 765

Glu Ala Ala Thr Arg Ala Gln Ile Arg Glu Leu Ala Ser Phe Thr Val
770                 775                 780

Cys Pro Pro His Arg Arg Glu Leu Glu Glu Leu Ser Ala Glu Gly Val
785                 790                 795                 800

Tyr Gln Glu Gln Ile Leu Lys Lys Arg Ile Ser Met Leu Asp Leu Leu
            805                 810                 815

Glu Lys Tyr Glu Ala Cys Asp Met Pro Phe Glu Arg Phe Leu Glu Leu
        820                 825                 830

Leu Arg Pro Leu Lys Pro Arg Tyr Tyr Ser Ile Ser Ser Ser Pro Arg
    835                 840                 845

Val Asn Pro Arg Gln Ala Ser Ile Thr Val Gly Val Val Arg Gly Pro
850                 855                 860

Ala Trp Ser Gly Arg Gly Glu Tyr Arg Gly Val Ala Ser Asn Asp Leu
865                 870                 875                 880

Ala Glu Arg Gln Ala Gly Asp Val Val Met Phe Ile Arg Thr Pro
            885                 890                 895

Glu Ser Arg Phe Gln Leu Pro Lys Asp Pro Glu Thr Pro Ile Ile Met
        900                 905                 910

Val Gly Pro Gly Thr Gly Val Ala Pro Phe Arg Gly Phe Leu Gln Ala
    915                 920                 925

Arg Asp Val Leu Lys Arg Glu Gly Lys Thr Leu Gly Glu Ala His Leu
930                 935                 940

Tyr Phe Gly Cys Arg Asn Asp Arg Asp Phe Ile Tyr Arg Asp Glu Leu
945                 950                 955                 960

Glu Arg Phe Glu Lys Asp Gly Ile Val Thr Val His Thr Ala Phe Ser
            965                 970                 975

Arg Lys Glu Gly Met Pro Lys Thr Tyr Val Gln His Leu Met Ala Asp
        980                 985                 990

Gln Ala Asp Thr Leu Ile Ser Ile Leu Asp Arg Gly Gly Arg Leu Tyr
    995                 1000                1005

Val Cys Gly Asp Gly Ser Lys Met Ala Pro Asp Val Glu Ala Ala Leu
```

Gln Lys Ala Tyr Gln Ala Val His Gly Thr Gly Glu Gln Glu Ala Gln
1025                1030                1035                1040

Asn Trp Leu Arg His Leu Gln Asp Thr Gly Met Tyr Ala Lys Asp Val
            1045                1050                1055

Trp Ala Gly

<210> SEQ ID NO 107
<211> LENGTH: 3162
<212> TYPE: DNA
<213> ORGANISM: Bacillus subtilis

<400> SEQUENCE: 107

| | | | | | |
|---|---|---|---|---|---|
| atgaaacagg | caagcgcaat | acctcagccc | aaaacatacg | gacctttaaa | aaatcttccg | 60 |
| catctggaaa | agaacagct | ttctcaatcc | ttatggcgga | tagctgatga | attgggaccg | 120 |
| attttccgtt | ttgatttttcc | gggagtatcc | agtgttttg | tgtccggcca | caatcttgtg | 180 |
| gctgaagtgt | gtgatgaaaa | acgctttgac | aagaaccttg | gcaaaggctt | gcaaaaggtg | 240 |
| cgtgagttcg | ggggagatgg | cttagccact | agttggacgc | acgaaccgaa | ctggcaaaaa | 300 |
| gcccaccgca | ttttgctgcc | gagttttagt | caaaaagcga | tgaaaggcta | tcattctatg | 360 |
| atgctggata | tcgcaaccca | gctgattcaa | aagtggagcc | ggttaaaccc | taatgaagaa | 420 |
| attgatgtag | cggacgatat | gacacgtctg | acgcttgata | cgattgggtt | atgcgggttt | 480 |
| aactatcgat | tcaacagctt | ttaccgtgat | tcacagcatc | cgtttatcac | cagtatgctc | 540 |
| cgtgccttaa | agaggcgat | gaatcaatcg | aaaagactgg | gcctgcaaga | taaaatgatg | 600 |
| gtgaaaacga | agctgcagtt | ccaaaaggat | atagaagtca | tgaactccct | ggttgataga | 660 |
| atgatagcgg | agcgaaaggc | gaatccggat | gaaaacatta | aggatctctt | gtctctcatg | 720 |
| ctttatgcca | aagatccagt | aacgggtgaa | acgctggatg | acgaaaacat | tcgataccaa | 780 |
| atcatcacat | ttttaattgc | tggacatgag | acaacaagcg | ggttgctatc | ctttgcgatt | 840 |
| tattgtctgc | ttacacatcc | ggaaaaactg | aaaaaagctc | aggaggaagc | ggatcgcgtg | 900 |
| ttaacggatg | acacgcctga | atataaacaa | atccagcagc | tcaaatacat | tcggatggtt | 960 |
| ttaaatgaaa | ccctcagact | gtatccaaca | gctccggctt | tttctctata | tgcgaaggag | 1020 |
| gatactgttc | taggcgggga | atatccgatc | agcaaagggc | agccagtcac | tgttttaatt | 1080 |
| ccaaaactgc | accgggatca | aaacgcttgg | ggaccggatg | cggaagattt | ccgtccggaa | 1140 |
| cggtttgaag | atccttcaag | tatccctcac | catgcgtata | agccgtttgg | aaacggacag | 1200 |
| cgcgcttgta | ttggcatgca | gtttgctctt | caagaagcga | caatggttct | cggtcttgta | 1260 |
| ttaaagcatt | ttgaattgat | aaaccatact | ggctacgaac | taaaaatcaa | agaagcatta | 1320 |
| acgatcaagc | cggatgattt | taaaattact | gtgaaaccgc | gaaaaacagc | ggcaatcaat | 1380 |
| gtacagagaa | agaacaggc | agacatcaaa | gcagaaacaa | agccaaaaga | aaccaaacct | 1440 |
| aaacacggca | cacctttact | tgttctttt | ggttcaaatc | ttgggacagc | tgagggaata | 1500 |
| gccggtgaac | tggctgctca | aggccgccag | atgggcttta | cagctgaaac | ggctccgctt | 1560 |
| gatgattata | tcggcaagct | ccctgaagaa | ggggcagtcg | tcattgtaac | ggcttcttat | 1620 |
| aatgggcgc | cgcctgataa | tgctgccgga | tttgtagagt | ggctgaaaga | gcttgaggaa | 1680 |
| ggccaattga | aaggtgtttc | ctatgcggta | ttcggctgcg | aaaccggag | ctgggccagc | 1740 |
| acgtatcagc | ggattccccg | cctgattgat | gacatgatga | agcaaagggg | ggcatcgcgt | 1800 |
| ttaacagcga | ttggggaagg | tgacgccgcc | gatgattttg | aaagccaccg | cgagtcttgg | 1860 |

```
gaaaaccgct tctggaagga aacgatggac gcatttgata ttaacgaaat agcccagaaa   1920
gaagacaggc cttcattatc gattactttt ctcagtgaag cgacgaaaac gccggttgct   1980
aaagcatatg gcgcgtttga agggattgtg ttagagaatc gagaactcca gacagctgcc   2040
agcacgcgtt caacccgcca tattgaattg gaaattccgg ctggtaaaac atataaagaa   2100
ggcgatcata tcggaatcct gccaaagaac agcagggagc ttgttcagcg ggttctcagc   2160
cgattcggtt tgcagtccaa tcatgtgata aagtaagcg gaagcgctca tatggctcat    2220
ctgccgatgg atcggccaat caaagtagtg gatttattgt cgtcctatgt agagctgcag   2280
gaaccggcat caaggcttca gcttcgggag ctggcctctt atacagtttg tccgccgcat   2340
caaaaagagc tggaacagct cgtttcagat gatggcattt acaaagagca ggtacttgca   2400
aaacgtctta ccatgcttga tttttttagag gattatcctg cttgcgaaat gccgtttgaa   2460 cggttttttag cacttttgcc atcactaaaa ccgagatact attccatttc aagctcaccg    2520
aaagttcatg caaatatcgt gagcatgacg gtaggagttg tgaaagcctc agcatggagc   2580
ggccgaggtg aataccgggg tgtcgcctct aattatttag cagaattgaa tacaggtgat   2640
gcagcagctt gcttcattcg tacgccgcag tccggatttc agatgccgaa tgatcctgaa   2700
acgcctatga ttatggtcgg gccgggcaca ggaattgcgc cattcagagg ctttattcag   2760
gcaagatcgg ttttgaagaa ggaaggaagc acccttggtg aagcactttt atacttcggc   2820
tgccgccgcc cggaccatga cgacctttac agagaagagc tggatcaagc ggaacaggac   2880
ggtttggtca caatccgccg atgctactcg cgcgtcgaaa acgaaccaaa aggatatgtc   2940
cagcacttgc tcaagcaaga tacgcagaaa ttgatgacac tcattgaaaa agggggctcat   3000 atttacgtat gcggtgatgg atcgcaaatg gctcctgatg tagagagaac tttgcgattg   3060
gcatatgaag ctgaaaaagc agcaagtcag gaagaatcag ctgtatggct gcaaaagctg   3120
caagatcaaa gacgttatgt gaaagacgtt tggacaggaa tg                     3162
```

<210> SEQ ID NO 108
<211> LENGTH: 1052
<212> TYPE: PRT
<213> ORGANISM: Bacillus subtilis

<400> SEQUENCE: 108

```
Lys Gln Ala Ser Ala Ile Pro Gln Pro Lys Thr Tyr Gly Pro Leu Lys
 1               5                   10                  15

Asn Leu Pro His Leu Glu Lys Glu Gln Leu Ser Gln Ser Leu Trp Arg
            20                  25                  30

Ile Ala Asp Glu Leu Gly Pro Ile Phe Arg Phe Asp Phe Pro Gly Val
        35                  40                  45

Ser Ser Val Phe Val Ser Gly His Asn Leu Val Ala Glu Val Cys Asp
    50                  55                  60

Glu Lys Arg Phe Asp Lys Asn Leu Gly Lys Gly Leu Gln Lys Val Arg
65                  70                  75                  80

Glu Phe Gly Gly Asp Gly Leu Ala Thr Ser Trp Thr His Glu Pro Asn
                85                  90                  95

Trp Gln Lys Ala His Arg Ile Leu Leu Pro Ser Phe Ser Gln Lys Ala
            100                 105                 110

Met Lys Gly Tyr His Ser Met Met Leu Asp Ile Ala Thr Gln Leu Ile
        115                 120                 125

Gln Lys Trp Ser Arg Leu Asn Pro Asn Glu Glu Ile Asp Val Ala Asp
    130                 135                 140

Asp Met Thr Arg Leu Thr Leu Asp Thr Ile Gly Leu Cys Gly Phe Asn
```

-continued

```
                145                 150                 155                 160
        Tyr Arg Phe Asn Ser Phe Tyr Arg Asp Ser Gln His Pro Phe Ile Thr
                        165                 170                 175

Ser Met Leu Arg Ala Leu Lys Glu Ala Met Asn Gln Ser Lys Arg Leu
                        180                 185                 190

Gly Leu Gln Asp Lys Met Met Val Lys Thr Lys Leu Gln Phe Gln Lys
                        195                 200                 205

Asp Ile Glu Val Met Asn Ser Leu Val Asp Arg Met Ile Ala Glu Arg
        210                 215                 220

Lys Ala Asn Pro Asp Glu Asn Ile Lys Asp Leu Leu Ser Leu Met Leu
        225                 230                 235                 240

Tyr Ala Lys Asp Pro Val Thr Gly Glu Thr Leu Asp Asp Glu Asn Ile
                        245                 250                 255

Arg Tyr Gln Ile Ile Thr Phe Leu Ile Ala Gly His Glu Thr Thr Ser
                        260                 265                 270

Gly Leu Leu Ser Phe Ala Ile Tyr Cys Leu Leu Thr His Pro Glu Lys
                        275                 280                 285

Leu Lys Lys Ala Gln Glu Glu Ala Asp Arg Val Leu Thr Asp Asp Thr
        290                 295                 300

Pro Glu Tyr Lys Gln Ile Gln Gln Leu Lys Tyr Ile Arg Met Val Leu
        305                 310                 315                 320

Asn Glu Thr Leu Arg Leu Tyr Pro Thr Ala Pro Ala Phe Ser Leu Tyr
                        325                 330                 335

Ala Lys Glu Asp Thr Val Leu Gly Gly Glu Tyr Pro Ile Ser Lys Gly
                        340                 345                 350

Gln Pro Val Thr Val Leu Ile Pro Lys Leu His Arg Asp Gln Asn Ala
                        355                 360                 365

Trp Gly Pro Asp Ala Glu Asp Phe Arg Pro Glu Arg Phe Glu Asp Pro
        370                 375                 380

Ser Ser Ile Pro His His Ala Tyr Lys Pro Phe Gly Asn Gly Gln Arg
        385                 390                 395                 400

Ala Cys Ile Gly Met Gln Phe Ala Leu Gln Glu Ala Thr Met Val Leu
                        405                 410                 415

Gly Leu Val Leu Lys His Phe Glu Leu Ile Asn His Thr Gly Tyr Glu
                        420                 425                 430

Leu Lys Ile Lys Glu Ala Leu Thr Ile Lys Pro Asp Asp Phe Lys Ile
                        435                 440                 445

Thr Val Lys Pro Arg Lys Thr Ala Ala Ile Asn Val Gln Arg Lys Glu
        450                 455                 460

Gln Ala Asp Ile Lys Ala Glu Thr Lys Pro Lys Glu Thr Lys Pro Lys
        465                 470                 475                 480

His Gly Thr Pro Leu Leu Val Leu Phe Gly Ser Asn Leu Gly Thr Ala
                        485                 490                 495

Glu Gly Ile Ala Gly Glu Leu Ala Ala Gln Gly Arg Gln Met Gly Phe
                        500                 505                 510

Thr Ala Glu Thr Ala Pro Leu Asp Asp Tyr Ile Gly Lys Leu Pro Glu
                        515                 520                 525

Glu Gly Ala Val Val Ile Val Thr Ala Ser Tyr Asn Gly Ala Pro Pro
                        530                 535                 540

Asp Asn Ala Ala Gly Phe Val Glu Trp Leu Lys Glu Leu Glu Glu Gly
        545                 550                 555                 560

Gln Leu Lys Gly Val Ser Tyr Ala Val Phe Gly Cys Gly Asn Arg Ser
                        565                 570                 575
```

-continued

```
Trp Ala Ser Thr Tyr Gln Arg Ile Pro Arg Leu Ile Asp Asp Met Met
            580                 585                 590

Lys Ala Lys Gly Ala Ser Arg Leu Thr Ala Ile Gly Glu Gly Asp Ala
        595                 600                 605

Ala Asp Asp Phe Glu Ser His Arg Glu Ser Trp Glu Asn Arg Phe Trp
610                 615                 620

Lys Glu Thr Met Asp Ala Phe Asp Ile Asn Glu Ile Ala Gln Lys Glu
625                 630                 635                 640

Asp Arg Pro Ser Leu Ser Ile Thr Phe Leu Ser Glu Ala Thr Glu Thr
                645                 650                 655

Pro Val Ala Lys Ala Tyr Gly Ala Phe Glu Gly Ile Val Leu Glu Asn
            660                 665                 670

Arg Glu Leu Gln Thr Ala Ala Ser Thr Arg Ser Thr Arg His Ile Glu
        675                 680                 685

Leu Glu Ile Pro Ala Gly Lys Thr Tyr Lys Glu Gly Asp His Ile Gly
    690                 695                 700

Ile Leu Pro Lys Asn Ser Arg Glu Leu Val Gln Arg Val Leu Ser Arg
705                 710                 715                 720

Phe Gly Leu Gln Ser Asn His Val Ile Lys Val Ser Gly Ser Ala His
                725                 730                 735

Met Ala His Leu Pro Met Asp Arg Pro Ile Lys Val Val Asp Leu Leu
            740                 745                 750

Ser Ser Tyr Val Glu Leu Gln Glu Pro Ala Ser Arg Leu Gln Leu Arg
        755                 760                 765

Glu Leu Ala Ser Tyr Thr Val Cys Pro Pro His Gln Lys Glu Leu Glu
    770                 775                 780

Gln Leu Val Ser Asp Asp Gly Ile Tyr Lys Glu Gln Val Leu Ala Lys
785                 790                 795                 800

Arg Leu Thr Met Leu Asp Phe Leu Glu Asp Tyr Pro Ala Cys Glu Met
                805                 810                 815

Pro Phe Glu Arg Phe Leu Ala Leu Leu Pro Ser Leu Lys Pro Arg Tyr
            820                 825                 830

Tyr Ser Ile Ser Ser Ser Pro Lys Val His Ala Asn Ile Val Ser Met
        835                 840                 845

Thr Val Gly Val Val Lys Ala Ser Ala Trp Ser Gly Arg Gly Glu Tyr
    850                 855                 860

Arg Gly Val Ala Ser Asn Tyr Leu Ala Glu Leu Asn Thr Gly Asp Ala
865                 870                 875                 880

Ala Ala Cys Phe Ile Arg Thr Pro Gln Ser Gly Phe Gln Met Pro Asn
                885                 890                 895

Asp Pro Glu Thr Pro Met Ile Met Val Gly Pro Gly Thr Gly Ile Ala
            900                 905                 910

Pro Phe Arg Gly Phe Ile Gln Ala Arg Ser Val Leu Lys Lys Glu Gly
        915                 920                 925

Ser Thr Leu Gly Glu Ala Leu Leu Tyr Phe Gly Cys Arg Arg Pro Asp
    930                 935                 940

His Asp Asp Leu Tyr Arg Glu Glu Leu Asp Gln Ala Glu Gln Asp Gly
945                 950                 955                 960

Leu Val Thr Ile Arg Arg Cys Tyr Ser Arg Val Glu Asn Glu Pro Lys
                965                 970                 975

Gly Tyr Val Gln His Leu Leu Lys Gln Asp Thr Gln Lys Leu Met Thr
            980                 985                 990

Leu Ile Glu Lys Gly Ala His Ile Tyr Val Cys Gly Asp Gly Ser Gln
        995                 1000                1005
```

```
Met Ala Pro Asp Val Glu Arg Thr Leu Arg Leu Ala Tyr Glu Ala Glu
    1010                1015                1020
Lys Ala Ala Ser Gln Glu Glu Ser Ala Val Trp Leu Gln Lys Leu Gln
1025                1030                1035                1040
Asp Gln Arg Arg Tyr Val Lys Asp Val Trp Thr Gly
                1045                1050
```

LIBRARIES OF OPTIMIZED CYTOCHROME P450 ENZYMES AND THE OPTIMIZED P450 ENZYMES

RELATED APPLICATIONS

This Application claims priority of U.S. Provisional Application 60/479,005 filed Jun. 17, 2003, herein incorporated by reference in its entirety.

GOVERNMENTAL RIGHTS

This invention was made with government support under Grant Number DAAD19-00-1-0391 awarded by the Army. The government has certain rights in the invention.

FIELD OF THE INVENTION

The invention relates to chimeric P450 proteins with new and improved functionalities, libraries of such proteins, methods of making such proteins and libraries, and methods of characterizing such proteins and libraries.

BACKGROUND OF THE INVENTION

The cytochrome P450 superfamily of enzymes exhibits an impressive range of chemical activities and biological roles. Nature has exploited these diverse enzymes for everything from steroid biosynthesis to interspecies chemical warfare, protection of the organisms from toxic compounds, drug detoxification and utilization of new food sources. (Ortiz de Montellano, P. R., Cytochrome P450: Structure, Mechanism, and Biochemistry (New York: Plenum Press) (1995); Gotoh, O., Cytochrome P450, 2nd Edition, pp. 255-272 (1993); Gonzalez et al., Trends Genet, 6:182-186 (1990); Mauersberger et al., Z Alig Mikrobiol., 121:313-321 (1981); Porter et al., J. Biol. Chem., 266:13469-13472 (1991)).

While activities are diverse across the entire superfamily, individual members of the superfamily show a much narrower range of catalytic activities, usually catalyzing oxygen insertion into C—H bonds and substrate specificities. The heme prosthetic group recruited by the cytochrome P450s to effect monooxygenation is also used by these and other proteins for oxygen transport, electron transfer, reduction, dealkylation and dehalogenation. (Sono et al., Chem Rev 96, 2841-2888 (1996), Eichhorn et al., Heme Proteins, New York, N.Y.: Elsevier Science Publishing Co., Inc. (1988)).

Recent engineering efforts have demonstrated that P450s can acquire new or improved activities by point mutation (Cirino, P. C., and Arnold, F. H., *Angew Chem Int Ed Engl* 42, 3299-3301 (2003); Li et al., Biochem Biophys. Acta., 1545: 114-121 (2001); Glieder et al., Nat. Biotechnol. 20:1135-1139 (2002); Li et al., Chemistry, 6:1531-1536 (2000); Joo et al., Nature, 399:670-673 (1999); Appel et al., J. Biotechnol., 88:167-171 (2001)). However, making and characterizing each engineered P450 can be a laborious and time-consuming process. This is especially true when many of the mutations made, if done randomly, result in proteins with little or no function. This is even further exacerbated if one desires high levels of mutation. One possible way around this is to create libraries containing potentially numerous useful proteins by recombining different P450s either from nature or which have created in the laboratory. This could at least reduce the initial amount of work involved in creating the enzymes, although a substantial amount of work will still be required in testing these libraries.

However, creating protein libraries is not a simple matter, especially for P450s. P450s typically exhibit low sequence identity. Thus, annealing-based DNA-shuffling techniques are largely useless for creating highly diverse libraries of P450 chimeras or for creating the individual chimeric proteins (Stemmer, W P, Proc. Natl. Acad. Sci. USA, 91:10747-10751 (1994); Coco, W M. et al., Nat. Biotechnol., 19:354-359 (2001); Zhao, H. et al. (1998). Nat. Biotechnol., 16:258-261; Volkov, A A et al., Nucleic Acids Res., 27, e18 (1999); Kikuchi, M. et al., Gene, 243:133-137 (2000)). While there are some methods for making shuffled gene libraries independent of sequence homology, these approaches generate few crossovers and large numbers of inactive sequences due to insertions, deletions, and frameshifts, as well as disruptive crossover events. (Lutz, S. et al. Proc Natl Acad Sci USA, 98:11248-11253 (2001); Sieber, V. et al., Nat Biotechnol., 19:456-460 (2001)). Additionally, functional characterization of such libraries is extremely difficult without a selection method that can remove unfolded or nonfunctional sequences. Finally, as such libraries do not currently generally exist, the functional abilities, characteristics, benefits of, and method of characterizing such libraries currently remain unknown, although attempts have been made (Abecassis et al., *Nucleic Acids Res* 28:E88, (2000)).

SUMMARY OF THE INVENTION

The present embodiments are directed to chimeric proteins and the creation of libraries of chimeric P450 enzymes with new or improved functionalities. In particular, the creation of chimeras through recombination and the use of the software program "SCHEMA" to characterize the functionality of the resulting chimeras. In one embodiment, the number of mutations in each P450 enzyme plays a role in determining the likelihood of altered functionality. Additionally, the resulting chimeric P450 proteins are also embodiments that are discussed and characterized.

One embodiment is a library of an optimized cytochrome P450 gene that encodes at least one optimized protein. The optimized protein has a first set of amino acid interactions and the sequences of the optimized proteins are derived from at least one parental cytochrome P450 gene. The parental cytochrome P450 gene encodes a protein having a second set of amino acid interactions. A protein or nucleic acid sequence will be optimized when the first set has fewer than 30 amino acid interactions disrupted, and when the protein has an enzymatic activity towards a substrate.

Another embodiment is a library of an optimized cytochrome P450 gene that encodes at least one optimized protein. The optimized protein has a first set of amino acid interactions and the sequences of the optimized proteins are derived from the recombination of at least one parental cytochrome P450 gene from a CYP102 family gene. The parental cytochrome P450 gene encodes a protein having a second set of amino acid interactions. A protein or nucleic acid sequence will be optimized when the first set has fewer than 30 amino acid interactions disrupted, and when the protein has an enzymatic activity towards a substrate.

Another embodiment is a cytochrome P450 chimera comprising a F helix portion from a CYP102A2 P450 protein and a G helix portion from a CYP102A1 P450 protein that has an enzymatic activity towards a substrate.

Another embodiment is a method of selecting a chimeric P450 enzyme for enzymatic activity towards a substrate. The steps involve, providing a first cytochrome P450 protein that has a first set of amino acid interactions, obtaining a chimeric P450 enzyme comprising a first segment from the first P450 protein and a second segment from a second P450 protein, determining a second set of amino acid interactions between pairs of amino acids in the chimeric P450 enzyme, determining the difference between the first set of amino acid interactions and the second set of amino acid interactions, and selecting a chimeric P450 enzyme that has lost less than 40 amino acid interactions in the second set compared to the interactions in the first set, and wherein said chimeric P450 enzyme has an increased activity towards said substrate.

DETAILED DESCRIPTION OF THE PREFERRED EMBODIMENT

Figure 1:
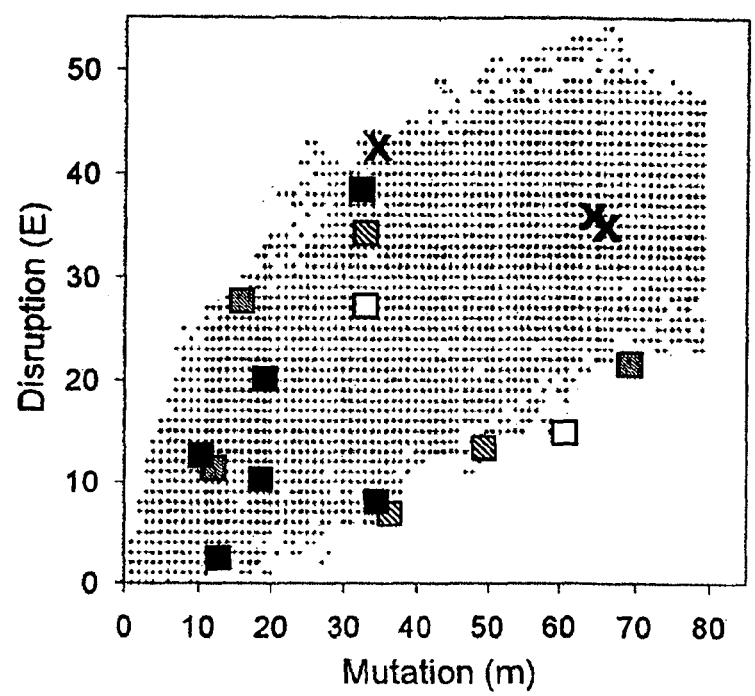
FIG. 1 is a graph displaying the relationship between effective mutation and disruption (E) for cytochrome P450 chimeras and their functionality.

Libraries generated by recombination of homologous proteins can be rich in folded proteins if the parent proteins are highly similar or if appropriate structural information is incorporated in the library design. (Hansson et al. J. Mol. Biol. 287:265-276, (1999), Moore et al., J. Mol. Biol. 272: 336-347, (1997), Voigt et al., Nat. Struct. Biol. 9:553-558 (2002), Meyer et al., Prot. Sci. (2003)). However, how functional diversity of chimeras is related to the level of sequence diversity of the parents in such libraries was previously unknown.

Embodiments of the invention relate to the discovery that recombination of functionally-similar enzymes yielded functionally-diverse chimeras. In addition, it was also discovered that even if functionally-similar parent enzymes do not share an overly similar primary structure, a large percentage of chimeric proteins derived from the parent enzymes were still able to fold and properly function. Thus, one embodiment is a method of creating chimeric proteins, including P450 enzymes, through the recombination of functionally similar proteins with low sequence identity. In another embodiment, a method for the recombination of functionally dissimilar proteins is contemplated. As appreciated by one of skill in the art, other benefits may be obtained by recombining functionally dissimilar proteins using the methods disclosed herein.

One embodiment of the invention is a method of selecting chimeras in recombinant libraries of P450 enzymes. In this embodiment, the chimeras are created by determining the number of disruptions of amino acid residue interactions that would result from combining two or more parental amino acid segments together to create a chimera. One measure of the number of disruptions of amino acid residues in a chimera is an "E value". This value is employed to describe the relative number of contacts, or amino acid interactions, broken in a potential chimera. The E value can reveal how likely a chimeric protein, such as a P450 enzyme, will properly fold, and how likely it is to be active. Thus, by using such a value, one can determine potential crossover points for creating a recombinant library, or protein, wherein the library members have a high likelihood of properly functioning. In one embodiment, the computational algorithm SCHEMA is used to predict E values of protein segments of parent proteins that can be used to design libraries that are rich in folded and functional proteins.

SCHEMA is a computational algorithm that can estimate the disruption caused by swapping different fragments among structurally-similar proteins. By using this generated value, one can identify optimal crossover locations for making libraries by recombination. (Voigt, C A et al., Nat Struct Biol 9, 553-558 (2002); Meyer et al., Prot. Sci., (2003)). The SCHEMA algorithm uses the 3D structure of one of the parent proteins to identify pairs of amino acids that interact and form contacts or interactions this is commonly called a 'contact diagram' (e.g., residues within a cutoff distance of 4.5 Å) and determines the net number of contacts or interactions broken when a chimeric protein inherits portions of its sequence from different parents. As described above, this value is termed an "E value". For each interaction or contact that is calculated to be broken, the E value increases by one point. Thus, the higher the E value, the more interactions or contacts that are broken within a given chimera. In one embodiment the number and nature of contacts for a parent is determined through a contact matrix (for example, defined as a set of residues within a certain distance from a given residue within its structure). For each amino acid that is changed in the chimera, all associated contacts with that residue are presumed disrupted. The number of these disrupted contacts are then summed to obtain an E value for the chimera.

Another embodiment of the invention employs an "m value", which is a calculated value describing the number of mutations present in the chimera in comparison to the original parental proteins. The m value is an indicator of whether or not the resulting chimera will have a novel or improved function. Typically, chimeras with higher m values are more likely to have a novel function in comparison to their parent since they contain a relatively higher number of amino acid mutations. Similarly, chimeras with a lower m value have a greater likelihood of displaying similar, but possibly improved activity. Accordingly, one can select chimeras that have a relatively high m value in order to identify those chimeras with improved function. In one embodiment, an m value of less than about 15 or 16 is an accurate indicator that the chimera or library will have novel substrate or functional activity. In another embodiment, when the E value is less than 30, a m value of 33 will also be considered low. For example, 30-25, 25-20, 20-15, 15-10, 10-5, 5-0. Thus, this value can depend on the E value to some extent. In one embodiment, a m value greater than 15 or 16 is considered a high value and thus likely to exhibit novel functionality, especially towards novel substrates. For example, 16-17, 17-20, 20-25, 25-30, 30-40, 40-50, 50-60, 70-90, or more. In another embodiment, a m value greater than 30 or 33 is considered high. As will one of skill in the art will appreciate, the higher or lower the m number, the greater the likelihood that a novel or improved function will be present.

In one embodiment, the E value and the m value are used together, allowing one to predict, and thus select, chimeric proteins having desired characteristics from a protein library. In one embodiment, the chimeric proteins in the library are selected to be enzymes that are very likely to fold and thus function properly. In addition, these enzymes would also be very likely to display novel activities or enhanced activity on traditional substrates. Enzymes or libraries selected or made through the manipulation of these values are termed "optimized."

In one embodiment, libraries of P450 chimeras are selected based on heightened concentrations of chimeras with the desired E and m values. In one embodiment, a library of chimeras with an E value of less than 30 ($E_{30}$) and an m value of greater than 30 ($m_{30}$) is desired, although greater or lesser values are contemplated. Thus, optimized libraries, which are libraries with a significant increase in the number of functional or novel functional enzymes, can be created or selected from the use of one or both of these values. For example, libraries with chimeras that have an average E value that is low, will be preferred over libraries with chimeras that have an average E value that is higher. Similarly, a library with m values that are higher than average may be preferred over libraries with average m values.

As described in detail below, P450 chimeras were created and characterized through this process, and found to exhibit significant functional diversity, including the ability to hydroxylate substrates not accepted by either parent enzyme. The chimeras may be useful for chemical synthesis, development of biomaterials, bioremediation, or protein-based therapeutics.

Embodiments further include methods to select those chimeras in a library that have the greatest likelihood of folding and being active. In one embodiment, numerous P450 chimeras are created by computer, e.g., in silico, and then the calculated E value for each predicted chimeric P450 enzyme is determined through the use of a program such as SCHEMA. By examining the E values of the predicted chimeras, one can identify and select from a library comprising recombinant mutants those chimeras that have a higher likelihood of folding and improved enzymatic activity compared to randomly created or selected chimeras. In one embodiment, any algorithm based on pair-wise interactions could be used to determine if a contact is broken (for example, see Saraf, et al., FamClash: a method for ranking the activity of engineered enzymes. Proc Natl Acad Sci USA 101, 4142-4147 (2004); Roy et al., Centripetal modules and ancient introns. Gene 238, 85-91 (1999); Fischer, K. F., and Marqusee, S. A rapid test for identification of autonomous folding units in proteins. J Mol Biol 302, 701-712. (2000); Dahiyat, B. I., and Mayo, S. L. Protein design automation. Protein Sci 5, 895-903 (1996)).

Embodiments of the invention further include libraries, and the isolated proteins comprising the libraries, of chimeras from a recombination of particular cytochrome P450 enzymes. For example, libraries of chimeras created from crossovers or mutations of P40 enzymes CYP102A1 and CYP102A2 (63% amino acid identity) can be created. As discussed below, the selection of where CYP102A1 and CYP102A2 should be recombined (i.e., a crossover point) can be guided by the E values that would result from such potential crossovers.

One embodiment of the invention relates to seventeen double-crossover chimeras that were constructed from the heme domains of a P450 CYP102A1 and CYP102A2 In one embodiment, the CYP102A 1 and CYP102A2 combined proteins comprise a library, and the library, when combined with an E value, is optimized as the structural and functional characteristics of the proteins are predicted. Almost all of the chimeras predicted to have limited structural disruption (e.g., a disruption that allows for the protein to still fold), via a SCHEMA determined substantially low E value (e.g., less than 30), were shown to be folded P450s, and the vast majority were found to be catalytically active, as described below. In addition these chimeras exhibited significant functional diversity. Chimeras displayed altered substrate specificity profiles, a wide range in thermostabilities, up to a 40-fold increase in peroxidase activity, and the ability to hydroxylate at least one substrate that had no demonstrated detectable activity from either parent.

Embodiments further include libraries of CYP102A1 and CYP102A2 chimeras with crossovers at amino acid positions 363, 403, 164, 256, 284, 341, 168, 197, 117, 194, 49, 140, 69, 299, 45, 73, 190, 335, 42, 135, 64, 256, 276, and 365. One or all of the crossovers may exist in each of the chimeras. Embodiments further include libraries of CYP102A1, CYP102A2, and CYP102A3 chimeras with crossovers at amino acid positions 64, 122, 166, 216, 268, 328, 404. One or all of the crossovers may exist in each of the chimeras. For example, a library of double crossovers may include all combinations of the three parents crossed over at positions 64 and 122. Alternatively, a library of triple crossovers may include examples of all three parents crossed over at positions 64, 122, and 166. Alternatively, as described in more detail below, a library of seven crossovers will allow crossovers to occur at each of the seven listed positions. As discussed herein, any number of crossovers is possible; for example, 1-5, 5-10, 10-20, 20-30, 30-50, 50-70, 70-90, 90-150, or more crossovers. In one embodiment, the library contains some chimeras with one crossover and some with more than one crossover; thus, chimeras with various numbers of crossovers can exist in a single library. In one embodiment regions of crossover interest are defined. Thus, if residue 64 is selected for a crossover position, residues flanking this residue may also be crossover positions, for example, 63, 60, 65, and 71. Thus, in one embodiment, not only are particular crossover points selected, or used, but regions for crossovers are selected. Generally, regions will be smaller than 30 residues on each side of the position identified, e.g., for position 64, a region may encompass 34-94; however, regions may vary depending upon the particular protein. In one embodiment, the size of the region is 30-25, 25-20, 20-15, 15-10, 10, 10-5, 5-1 residues on either side of the crossover point.

Definitions:

Unless defined otherwise herein, all technical and scientific terms used herein have the same meaning as commonly understood by one of ordinary skill in the art to which this invention belongs. Singleton et al. (2001) Dictionary of Microbiology and Molecular Biology, third edition, John Wiley and Sons (New York), and Hale and Marham (1991) The Harper Collins Dictionary of Biology, Harper Perennial, N.Y. provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "identical" in the context of two nucleic acid or polypeptide sequences refers to the residues in the two sequences that are the same when aligned for maximum correspondence over a specified comparison window. When percentage of sequence identity is used in reference to proteins or peptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. When such "corrections" are made, this is can be referred to as sequence similarity. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11-17 (1988) e.g., as implemented in the program PC/GENE (Intelligenetics, Mountain View, Calif., USA).

An "E" value is a term denoting the number of amino acid interactions (or contacts) that are predicted to be disrupted in a particular chimera. In one embodiment, this number is calculated through the use of SCHEMA and a disruption is counted anytime two points that were interacting, are now more than a certain, set, distance apart, for example, greater than 4.5 angstroms apart. In one embodiment this is achieved through a contact matrix. Each residue within a certain distance of each residue of a parent protein will be included as a contact or interaction in the parent. Then, each amino acid that is changed in the chimera will result in the breaking of those contacts that were associated with that amino acid. Thus, in this embodiment, the E value is the sum of those contacts that are broken, as defined as those contacts for each changed amino acid residue. As appreciated by one of skill in the art, other algorithms based on pair-wise interactions may be used. As discussed below, other distances may also be used. In one embodiment, other systems or programs may be used to establish changes in amino acid interaction number. In one embodiment, any measure of structural disruption may be used. In one embodiment, the parent structure that is used to compare to the predicted structure is a known or solved structure, for example, the CYP102A1 structure. In another embodiment, a predicted structure of a parent is used to determine disruptions in a resulting chimera from that parent. In one embodiment, the E value may be weighted according to the importance of the particular residue.

A "m" value is the number of mutations that the resulting chimera has, in relation to the closest parent. In other words, it is the number of residues that is different between the closest related parent and the chimera. In one embodiment, this is any change from identity. In another embodiment, this is any change from amino acid similarity. The possible ranges for m will depend upon the nature of the chimera and can be determined by one of skill in the art. For example, for all possible double-crossover chimeras the range of m values is 1 to 67 (although the number can be 0 if measured at the nucleotide level). However, in one embodiment, for a 7-crossover library, the range could be 7 to 103. The minimum number of mutations can be set to any number desired, for example, 1-2, 2-4, 4-6, 6-8, 8-10, 10-15, 15-20, 20-30, 30-40, 40-60, 60-70, 70-90, 90-100, or more. Similarly, the maximum number of mutations in any library can also be set to any number—limited only by the maximum number of mutations achievable through the recombination of the parents. Thus, for example, the maximum number of mutants may be 1-2, 2-4, 4-6, 6-8, 8-10, 10-15, 15-20, 20-30, 30-40, 40-60, 60-70, 70-90, 90-100, 100-150, 150-200, 200-300, or more.

A chimera is a combination of at least two segments of at least two different parent proteins. As appreciated by one of skill in the art, the segments need not actually come from each of the parents, as it is the particular sequence that is relevant, and not the physical nucleic acids themselves. A chimeric P450 will have at least two segments from two different parent P450s. The two segments are connected so as to result in a new P450. In other words, a protein will not be a chimera if it has the identical sequence of either one of the parents. Chimeras can be created from two or more P450 enzymes or a suitable equivalent of a P450 enzyme. A chimeric protein can comprise more than two segments from two different parent proteins. For example, there may be 2, 3, 4, 5-10, 10-20, or more parents for each final chimera or library of chimeras. The segment of each parent enzyme can be very short or very long, the segments can range in length of contiguous amino acids from 1 to the entire length of the P450 protein. In one embodiment, the minimum length is 10 amino acids. In one embodiment, a single crossover point is defined for two parents. The crossover point defines where one parent's amino acid segment will stop and where the next parents amino acid segment will start. Thus, a simple chimera would only have one crossover point where the segment before that crossover point would belong to one parent and the segment after that crossover point would belong to the second parent. In one embodiment, the chimera has more than one crossover point. For example, 2, 3, 4, 5, 6, 7, 8, 9, 10, 11-30, or more crossover points. How these crossover points are named and defined are both discussed below. In an embodiment where there are two crossover points and two parents, there will be a first contiguous segment from a first parent, followed by a second contiguous segment from a second parent, followed by a third contiguous segment from the first parent. Contiguous is meant to denote that there is nothing of significance interrupting the segments. These contiguous fragments are connected to form a contiguous amino acid sequence. For example, a P450 chimera from CYP102A1 (hereinafter "A1") and CYP102A2 (hereinafter "A2"), with two crossovers at 100 and 150, could have the first 100 amino acids from A1, followed by the next 50 from A2, followed by the remainder of the amino acids from A1, all connected in one contiguous amino acid chain. Alternatively, the P450 chimera could have the first 100 amino acids from A2, the next 50 from A1 and the remainder followed by A2. As appreciated by one of skill in the art, variants of chimeras exist as well as the exact sequences. Thus, not 100% of each segment need be present in the final chimera if it is a variant chimera. The amount that may be altered, either through additional residues or removal or alteration of residues will be defined as the term variant is defined. Of course, as understood by one of skill in the art, the above discussion applies not only to amino acids but also nucleic acids which encode for the amino acids.

A library is "optimized" when there is a high number of proteins in the library that have a high likelihood of folding, an increased degree of activity or altered activity, such as activity on a new substrate. A protein that is in this library is considered to be an optimized protein or enzyme. In one embodiment, a library is optimized when the percent of folded proteins in the library is greater than the percent of folded proteins in a randomly generated library. In another embodiment, the percent of folded proteins in an optimized library is at least 1-5, 5-10, 10-20, 20-30, 30-50, 50-70, 70-90, 100-110, 110-200, 200-400, or more, percent greater than a library randomly generated. In one embodiment, a library is optimized when the E value of the members of the library have an average value of less than 40 as determined through a SCHEMA analysis, for example, 40-35, 35-30, 30-25, 25-20, 20-15, 15-10, 10-5, 5-0.

In an alternative embodiment, a library is optimized when an E value is assigned to the members of a library. Thus, not all or a set percentage of the members of the library need to be folded or display improved or alternative functionalities.

One method of characterizing optimized libraries is through the use of a $F_{30}$ value. The F stands for "folded" and the "30" denotes that one is examining the percent folded as defined by those proteins with an E value of 30 or less, which, as described below, is an indicator that the protein will properly fold. Thus, if a library has a $F_{30}$ of 75%, it means that 75% of the proteins in the library are predicted to fold because their E value is less than 30. A <m> value is the number of mutations that a chimera has compared to its closest parent. Similarly, a $<m>_{30}$ shows the average level of mutation in chimeras with an E of <30. Thus, a high $m_{30}$ would suggest that there are a large number of mutations in chimeras, where the chimeras have an E value less than 30.

The proteins of the present invention further include "conservative amino acid substitution variants" (i.e., conservative) of the proteins herein described. As used herein, a conservative variant refers to at least one alteration in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can often be altered, for example to render the peptide more hydrophobic or hydrophilic, without adversely affecting the biological activities of the protein.

The proteins of the present invention are preferably in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein.

Homology or identity at the amino acid or nucleotide level is determined by BLAST (Basic Local Alignment Search Tool) and by ClustalW analysis using the algorithm employed by the programs blastp, blastn, blastx, tblastn and tblastx (Karlin et al., Proc. Natl. Acad. Sci. USA 87, 2264-2268 (1990); Thompson et al., Nucleic Acids Res 22,4673-4680 (1994); and Altschul, J. Mol. Evol. 36, 290-300 (1993), fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases (see Altschul et al., (1994) Nature Genetics 6, 119-129 which is fully incorporated by reference). The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89, 10915-10919, fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

"Stringent conditions" are those that (1) employ low ionic strength and high temperature for washing, for example, 0.5 M sodium phosphate buffer at pH 7.2, 1 mM EDTA at pH 8.0 in 7% SDS at either 65° C. or 55° C., or (2) employ during hybridization a denaturing agent such as formamide, for example, 50% formamide with 0.1% bovine serum albumin, 0.1% Ficoll, 0.1% polyvinylpyrrolidone, 0.05 M sodium phosphate buffer at pH 6.5 with 0.75 M NaCl, 0.075 M sodium citrate at 42° C. Another example is use of 50% formamide, 5.times.SSC (0.75 M NaCl, 0.075 M sodium citrate), 50 mM sodium phosphate at pH 6.8, 0.1% sodium pyrophosphate, 5× Denhardt's solution, sonicated salmon sperm DNA (50 µg/ml), 0.1% SDS and 10% dextran sulfate at 55° C., with washes at 55° C. in 0.2×.SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

Embodiments of the present invention further include fragments of any one of the encoding nucleic acids molecules. As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, fluorescent-labeled, biotin -labeled, radio-labeled nucleotides and the like. A skilled artisan can employ any of the art known labels to obtain a labeled encoding nucleic acid molecule.

A. Selection of Optimized P450 Chimeras through Recombination and Analysis

In order to verify that E and m values were accurate indicators for folding, functionality and novel functionality, a library of chimeric P450 enzymes was created from two parent P450s. CYP102A1 and CYP102A2, homologs from *Bacillus megaterium* and *Bacillus subtilis*, respectively were selected as parents from which to construct the chimeras. (Narhi et al., Biochem Biophys Res Commun 116, 851-858 (1983); Gustafsson et al., Biochemistry 43:5474-5487 (2004)). Their 64% nucleotide identity places them below the limits for effective recombination using annealing-based (DNA shuffling) methods. (SEQ ID NO: 1 and SEQ ID NO: 3 for nucleic acids sequences, and SEQ ID NO: 2 and SEQ ID NO: 4 for amino acid sequences respectively). It is generally acknowledged that for effective recombination (effective recombination means non-biased crossover locations, low fraction of parental sequences, full assembled sequences, limited stop codons, insertions and deletions) the limit is 70% (Lutz, et al., *Proc Natl Acad Sci USA* 98:11248-11253 (2001); and Neylon, C., Nucleic Acids Res 32:1448-1459 (2004)).

These soluble fusion proteins, consisting of a catalytic heme-domain and an FAD- and FMN-containing NADPH reductase require dioxygen and an NADPH cofactor to catalyze substrate hydroxylation. ((Munro et al., Trends Biochem Sci 27, 250-257 (2002)). However, the heme domain can utilize hydrogen peroxide via the 'peroxide shunt' pathway for catalysis. While this 'peroxygenase' activity is low in CYP102 µl, it is enhanced by the amino acid substitution F87A; the equivalent F88A mutation in CYP102A2 has a similar effect. (Li et al., FEBS Lett 508, 249-252 (2001); Cirino et al., Advanced Synthesis & Catalysis 344, 932-937 (2002)). The P450 chimeras were constructed from the genes for the heme domains of CYP102A1 with the F87A mutation and CYP102A2 with the F88A mutation. With these mutations, one can use the peroxygenase activity of the heme domain to explore the substrate specificities of the chimeras, without having to supply the reductase or cofactor.

As a test model, all possible sequences for the double crossover combinations of CYP102A1 and CYP102A2 were determined, with the limitation that any crossover result in an insert, or amino acid distance between crossovers, of at least 10 amino acids in length. Following this, E values and m values (mutation number) were determined for each chimera. The distribution in the levels of disruption (E) and effective mutation (m) for this population of chimeras can be seen in FIG. 1. The E value was determined through the use of SCHEMA. In one embodiment any type of P450 is contemplated for recombination and the production of a chimera. In one embodiment, chimeric P450s are produced from members of the CYP102 family. In another embodiment, chimeric P450s are produced from the CYP102A, family. In another embodiment, the parents selected for recombination are CYP102A1, A2, and A3.

The E values for the examples described below were calculated as any disruptions that resulted in the chimera as compared to the CYP102A1 parent, as the crystal structure of this parent has been solved. In one embodiment the cutoff distance is selected from the following: 0-2, 2-3, 3-4, 4-5, 5-6, and 6-10 Å.

By comparing SCHEMA disruption predictions to functional beta-lactamases selected from a large library of chimeric sequences, it was found that sequences retaining the parental protein fold and function tend to have low E values. (Meyer et al., Prot. Sci., (2003)). In fact, the probability of the beta-lactamses retaining function decreased exponentially as E increased. Based on the structure of the parent proteins, SCHEMA determines which residues are interacting, defined as those residues within a cutoff distance, and generates a contact a matrix. When recombining two parents, for example, the contacts are scaled by the sequence identity of the parents being recombined, i.e., all contacts which cannot be broken by recombination are removed from the matrix. E is determined by counting the number of contacts broken when a chimeric protein inherits portions of its sequence from different parents.

The effective levels of mutation "m" in one embodiment is the Hamming distance from the closest parent. As is known, the Hamming distance is a measure of the difference between two strings, such as sequences. The distance is expressed by the number of characters that need to be changed to obtain one string from the other.

E values for the different chimeras were computed using the high-resolution structure for CYP102A1 with palmitoglycine bound in the active site (Haines et al., Biochemistry 40, 13456-13465 (2001)). Because previous studies have shown that substrate binding causes a large conformational change in CYP102A 1, E was also calculated using the substrate-free CYP102A1 structure. (Paulsen et al., Proteins 21, 237-243 (1995); Modi et al., Nat Struct Biol 3, 414-417 (1996); Li et al., Nat Struct Biol 4, 140-146, (1997), Ravichandran et al., Science 261,731-736 (1993)). As shown in Table 1, similar E values were obtained for the two calculations. Because both parents contain the same heme cofactor, contacts between the heme and the protein will not be broken upon recombination, at least in this particular model. It is assumed that chimeras retain parental heme contacts, and heme is not included in the calculation of the E value. In one embodiment, these contacts are allowed to be broken. This could be achieved by altering the particular structural data, or by performing recombination with a protein that has such different connection between the heme and the protein, as well as other methods appreciated by one of skill in the art.

TABLE 1

Designed CYP102A1-CYP102A1 Chimeric P450s

| Chimera[a] | E (substrate-bound)[b] | E (substrate-bound)[b] | m[c] | Folded (λ max)[d] | T[m] (° C.) | Peroxidase activity[f] |
|---|---|---|---|---|---|---|
| CYP102A1 | — | — | — | yes (448) | 55 | 2.6 |
| CYP102A2 | — | — | — | yes (449) | 44 | 0.4 |
| 364-403 | 2 | 2 | 13 | yes (449) | 51 | 1 |
| 165-256 | 7 | 7 | 36 | yes (449) | 48 | 16.1 |
| 165-256M | [7] | [7] | 36 | yes (448) | 50 | 3.5 |
| 285-341 | 10 | 9 | 19 | yes (448) | 53 | 2.1 |
| 191-335 | 12 | 12 | 50 | yes (449) | 40 | N.D. |
| 169-197 | 12 | 10 | 11 | yes (449) | 52 | 100.3 |
| 169-197M | [12] | [10] | 11 | yes (449) | 43 | 0.3 |
| 65-256 | 15 | 13 | 61 | yes (447) | 36 | N.D. |
| 118-194 | 20 | 19 | 20 | yes (449) | 47 | 34.3 |
| 70-299 | 21 | 19 | 70 | yes (448) | 42 | 0.8 |
| 46-73 | 27 | 30 | 16 | yes (448) | 55 | 6.8 |
| 277-365 | 27 | 28 | 33 | yes (421) | 39 | N.D. |
| 43-135 | 34 | 38 | 33 | yes (448) | 53 | 6.8 |
| 186-365 | 34 | 35 | 65 | no | — | N.D. |
| 186-365M | [34] | [35] | 65 | no | — | N.D. |
| 50-140 | 38 | 39 | 32 | yes (448) | 52 | 10.4 |
| 345-448 | 42 | 43 | 34 | no | — | N.D. |

[a]Chimera names correspond to the first and last residue of CYP102A2 inserted into CYP102A1 according to the numbering of CYP102A1. "M" indicates mirror chimeras were CYP102A2 is inserted into CYP102A2.
[b]SCHEMA-calculated disruption using substrate-bound structure (1JPZ) and substrate-free structure (2HPD). Brackets [ ] indicate assumed disruption for mirror chimeras (due to lack of crystal structure of CYP102A2).
[c]Effective level of mutation, relative to closest parent.
[d]Folding as assayed by reduced CO difference spectroscopy. λmax for Soret band is reported.
[f]Values report in nmol product/nmol P450/min. Activities <0.2 were not detectable (N.D.).

In one embodiment, the E values used for characterization and analysis are the substrate free E values. In another embodiment, the E values used are the substrate bound E values. In yet another embodiment, the E values are a derived from a weighted average of the bound and unbound E values. In situations in which a protein exists in multiple states, conformations, or binds to different substrates, each conformation may be accorded its own appropriate E value or they may all be averaged together. In one embodiment, an appropriate E value may be selected based on the desired activity and structure associated with that activity. Thus, E values determined for a protein in a conformation that is similar to the desired conformation of the protein, may be selected over other possible E values for the protein.

Figure 5:
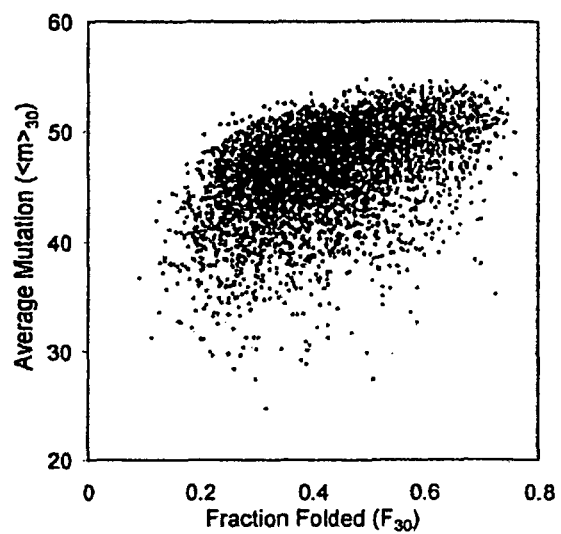
FIG. 5 is a graph displaying a theoretical library analysis.

Once a particular set of crossover positions has been selected, it is useful to select a subset of the possible chimeras so that the chimeric sequences can be made and tested (for two parents, this is $2^3=8$ sequences, including the parental ones). As appreciated by one of skill in the art, in generating large libraries that incorporate multiple crossovers, reducing disruption becomes an important design criterion. For example, FIG. 5 shows an in silico analysis of 5,000 different libraries in which 10 randomly-selected crossovers were allowed between CYP102A1 and CYP102A2, with the crossover positions chosen at random. Each library contains $2^{11}=2,048$ different chimeric sequences. For each library, two values were calculated, i) the fraction that is predicted to fold ($F_{30}$=fraction of sequences with E≤30) and ii) the average level of effective mutation in these folded chimeras ($<m>_{30}$=average level of effective mutation in those chimeras with an E less than/equal to 30). The data demonstrates that the choice of crossover points can dramatically affect these values and the distribution and nature of functional proteins in the library.

In one embodiment, the library is constructed from at least two parent proteins. For example, 3, 4, 5, 6-10, 10-50, or more proteins may be used as starting parents. Additionally, the minimum size of each crossover point and the frequency of the crossovers may also be altered. In one embodiment, the minimum size of a crossover section is limited to what is experimentally practicable through recombination. In another embodiment, the minimum size of the crossover section is selected from the following: 1, 2, 3, 4, 5, 6, 7, 8, 9, 10, 11-15, 15-20, 20-30, or more amino acids. The number of times that a crossover occurs can also be a factor to consider. In one embodiment, the number of times there is a crossover in a chimera is selected from the following: 1, 2, 3, 4, 5, 6, 7, 8, 9, 10, 11-15, 15-20, 21-30, 31-50, and 50-100. The advantage of increasing the parent number, shrinking the size of the crossover segment, or increasing the number of times that a crossover may occur is that these will increase diversity of the final chimera. One disadvantage is that such calculations will require more computational resources. Another disadvantage is it increases the library size so one may not find a protein with the properties one desires. As such, the selection of these possible variables will depend upon how much diversity one wishes in the final library. As appreciated by one of skill in the art, these values, and the importance of selecting these values, will also depend, to some extent, upon the amount of sequence similarity between the parents. For example, when two parents are very dissimilar, there is a greater chance of having a library of diverse chimeras and so the number or crossovers may be decreased and the size of the crossovers may be increased accordingly. Another factor in deciding the above variable is the desired size of the final library of chimeras. If a large library is desired, then the values can be adjusted accordingly, likewise, if a smaller library is desired.

A library of CYP102A1 and CYP102A2 chimeras may contain as little as 9% that fold properly; on average 42% will fold. In contrast, by constructing libraries in silico and using SCHEMA to guide the choice of crossover points, the percentage folded can be as high as 76%, and a very high effective level of mutation can be retained (with >50 mutations on average per folded sequence). For example, see FIG. 5, showing that particular libraries display both a high mutation number and have a large percentage of their chimeric population with E values under 30, thus demonstrating that they are most likely folded. This latter library is richer in novel functional proteins than libraries made at random. There will be greater benefits of using SCHEMA when recombining more parents or parental sequences with less sequence identity than those studied here.

In developing libraries, different P450 enzymes may be used. In one embodiment, the degree of identity between the P450 enzymes is less than 70%. In another embodiment the degree of identity between at least two of the P450 enzymes is less than 99% identity, for example, 10-30, 30-50, 50-60, 60-70, 70-90, 90-99, 30, 40, 50, 55, 60, 61, 62, 63, 64, 65, 66, 67, 68, 69, 70, 80, 90, and 95 percent identity. In another embodiment, similarity, rather than identity is used. Thus, amino acids that have similar functional characteristics (e.g., positive charges or hydrophobicity) may be freely exchanged for one another in this analysis. Of course, similarity would be determined at for the encoded for amino acid of the nucleic acid.

In one embodiment, once the libraries discussed above, or the proteins discussed below, are created, additional mutagenesis and further rounds of evolution on the proteins can be applied to create further improved proteins or proteins with alternative novel activities. Thus, in one embodiment, proteins or libraries using these determined proteins or libraries as starting material are contemplated.

B. Chimeric Protein Creation and Folding

As mentioned above, the combination of SCHEMA and recombination resulted in a high percentage of optimized chimeric P450s. Additionally, recombination, guided by the SCHEMA, yielded specific chimeras, with detectable activity on specific substrates analyzed. It also yielded chimeras that were broadly-specific enzymes that hydroxylated multiple substrates, including substrates that are novel to the parent P450s.

Figure 2:
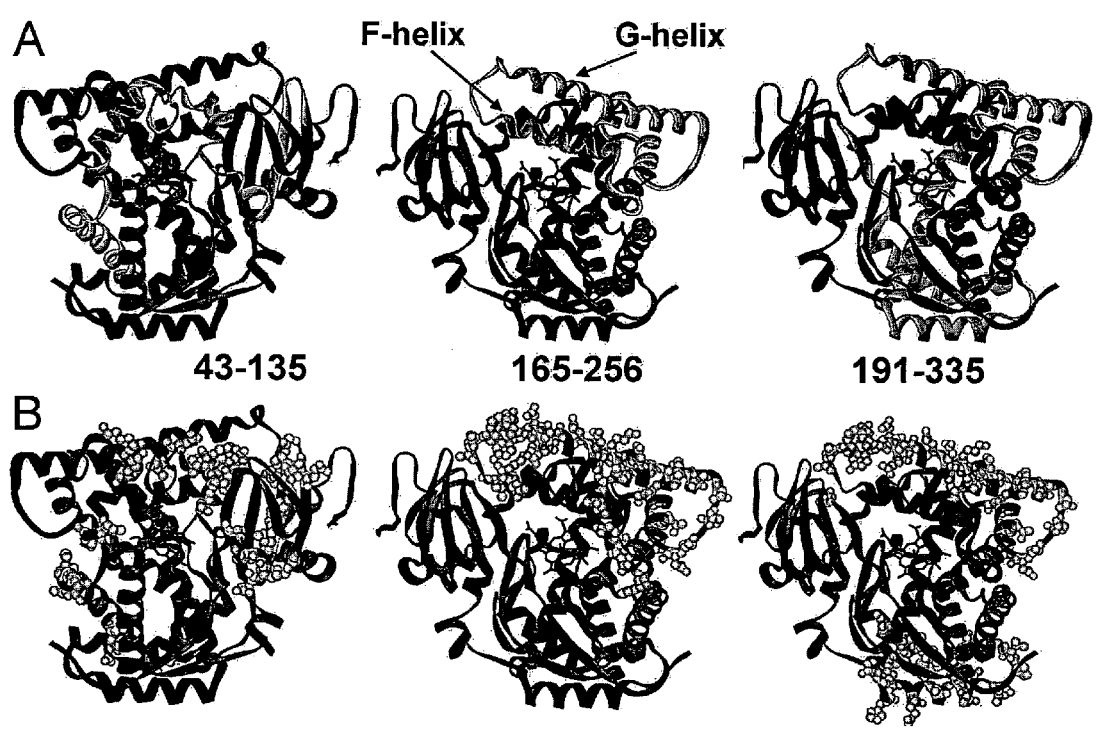
FIG. 2A is an illustration displaying the structural models of chimeric cytochrome P450s denoting the F and G-helix.
FIG. 2B is an illustration displaying the structural models of chimeric cytochrome P450s and demonstrating the mutated residues of interest.

In order to determine the efficiency and accuracy of the library in predicting optimized P450 chimeras, several of the predicted chimera structures were generated and tested. Fourteen chimeras that encompass a broad range of E values (2 to 42) and m values (11 to 70) were chosen for construction (Table 1). Both 'mirror' sequences, i.e., chimeras that derive sequences from opposite parents at every position (designated by M) and the predicted sequences were generated for three of these positions. The other eleven sequences were CYP102A 1 with an internal segment derived from CYP102A2. The tested chimeras are as follows: 277-365 (SEQ ID NO: 5), 65-256 (SEQ ID NO: 6), 169-197M (SEQ ID NO: 7), 70-299 (SEQ ID NO: 8), CYP102A1 (SEQ ID NO: 2), CYP102A2 (SEQ ID NO: 4), 364-403 (SEQ ID NO: 9), 169-197 (SEQ ID NO: 10), 285-341 (SEQ ID NO: 11), 118-194 (SEQ ID NO: 12), 165-256M (SEQ ID NO: 13), 50-140 (SEQ ID NO: 14), 165-256 (SEQ ID NO: 15), 191-335 (SEQ ID NO: 16), 43-135 (SEQ ID NO: 17), and 46-73 (SEQ ID NO: 18). The swapped fragments encompass a variety of non-trivial structural elements, as seen in the three example chimeras whose structures are shown in FIGS. 2A and 2B. FIG. 2B shows the mutations mapped onto the CYP102A1 structure are the chimera residues from CYP102A 1 and CYP102A2 in dark gray and light gray, respectively (Haines et al., Biochemistry 40, 13456-13465 (2001)). FIG. 2B shows that, unexpectedly, most of the effective mutations in the chimeras (shown in white) are located on the surface of the protein.

In one embodiment, both trivial and nontrivial elements may be exchanged between parents. In another embodiment, only the nontrivial or the trivial elements can be exchanged. In one embodiment, the point of insertion of the first segment into the second segment results in a change in the chimera that is different from both parents. In another embodiment, the insertion of the second segment does not, itself, result in a new mutation at the point of insertion, but the resulting chimera has at least one amino acid mutation that makes the chimera different from both parents. In one embodiment, the mutation is different based on identity. In another embodiment, the mutation is different based on similarity.

As appreciated by one of skill in the art, the particular number of mutations that is introduced need not be limited to any number. However, as discussed herein, the larger the m value, the greater the likelihood that the chimera will have a novel functionality. Thus, in one embodiment, when such diverse functionality is desired, the protein, or library of proteins, will involve those predicted chimeras that have an m value of at least one of the following: 15, 16-20, 21, 22, 23, 24-28, 29, 30, 31, 32, 33, 34, 35, 36, 37, 38, 39, 40, 41-50, 51-60, 61-75, 75-90, 90-110, and greater. In one embodiment, chimeras with an m value of 1-4, 4-6, 6-10, and 10-15 will be predicted to be functionally diverse. In one embodiment, the cutoff for the m value is determined experimentally, with the aid of the data shown in FIG. 1, for example. In one embodiment, an alteration in sequence will count towards a "m" value if the new amino acid is not identical to the old amino acid. In another embodiment, an alteration in sequence will only count towards a "m" value if the parent and final amino acid are not similar. As appreciated by one of skill in the art, the second segment of the chimera need not be inserted between sections of the first segment.

The chimeras can be created in any number of ways. For example, the chimeras can be constructed using SOEing cloned into the IPTG-inducible pCWori vector, and can be sequenced to confirm the absence of point mutations. (Horton et al., Gene 77,61-68 (1989), Barnes et al., Proc Natl Acad Sci USA 88, 5597-5601 (1991)). All proteins can be overexpressed in a catalase-free strain of *E. coli*, which allows the peroxygenase activity of the heme domains to be monitored directly in cell extracts. (Nakagawa et al., Biosci Biotechnol Biochem 60, 415-420 (1996), Cirino, P. C., and Arnold, F. H., Angew Chem Int Ed Engl 42:3299-3301 (2003)).

Structural Determinations

Figure 3:
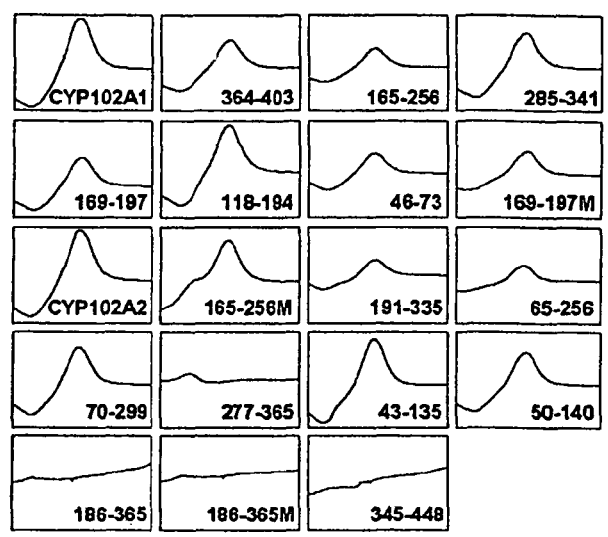
FIG. 3 is an assembly of CO spectra for CYP102A1-h, CYP102A2-h and their heme domain chimeras.

Carbon monoxide difference spectroscopy was used to assess the level of structural disruption in the chimeras created. A reduced CO spectrum producing a Soret band near 450 nm is indicative of heme incorporation and thus a correctly-folded P450. (Omura et al., J. Biol. Chem 239, 2370-2378 (1964)). A Soret band near 420 nm is indicative of a P450 that is folded, but inactive due to disruption of the heme environment. (Martinis et al., Biochemistry 35,14530-14536 (1996), Wells et al., Biochemistry 31, 4384-4393 (1992)). Fourteen chimeras displayed detectable Soret bands; one appeared at 420 nm (FIG. 3, displaying the reduced CO-difference spectra for CYP102 µl, CYP102A2, and their chimeras, top left to right, CYP102A1, 364-403, 165-256, 285-341, 169-197, 118-194, 46-73, 169-197M, CYP102A2, 165-256M, 191-335, 65-256, 70-299, 277-365, 43-135, 50-140, 186-365, 186-365M, 345-448). Spectra were taken from 400 to 500 nm. The absorbance range for the first two rows is −0.5 to 0.6, the third and fourth rows are magnified 3× with a range of −0.17 to 0.2, and the last row is magnified 40× over the first row. Most chimeras exhibited a Soret band at 450:1:3 nm, characteristic of a folded P450 with correctly incorporated heme cofactor. Chimera 277-365 showed a Soret band at 420 nm, and no Soret band could be detected for chimeras 186-365, 186-365M and 345-448.

Chimeras with low calculated disruption (E value) were most likely to retain folded structures: all with E<30 were folded, but less than half with E>30 yielded detectable Soret bands (Table 1).

As appreciated by one of skill in the art, other structural determinations may be made in order to determine if a P450 chimera is properly folded. For example, crystallography or tests on functionality, as described below.

C. Analysis of the Predictive Ability of the Chimera Library for Functionality

Figure 4:
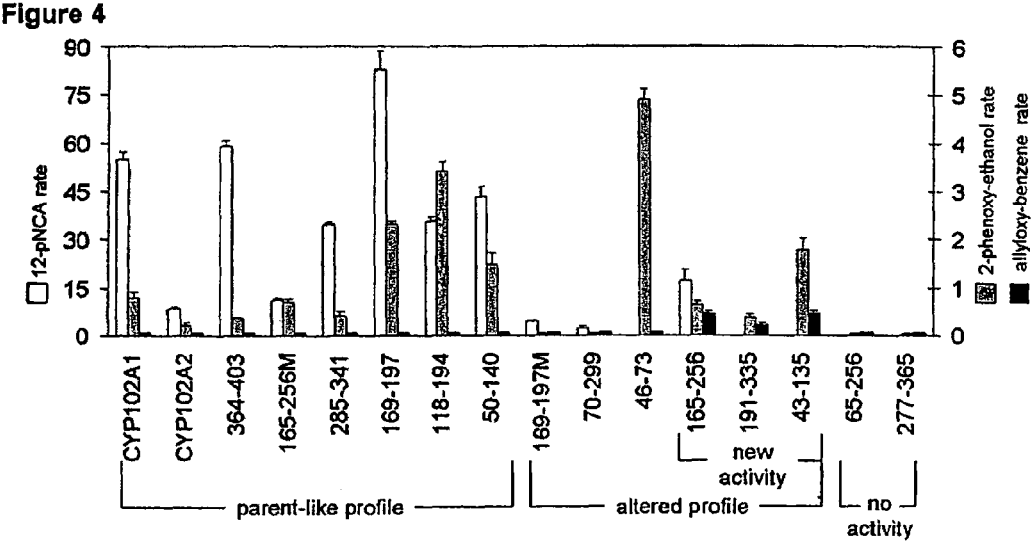
FIG. 4 is a graph displaying the substrate activity profiles of CYP102A1, CYP102A2 and the folded chimeras.

The activity of selected chimeras from the library was examined in order to verify that the library's predictive properties were accurate. The chimeras generated from the above library, and selected for functional testing, demonstrated that the library produced many fully functional and even more fully folded proteins. Additionally, the resulting chimeras displayed surprising and unexpected properties. One specialist chimera (46-73) displayed a 6-fold higher peroxygenase activity with 2-phenoxy-ethanol than the parent most active on that substrate (CYP102A1), Table 1. Three of the chimeras displayed novel hydroxylase activity on allyloxy-benzene, which is not detectable in either of the parent enzymes. One chimera demonstrated perioxidase activity up to 40 fold of the original parent. Surprisingly, residues that appear to be functionally neutral in the parent proteins are able to confer altered properties when recombined, provided the novel sequence folds properly. More than half the folded P450 chimeras surpassed the parents in peroxidase or peroxygenase activity. In addition, nearly half of the folded chimeras had altered substrate specificities relative to the parents (FIG. 4).

FIG. 1 shows how chimera function is related to calculated disruption and effective mutations. Disruption values for all double-crossover chimeras with a minimum insert size of 10 amino acids between CYP102A 1 and CYP102A2 were determined using the structure for CYP102A1. Disruption values from the substrate-bound structure were used. For all double-crossover chimeras, the average Eis 23.5±12.8, and average mutation m is 40.6±22.6. The 17 constructed chimeras were assayed for the ability to fold and hydroxylate 12-pNCA, 2-phenoxy-ethanol and allyloxy-benzene: Squares represent chimeras that retain the ability to fold, and X's indicate those that did not. Chimeras that fold but have no detectable peroxygenase activity (□), chimeras with parent-like substrate specificity profiles (■), chimeras with altered profiles (▨ larger diagonals, ▩ thinner, more numerous diagonals), chimeras with new activity on allyloxy-benzene (▨ larger diagonals). The methods for testing these substrates are discussed in greater detail below and in Otey et al. (Chemistry and Biology, 11:309-318 (2004)). Among the folded chimeras, those with substrate activity profiles similar to the parents typically cluster together with lower average mutation of <m>=22 than those with altered profiles <m>=37. Thus, it appears that chimeras with higher levels of mutation, provided they fold, are more likely to have altered properties, while those with lower levels of mutation tend to be more similar to the parents. Theoretical models predict that recombination facilitates fitness changes, but there is little information on how recombination mutation level relates to functional evolution. (Cui et al., Proc Natl Acad Sci USA, 99, 809-814, (2002), Bogarad et al., Proc Natl Acad Sci USA, 96, 2591-2595 (1999)).

The probability of retaining function in the P450 chimeras decreases as calculated disruption increases. P450 chimeras with as many as 50, 61, and 70 effective mutations were still able to properly incorporate a heme cofactor, provided the chimeras were sequences with low calculated disruption (typically E<30) (Table 1). This demonstrates that E is a useful measure of the ability of a chimeric P450 to retain its structure, and that SCHEMA-calculated disruption can anticipate structural and functional conservation in a larger and more complex protein than shown previously. Taking the experimental results and disruption calculations together, it is now possible to predict that a large fraction of all double-crossover chimeras of CYP102A1 and CYP102A2 will retain their structure as the average E value of the chimeras is less than 30 (FIG. 1). Thus, in one embodiment, a library of double crossovers between CYP102A 1 and CYP102A2 is an optimized library For most proteins sharing 63% amino acid sequence identity, a majority of the amino acid substitutions that separate them appear on the protein surface. Not surprisingly, therefore, most of the mutations in the chimeras are also found on the exterior of the protein. Such mutations are less disruptive, on average, than changes in the core. These mutations also lead to functional variations in the chimeras studied here, mutations distant from the active site alter substrate specificities and activities, as has been observed in previous random mutagenesis studies. (Zha et al., Chem. Commun. 24, 2664-2665 (2001), Zhang et al., Proc Natl Acad Sci USA 94, 4504-4509 (1997)).

Surprisingly, it was also discovered that the 'novel' activities on allyloxy-benzene and altered substrate-specificity profiles could not be attributed to specific residue alterations. Chimeras exhibiting similar changes in activity arose from swapping distinct polypeptides spread throughout the enzyme (FIG. 4). This illustrates that there are multiple ways to evolve functionally similar enzymes through homologous recombination.

D. Optimized Chimeric Proteins

The optimized P450 chimeras that are described within the libraries are encompassed within the present embodiments. In one embodiment, a P450 chimera is a protein with at least a segment of a sequence from one P450 protein and a second segment from a second P450 protein. When the two segments are connected, the result is a chimeric P450 protein. In one embodiment, the P450 protein is "optimized" when the E value of the combined sections is sufficiently low enough to be advantageous. Such an E value may be determined as described above, in silico, with very little effort required and as described herein. Similarly, a library is "optimized" when the members of the library have a minimal, or sufficiently low, E value. As discussed below, a "sufficiently low" value can vary depending on the circumstances.

"Sufficiently low" is defined in each situation and will depend upon the size of the desired library desired and other factors discussed herein and known to one of skill in the art; however, the appropriate E value in the above and below examples is 30. However, as can be seen in FIG. 1, the E value could be set at 40 as well. Additionally, the E value can be defined relative to other factors, such as mutation number (m value). For example, the E value can vary as a function of mutation number where higher mutation number requires a lower E number. In one embodiment, the E value or function is determined through the methods described herein to produce, for example, a graph similar to that shown in FIG. 1. In such a situation, an area on the graph may be defined as those chimeras that are optimized chimeras. In another embodiment, the E value is set as an E value equal to E values in similar functional chimeras.

In one embodiment, optimized P450 chimeras include CYP102A1/CYP102A2 chimeras with a sufficiently low E value. For example, some such proteins would be 364-403, 165-256, 165-256M, 285-341, 191-335, 169-197, 169-197M, 118-194, 70-299, 46-73, 43-135, and 50-140 wherein the numbers represent the A2 section replacing the identified section of A1, unless noted otherwise (i.e., "M" or mirrored sequences). In another embodiment, any folded P450 chimera is an optimized chimera, regardless of whether it exhibits activity on the particular substrates discussed herein, as long as the folded P450 exhibits activity on at least one substrate. For example, in this embodiment, the chimeras would include the above chimeras as well as chimeras 65-256 (SEQ ID NO: 6) and 277-365 (SEQ ID NO: 5).

In another embodiment, the chimera or library is optimized by comprising CYP102A1 and CYP102A2 chimeras. In one embodiment, the CYP102A1 and CYP102A2 proteins or libraries may have chimeras with one of or all of the following crossover positions: 364-403, 165-256, 165-256M, 285-341, 191-335, 169-197, 169-197M, 65-256, 118-194, 70-299, 46-73, 277-365, 43-135, 186-365, 186-365M, 50-140, and 345-448. A crossover position is defined as the position of transition between the first and the second protein. For example, there would be two crossover positions in each of the above constructs, for the 46-73 construct, there would be one cross over position at residue 45-46 and a second one at residue 73-74. In situations where only a single crossover number is given, the number represents the point at which the following amino acid is the other protein. Thus, 165-256 could also be represented as a crossover point at 164 and a crossover point at 256.

The P450 chimeras with the highest peroxidase and peroxygenase rates (169-197) and broadest substrate specificity (165-256) have both swapped a region of amino acids comprising the F helix. The new, favorable combination of the F helix from CYP102A2 and the G helix from CYP102A1 in chimera 169-197 and the complete substitution of the F and G helices in CYP102A1 with that from CYP102A2 in chimera 165-256 indicate a key role of this region in determining P450 catalytic properties.

In one embodiment, chimeric proteins, comprised of proteins other than the two P450 proteins, CYP102A1 and CYP102A2 are included as possible optimized P450 proteins, so long as the predicted E value of the protein is sufficiently low.

In one embodiment, the chimeras and libraries include other proteins or nucleic acids encoding proteins as well. In one embodiment, these other proteins or nucleic acids encoding proteins are fusion proteins. For example, one possible fusion protein would include a reductase from any of the parents (Gustafsson et al., Biochemistry 43:5474-5487 (2004); Munro et al., Trends Biochem. Sci. 27, 250-257 (2002)) or another P450 (Yabusaki et al., Biochimie 77:594-603 (1995); Fisher et al., Methods Enzymol 272, 15-25 (1996)). Alternatively, the other proteins can be expressed in the same culture and work as separate proteins (Miles et al., Biochem J 288 (Pt 2), 503-509 (1992)). One possible advantage of these combinations is that one can then demonstrate different properties due to the use of NADPH or NADH as an electron source rather than using the peroxide shunt pathway. The reaction can also be driven electrochemically (Estabrook et al., Methods Enzymol 272, 44-51 (1996); Fantuzzi et al., J Am Chem Soc 126, 5040-5041 (2004); Faulkner et al., Proc Natl Acad Sci USA 92, 7705-7709 (1995)).

In one embodiment, it is possible to use entire libraries or collections of optimized proteins together. Such a group may be very advantageous where individual chimeras each perform useful reactions or the group acts synergistically. By transforming with a mixture of plasmids containing all or part of the library, one can obtain a mixture of cells with a population of chimeras. The chimeric proteins can be extracted and used as a mixture of proteins, used within the cells as fusion proteins to a reductase domain, or used within the cell alongside a reductase domain expressed as a separate protein. In one embodiment, one use of such a combinatorial library as a whole is in the mobilization of oil where there exists a multitude of different aliphatic substrates. By introducing a group of diverse catalysts in the form of a combinatorial library that can chemically alter the heavy oil, one can solubilize certain substrates or create products that act as emulsifying agents. In this case, different chimeras could act on different substrates or perform chemistry at different chemical positions on any given substrate. In another embodiment, the combination is useful in bioremediation, where chemistry does not need to be specific and should just result in the breakdown of desired compounds, e.g., xenobiotics. Therefore, a group of catalysts could be introduced which assist in the degradation of these substrates using nonspecific chemistry. In another embodiment, within a whole cell, the chimeras will also act in the first catabolic step of breakdown of substrates for their use as energy or as a carbon source for further cell growth (Lamb et al., Biochem Biophys Res Commun 276:797-802 (2002)), thus proliferating the useful chimeras.

The following sections describe in more detail other characteristics of the optimized chimeric proteins and libraries thereof and how such characteristics can be examined.

Activity Assays

1. Peroxygenase Activities

The chimeras were assayed for hydroxylation of p-nitrophenoxydodecanoic acid (12-pNCA), a fatty acid analog that is hydroxylated by CYP102A1 and CYP102A2 to yield p-nitrophenolate (Schwaneberg et al., Anal Biochem 269,359-366 (1999)). Initial rates were measured using a concentration of 12-pNCA (250 μM) significantly higher than the $K_M$ of CYP102A1 for this substrate ($K_M$=8.1 μM. Li et al., Biochim. Biophys. Acta 1545:114-121 (2001)). Activities on 2-phenoxy-ethanol and allyloxy-benzene were also determined, using the 4-aminoantipyrine (4-AAP) assay, which is sensitive to phenols and catechols (Otey et al., High-throughput screen for aromatic hydroxylation. In Directed Enzyme Evolution: Screening and Selection Methods (2003), F. H. Arnold and G. Georiou, eds. (Totowa, N.J.: Humana Press), pp. 141-148). This assay yields a detectable product if hydroxylation occurs at the ortho- or meta-positions of the aromatic ring or when hydroxylation yields the hemiacetal, which decomposes to form phenol. When hydroxylation rates for the parent CYP102 enzymes were monitored using the maximum soluble concentrations of these substrates, activity could only be detected on 2-phenoxy-ethanol. Neither parent showed activity towards allyloxy-benzene.

FIG. 4 shows the rates and substrate activity profiles for each of the folded chimeras. Chimeras were assayed for peroxygenase activity on 12-pNCA, 2-phenoxy-ethanol and allyloxy-benzene. Chimeras can be grouped into four categories: those with parent-like profiles (activity on 12-pNCA and 2-phenoxy-ethanol), those with altered profiles relative to the parents, those with detectable activity on allyloxy-benzene, and those with no detectable peroxygenase activity. Rates are reported in nmol product/nmol P450/minute. Chimeras with no detectable activity are shown with values corresponding to the detection limits, which were 0.1, 0.06, and 0.08 for 12-pNCA, 2 phenoxy-ethanol and allyloxy-benzene, respectively. Chimeras lacking detectable CO binding spectra showed no activity on the substrates assayed. The chimeras that displayed parent-like profiles—although with different level of absolute activity, include, 364-403, 165-256M, 285-341, 169-197, 118-194, 20-140. Those with no activity include 65-256 and 277-365. Those with new activity include 165-256, 191-335, and 43-135. Those with altered activity include 169-197M, 70-299, and 46-73.

Unfolded chimeras showed no catalytic activity towards any substrate, and all but two that folded retained peroxygenase activity on at least one substrate. The P420 chimera was inactive towards all substrates tested. Several chimeric enzymes were more active than the best parent, CYP102A 1, on one or more substrate. Chimera 169-197 was the most active towards 12-pNCA, 46-73 had the highest activity on 2-phenoxy-ethanol, and 43-135 and 165-256 had the highest rates on allyloxy-benzene. One chimera, (165-256) displayed broadened specificity and was active on all three substrates. The remaining two (191-335 and 43-135) showed detectable activity on 2-phenoxy-ethanol and allyloxy-benzene, but not 12-pNCA.

2. Peroxidase Activities

P450s can reduce peroxide to water (and a proton) using a mechanism similar to that of peroxidases, although the intrinsic rate for P450s is many orders of magnitude slower. (Mansuy, D., Comp Biochem Physiol C Pharmacol Toxicol Endocrinol 121, 5-14 (1998)). It has been proposed that the earliest P450 function may have been as a peroxidase. (Gotoh, O., Cytochrome P450, 2nd Edition, pp. 255-272 (1993)). To investigate how recombination affects P450 peroxidase activity, the colorimetric substrate 2,2'-azino-bis(3-ethylbenzothiazoline-6-sulfonate) (ABTS) was used to monitor this reaction (Childs et al., Biochem J 145,93-103 (1975)). CYP102A1 and CYP102A2 heme domains both show low, but detectable peroxidase activity (Table 1). Chimeras 50-140, 118-194, 165-256 and 169-197 displayed significantly higher peroxidase activities, with 169-197 having the greatest increase (approximately 40fold higher than the most active parent). Mirror chimeras 169-197M and 165-256M did not show similarly enhanced levels of peroxidase activity. Three of the folded chimeras, 191-335, 65-256, and 277-335 showed no detectable peroxidase activity.

3. Thermostabilities

Thermostability was assayed by monitoring the loss of the Soret band at increasing temperatures. Chimera melting temperatures ranged from 36° C. to 55° (Table 1), with none more stable than CYP102A 1 (T m=55° C.). More than half of the folded chimeras were more thermostable than CYP102A2 (T m=44° C.); the rest were less stable. Chimeras that were less thermostable than the parents exhibited a wide range of E values, 12 to 27, and that stability does not correlate with calculated disruption, at least in this small population. However, thermostability may be important for retention of catalytic activity: the two chimeras that lacked peroxygenase activity were also the least thermostable.

EXAMPLES

Materials for Chimera Protein Production

Enzymes for DNA manipulations were from New England Biolabs (Beverly, Mass.) and Stratagene (La Jolla, Calif.). Synthetic oligonucleotides were from Invitrogen (Carlsbad, Calif.) or the California Institute of Technology oligonucleotide facility. DNA purification kits were from Zymo Research (Orange, Calif.) and Qiagen (Valencia, Calif.). Other reagents and chemicals were from Fisher Scientific (Pittsburgh, Pa.), Becton Dickinson (Franklin Lake, N.J.) and Sigma Chemical Co (St. Louis, Mo.).

Example 1

This example demonstrates how SCHEMA calculations can be applied to a library of recombined P450 enzymes of candidate chimeras. The initial library was produced by determining all possible double crossover points for the recombination of CYP102A1 and CYP102A2, with the caveat that each segment be at least 10 amino acids in length.

The sequences of CYP102A1 and CYP102A2 were aligned using ClustalW, revealing the existence of a one-amino acid insertion relative to CYP102A1, between Q229 and S230. (Thompson et al., Nucleic Acids Res 22, 4673-4680 (1994)). This insertion was ignored in the calculations. CYP102A1 residues G227 and E228 were also ignored because they are unresolved in the substrate-bound structure (1JPZ). The error values reported for E and m represent one standard deviation. Any distance between two residues greater than 4.5 angstroms was characterized as a disruption.

The number of contacts broken by the recombination (E) for each chimera was calculated using SCHEMA, using coordinates from the substrate-bound (1JPZ) and substrate-free (2HPD) structures of CYP102A1 (Voigt et al., Nat Struct Biol 9, 553-558 (2002), Haines et al., Biochemistry 40, 13456-13465 (2001), Ravichandran et al., Science 261:731-736 (1993)). Hydrogens, backbone nitrogens, backbone oxygens, and heme atoms were not included in the calculation.

The results can be seen in Table 1 and FIG. 1. As shown in the data in Table 1, various E values were generated for different crossovers. The E values varied from 2 to 42, just in the selected chimeras. Interestingly, E values did not vary to a huge degree between the substrate bound and substrate free complex. FIG. 1 displays the E and m values for all of the possible double crossover P450 chimeras. As can be observed in the figure, E values higher than 50 and m values close to 80 were observed. The average E value for all of the double crossover chimeras was 23.5±12.8 and the average m was 40.6±22.6.

Example 2

This example demonstrates how the nucleic acids encoding the chimeras generated in example 1 can be constructed. Selected chimeras were constructed using SOEing methods, as described previously (Horton et al., Gene 77,61-68 (1989)). Chimeras contained residues 1-463 from CYP102A1 or the corresponding residues in CYP102A2 (1-466). Two primers consisting of a 5' sequence from one parent (A) and a 3' sequence from the other (B) that encompass the crossover site were used to amplify the sequence to be inserted (B) with 25-30 b.p. overhangs from the other sequence (A).

The PCR protocol was to heat the plasmids and primers at 95° C. followed by 22 cycles of 95° C. for 1 minute, 48° C. for 1 minute, and 72° C. for 2 minutes with a final extension at 72° C. for 10 minutes. These products acted as primers in a further PCR reaction along with forward and reverse primers external to the ends of the gene containing BamHI and EcoRI restriction sites, respectively, for cloning into the pCWori vector. The PCR protocol was 95° C. for 1 minute, 46° C. for 1 minute, and 72° for 2 min for 22 cycles with a final extension at 72° C. for 10 minutes. These two products were assembled in a two-step PCR reaction: 95° C. for 1 minute followed by 14 cycles of 95° C. for 1 minute, 46° C. for 1 minute, and 72° C. for 2 minutes. External primers were added, followed by PCR 95° C. for 1 minute, followed by 14 cycles of 95° C. for 1 minute, 46° C. for 1 minute, and 72° C. for 2 minutes, with a final extension of 72° C. for 10 minutes. All PCR products were gel-purified using the Zymoclean-5 column from Zymo Research. High-fidelity Pfu Turbo and Pfu Ultra polymerases (Stratagene) were used for PCR. Final products were digested with BamHI and EcoRI and cloned into pCWori. Plasmids were transformed into a catalase-deficient strain of E. coli. The nucleic acids were then used to create the proteins described in Example 3.

Example 3

This example demonstrates how the chimeras can be expressed as protein. Chimeric P450s were expressed in catalase-deficient E. coli using the isopropyl-β-D-thiogalactopyranoside (IPTG)-inducible pCWori vector (Nakagawa et al., Biosci Biotechnol Biochem 60, 415-420 (1996), Barnes et al., Proc Natl Acad Sci USA 88, 5597-5601 (1991)). Cultures grown in terrific broth (TB) were shaken at 250 rpm and 30° C. until they reached an $OD_{600}$ of approximately 0.8. They were induced with 0.6 mM IPTG, supplemented with 25 μg/ml thiamine and 0.5 mM δ-aminoleuvulinic acid, and grown for 20 h at 180 rpm and 25° C. This procedure yields approximately 80 mg/L of P450 protein for CYP102A1 and CYP102A2. Cultures were pelleted at 5,500×g for 15 min, resuspended in 50 mM Tris (pH 8.2), and lysed by sonication. Centrifugation was used to clear the supernatant, which was used for further assays described in the following examples.

Example 4

This Example provides one method by which folding of a P450 enzyme may be characterized. Carbon monoxide reduced difference spectroscopy was performed as reported. (Schenkman et al., In Cytochrome P450 Protocols, Volume 107, I.R. (1998), Philips and E. A. Shephard, eds. (Totowa, N.J.: Human Press, Inc.), pp. 25-33). Cell extracts were diluted into 800 μL of 100 mM Tris buffer (pH 8.2) in a cuvette at room temperature. A few mg of sodium hydrosulfite on the tip of a spatula were added, and a blank spectrum was determined from 400 to 500 nm. Carbon monoxide was bubbled in for 20 seconds at a rate of approximately one bubble per second. Two minutes were allowed to pass before a spectrum was taken. Spectra were determined at multiple times to ensure complete carbon monoxide binding and maximum absorbance. There were no increases beyond 5 minutes of incubation with carbon monoxide for any of the chimeras. P450 enzyme concentrations were quantified for further assays using an extinction coefficient of 91 $mol^{-1}cm^{-1}$ for the absorbance difference between 448 nm and 490 nm. The results can be observed in FIG. 3 and in Table 1. As can be seen, 14 of the 17 constructs made exhibited the correct wavelength, indicating that they were properly folded. Additionally, every protein with an E value less than 34 demonstrated characteristics typical of folded P450 enzymes.

Example 5

This Example provides one method by which peroxygenase activity of a P450 enzyme may be characterized. First order rates for p-nitrophenolate accumulation were determined using 1 µM enzyme, 20 mM $H_2O_2$, 250 µM 12-pNCA and 0.5% dimethyl sulfoxide (DMSO) in 100 mM Tris-HCl (pH 8.2) at room temperature. Enzyme, substrate, buffer and DMSO were combined in a cuvette and zeroed at 410 nm. Reaction mixtures were incubated for 4 minutes and initiated by the addition of $H_2O_2$ to a final concentration of 20 mM. Initial rates were determined by monitoring the accumulation of p-nitrophenolate at 410 nm, and data from the first six seconds were used to determine initial rates. If no activity was observed at 20 mM $H_2O_2$, a second trial at 100 mM was done. No chimera inactive at 20 mM $H_2O_2$ showed activity at the higher concentration. The extinction coefficient of p-nitrophenolate is 13,200 $M^{-1}cm^{-1}$ (Schwaneberg et al., Anal Biochem 269:359-366 (1999)).

Rates on 2-phenoxy-ethanol and allyloxy-benzene were determined using 2 µM enzyme, 20 mM $H_2O_2$, 1% DMSO, and 1% acetone in 100 mM N-[2-hydroxyethyl]piperazine-N'-[3-propanesulfonic acid] (Epps) (pH 8.2) at room temperature. Substrate concentrations for 2-phenoxy-ethanol (100 mM) and allyloxy benzene (50 mM) maintained saturation. Reactions were initiated by the addition of $H_2O_2$ and quenched at appropriate times using an equal volume of a solution containing 4M urea and 100 mM NaOH. 120 µl of 0.6% 4-AAP was added, followed by mixing and addition of 120 µl of 0.6% potassium persulfate. Color was allowed to develop for 20 minutes before absorbance was read at 500 nm. Rates were determined from the linear region of the time course. The major products were determined by GC/MS to be the hemiacetal, which decomposes to phenol. The extinction coefficient for the 4-AAP/phenol complex was determined to be 4,800 $M^{-1}cm^{-1}$. The results can be seen in FIG. 4. Many of the chimeras displayed activity on 12-pNCA, 2-phenoxy-ethanol and allyloxy-benzene. Thus, the majority of those proteins that appear to have folded based on the results from Example 4, appear to be fully active P450s, and some, such as 165-256 191-335, and 43-135, appear to have gained novel activity on substrates that neither of the parents are effective upon. Additionally, the 169-197 chimera, while not gaining any novel activity, of those substrates examined, appears to have a significant increase in its ability to catalyze 12-pNCA.

Example 6

This example provides an example of how one can measure peroxidase activity. Initial rates of peroxidase activity were measured by monitoring the accumulation of the radical cation of ABTS at 414 nm (Childs et al., Biochem J., 145:93-103 (1975)). Enzyme (1 µM) was mixed with 10 mM ABTS in 200 mM phosphate buffer (pH 5.0) in a cuvette at room temperature. Samples were zeroed and reactions were initiated with the addition of $H_2O_2$ to a concentration of 20 mM. The absorbance at 414 nm was monitored for 5 minutes. Rates were determined from the steepest portion of the time course. An extinction coefficient of 36,000 $mol^{-1}cm^{-1}$ for ABTS was used.

Results can be seen in FIG. 4 and in Table 1. As can be seen from Table 1, 11 of 17 of the enzymes demonstrated peroxidase activity. Interestingly, several displayed activities that were much higher than either of the parents. For example, 165-256 had an activity at 16.1 (nmol product/nmol P450/min) and 169-197 had an activity of 100.3 (nmol product/nmol P450/min), both of these, as well as other chimeras, were much higher than the 2.6 and 0.4 of CYP102A1 and CYP102A2 respectively. Additionally, half of the P450s that lacked detectable peroxidase activity had E values above 33.

Example 7

This example demonstrates how one can measure the thermostability of a chimera. Cell extracts were heated in a thermocycler for 10 minutes at various temperatures, followed by cooling to 4° C. Extracts were centrifuged for 5 minutes at 3500×g to remove any precipitates. Carbon monoxide reduced difference spectroscopy was used to quantitate the amount of P450. The reduction of the carbon monoxide peak was monitored over a range of temperatures. The results can be seen in Table 1. As can be seen in Table 1, most of the chimeras displayed a greater thermostability than the CYP102A2 parent. However, they did not display a thermostability greater than the CYP102A1 parent.

Example 8

This example demonstrates how an optimized P450 chimera library can be generated and selected from numerous P450 libraries. This example also describes how to create optimized libraries and chimeras with three parents and with 7 crossover points. The libraries were generated in silico by randomly selecting 7 crossover points with a minimum fragment size or distance between crossovers of 20 amino acids for three P450s, CYP102A1 (SEQ ID NOS: 1 & 2), CYP102A2 (SEQ ID NOS: 3 & 4) and CYP102A3 (SEQ ID NO: 19 and SEQ ID NO: 20), and calculating every possible chimera from this set. The substrate-bound structure of CYP102A1 (1JPZ) was used to calculate the total number of contacts disrupted (E) and effective level of mutation (m) for all $3^8$ (6,561) chimeras in 5,000 libraries using CYP102A1, CYP102A2 and CYP102A3 as parents. These parental sequences all share roughly 64% amino acid identity with one another. The fraction of chimeras in each library with an E≤30, was denoted as a $F_{30}$ value, which reflects those that were predicted to fold based on the above information. The average effective level of mutation $<m>_{30}$ of this low-disruption fraction was also calculated.

Calculations were done as previously with some alterations to accommodate for three parents (Otey, et al., Chem Biol 11:309-318 (2004)):

$$E = \sum_i \sum_{j>i} C_{ij}\Delta_{ij}.$$

The contact matrix $C_{ij}$ depends solely on structural information, while $\Delta_{ij}$ uses only the parental sequence alignment. Specifically, $C_{ij}=1$ if residues i and j are within 4.5 Å in the parental structure; otherwise $C_{ij}=0$. The delta function $\Delta_{ij}=0$ if the amino acids $\sigma_i(S_i)$ and $\sigma_j(S_j)$ that are found in the chimera are also present at homologous positions in any single parent. Otherwise, the i-j interaction is considered broken and $\Delta_{ij}=1$.

From these calculations, crossovers were selected that appeared in greater than 40% of the libraries that had a $F_{30}$ of greater than 25%. Thus, selecting crossover points that were common throughout libraries that had greater than at least about 25% of the population folded. This resulted in 14 crossover points. All possible combinations for chimeras of this set of 14 crossover points were then calculated. From these, a library was chosen that had 1) a high fraction folded ($F_{30}=35\%$), 2) a high average effective level of mutation ($<m>_{30}=64$), and 3) crossovers spread throughout the sequence (fragment size ~59±10 residues).

Figure 6:
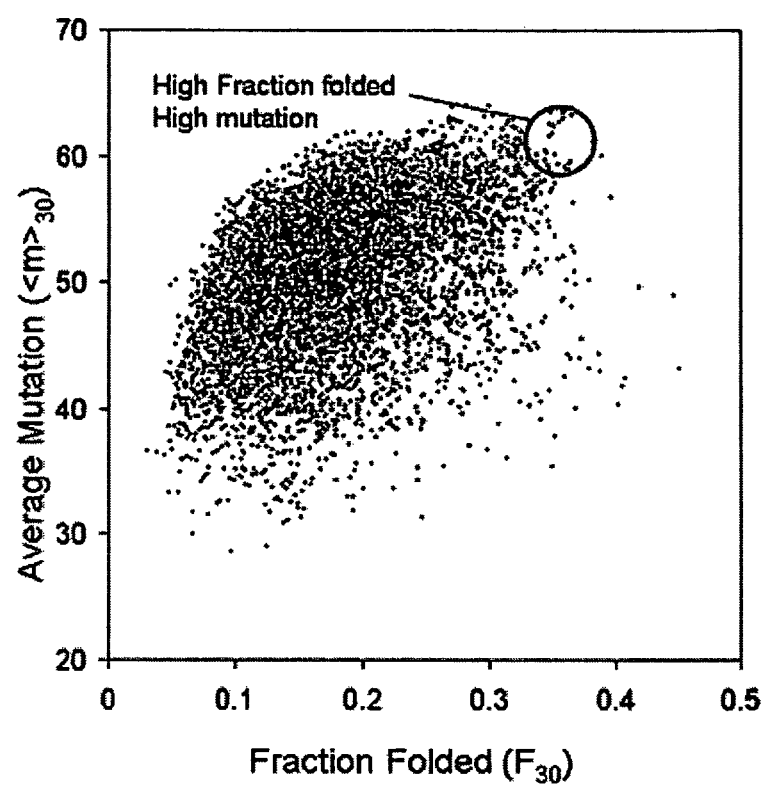
FIG. 6 is a graph displaying various theoretical libraries.
Figure 7:
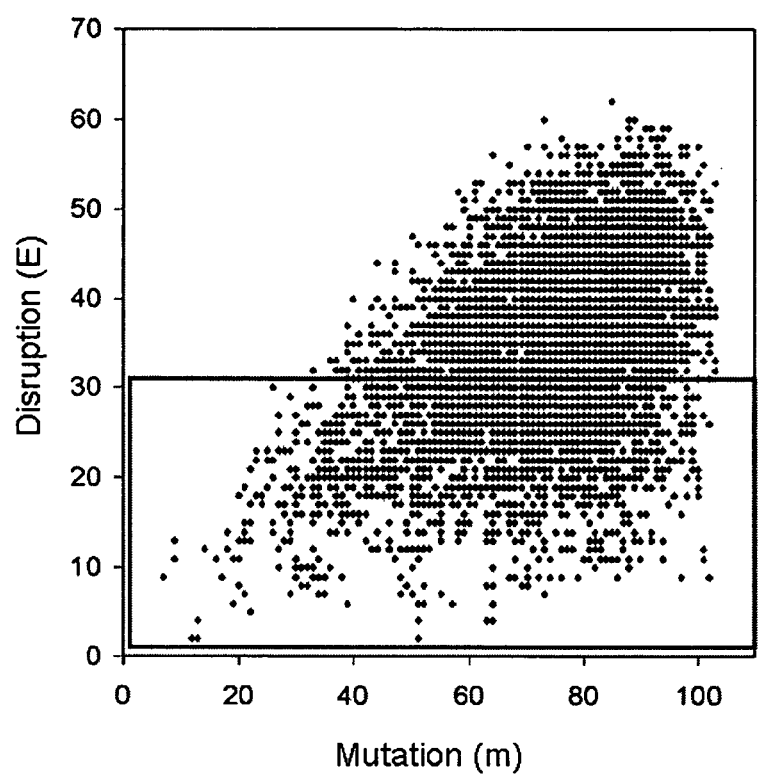
FIG. 7 is a graph displaying various theoretical libraries and a box showing those libraries with an average E value below 32.6±9.8

The final crossover locations lie directly after the following residues Glu64, Ile122, Tyr166, Val216, Thr268, Ala328, Gln404. This resulted in an eight fragment library that consists of 6561 possible members. The $F_{30}$ and $<m>_{30}$ values relative for the 5000 randomly generated libraries can be seen in FIG. 6. FIG. 6 also displays a selection of libraries that contain an average mutation number that is high and a high percentage of folded proteins (over 30%). The average disruption (or number of bonds broken) for the entire library was calculated as $<E>=32.6\pm9.8$ and the average number of mutations was $<m>=72.6\pm16.6$. Among those chimeras predicted, at least 35% will be folded and have mutation levels up to approximately 100 amino acid differences relative to the closest parent (see FIG. 7).

As appreciated by one of skill in the art, a high percentage of folded proteins can vary depending upon the situation. In one embodiment, anything higher than 9% is high. In another embodiment, a high percentage will be anything greater than the average percentage of folded proteins from random recombination, for example 42% in the simple A1 and A2 recombination chimeras. High may also include 5-10, 10-20, 20-30, 30-40, 40-50, 50-70, 70-90, 90-99, or 99-100 percent folded.

Example 9

This example demonstrates how a protein library, designed in Example 8, was constructed. The construction of the library followed methods reported previously (Hiraga and Arnold (Hiraga, K., and Arnold, F. H., J. Mol. Biol., 330:287-296 (2003)). However, instead of BaeI, BsaXI was used as the type IIb restriction endonuclease since it results in more complete DNA digestion. In short, Tag sequences were inserted at each crossover site. Upon digestion with BsaXI, each crossover has a unique nucleotide overhang sequence. These were serially ligated into a complete gene and ligated into the pCWori plasmid.

Figure 8:
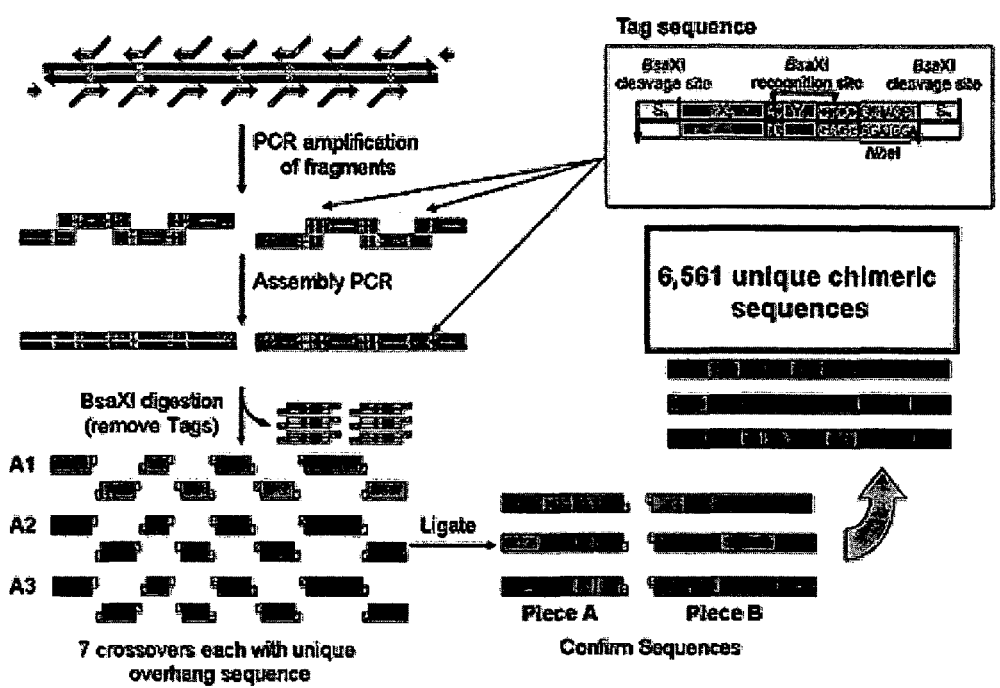
FIG. 8 is an illustration displaying the construction of a seven crossover library.

The library was transformed into a catalase free strain of *E. coli* that allowed for peroxygenase activity of the chimeric heme domains to be measured using cell lysates. The process can be seen in FIG. 8. The resulting chimeras were then examined in Examples 9-11.

In short, N-terminal (SCHEMA fragments 1-4) and C-terminal (SCHEMA fragments 5-8) shuffled libraries were constructed separately, and cloned together into an expression vector. Prior to the construction of parental plasmid, this BsaXI site was removed by synonymous mutation at Gly368 by site directed mutagenesis (GGA to GGT).

First, a series of tag sequences containing a type IIb endonuclease recognition sequence (BsaXI) were inserted into the three boundaries of each half-length parental gene (64, 122, and 166 for N-terminal gene, 268, 328, and 404 for C-terminal gene, according to the numbering of A1H), using the primers shown in Table 2. Targeted SCHEMA fragments were amplified using synthetic oligonucleotides that contained a tag sequence (Table 2), and these PCR fragments were then combinatorially assembled into half-length genes with tag insertions by a self-priming overlap polymerase reaction. The parental half-length genes were cloned into the cloning site of a TOPO plasmid (Invitrogen) and their DNA sequences were confirmed. All of the parental genes were inversely inserted into the plasmid to inhibit expression of the foreign protein.

TABLE 2

| Tag | Site | Tag Sequence (5' to 3') | | Primer (5' to 3') |
|---|---|---|---|---|
| N | N-term | - | A123-Nf | GGAGGTACCAGATCTATCGATGCTTAGGAGGTCATATG (SEQ ID NO: 22) |
| Tag 1 | 64 | gaaTGAAGTACTACCTGT CCTCCGCTAGCTgaa (SEQ ID NO: 21) | A1-64f | GTACTACCTGTCCTCCGCTAGCTgaaTCACGCTTTGATAAAAACTTAAGT (SEQ ID NO: 23) |
| | | | A1-64r | AGCGGAGGACAGGTAGTACTTCAttcATCGCATGCTTCTTTAATTAGAC (SEQ ID NO: 24) |
| | | | A2-64f | GTACTACCTGTCCTCCGCTAGCTgaaGAACGGTTTGATAAAAGCATTG (SEQ ID NO: 25) |
| | | | A2-64r | AGCGGAGGACAGGTAGTACTTCAttcATCACAAACCTCTTTCACCA (SEQ ID NO: 26) |
| | | | A3-64f | GTACTACCTGTCCTCCGCTAGCTgaaAAACGCTTTGACAAGAACCT (SEQ ID NO: 27) |
| | | | A3-64r | AGCGGAGGACAGGTAGTACTTCAttcATCACACACTTCAGCCAC (SEQ ID NO: 28) |
| Tag 2 | 122 | atcTAAAGGCCTACATAC TCTCCGCTAGCAatc (SEQ ID NO: 29) | A1-122f | GGCCTACATACTCTCCGCTAGCAatcGCCGTGCAGCTTGTTC (SEQ ID NO: 30) |
| | | | A1-122r | AGCGGAGAGTATGTAGGCCTTTAgatATCGACCATCATCGCATGAT (SEQ ID NO: 31) |
| | | | A2-122f | GGCCTACATACTCTCCGCTAGCAatcGCTGTTCAGCTCATTCAAAAATG (SEQ ID NO: 32) |
| | | | A2-122r | AGCGGAGAGTATGTAGGCCTTTAgatATCGACCATTTTCTCATGATAGTC (SEQ ID NO: 33) |
| | | | A3-122f | GGCCTACATACTCTCCGCTAGCAatcGCAACCCAGCTGATTC (SEQ ID NO: 34) |
| | | | A3-122r | AGCGGAGAGTATGTAGGCCTTTAgatATCCAGCATCATAGAATGATAGC (SEQ ID NO: 35) |
| Tag 3 | 166 | tacTGATCGCGAACAATT ACTCCGCTAGCTtac (SEQ ID NO: 36) | A1-166f | CGCGAACAATTACTCCGCTAGCTtacCGAGATCAGCCTCATCC (SEQ ID NO: 37) |
| | | | A1-166r | AGCGGAGTAATTGTTCGCGATCAgtaAAAGCTGTTAAAGCGATAGTTAAA (SEQ ID NO: 38) |
| | | | A2-166f | CGCGAACAATTACTCCGCTAGCTtacAGAGAAACGCCCCACC (SEQ ID NO: 39) |
| | | | A2-166r | AGCGGAGTAATTGTTCGCGATCAgtaGTAACTGTTAAAGCGGTAGTTAAA (SEQ ID NO: 40) |
| | | | A3-166f | CGCGAACAATTACTCCGCTAGCTtacCGTGATTCACAGCATCC (SEQ ID NO: 41) |
| | | | A3-166r | AGCGGAGTAATTGTTCGCGATCAgtaAAAGCTGTTGAATCGATAGTTAAA (SEQ ID NO: 42) |
| | 216/217 | - | A1-216f | CGAGGTACCgtcgacAAAATTATTGCAGATCGCAAAGC (SEQ ID NO: 43) |
| | | | A1-216r | CCGCTCGAGgtcgacTAGGTCGTTCATCACCTTG (SEQ ID NO: 44) |
| | | | A2-216f | CGAGGTACCgtcgacAGCATTATTGCAGAG (SEQ ID NO: 45) |
| | | | A2-216r | CCGCTCGAGgtcgacTAACGAAAACATCGTTTG (SEQ ID NO: 46) |
| | | | A3-216f | CGAGGTACCgtcgacAGAATGATAGCGGAGCGAAAG (SEQ ID NO: 47) |
| | | | A3-216r | CCGCTCGAGgtcgacCAGGGAGTTCATGACTTC (SEQ ID NO: 48) |

| Tag 4 | 268 | acaTGAACGCGTACTTAT TCTCC<u>GCTAGC</u>Taca (SEQ ID NO: 49) | A1-268f | CGCGTACTTATTCTCCGCTAGCT*aca*A*CAAGTG GTCTTTTATCATTTGC* (SEQ ID NO: 50) |
|---|---|---|---|---|
| | | | A1-268r | AGCGGAGAATAAGTACGCGTTCA*tgt*T*TCGTGT CCCGCAATTAAG* (SEQ ID NO: 51) |
| | | | A2-268f | CGCGTACTTATTCTCCGCTAGCT*aca*A*CGAGCG GCCTGCTTT* (SEQ ID NO: 52) |
| | | | A2-268r | AGCGGAGAATAAGTACGCGTTCA*tgt*T*TCATGG CCGGCAATC* (SEQ ID NO: 53) |
| | | | A3-268f | CGCGTACTTATTCTCCGCTAGCT*aca*A*CAAGCG GGTTGCTATC* (SEQ ID NO: 54) |
| | | | A3-268r | AGCGGAGAATAAGTACGCGTTCA*tgt*C*TCATGT CCAGCAATTAAAAATG* (SEQ ID NO: 55) |
| Tag 5 | 328 | gctTAAGTATACACCATC CCTCC<u>GCTAGC</u>Agct (SEQ ID NO: 56) | A1-328f | TATACACCATCCCTCCGCTAGCA*gct*C*CTGCGTT TTCCCTATATG* (SEQ ID NO: 57) |
| | | | A1-328r | AGCGGAGGGATGGTGTATACTTA*agc*A*GTTGGC CATAAGCGC* (SEQ ID NO: 58) |
| | | | A2-328f | TATACACCATCCCTCCGCTAGCA*gct*C*CGGCTTT CAGCCTTTATC* (SEQ ID NO: 59) |
| | | | A2-328r | AGCGGAGGGATGGTGTATACTTA*agc*T*GTCGGC CATAAGCGC* (SEQ ID NO: 60) |
| | | | A3-328f | TATACACCATCCCTCCGCTAGCA*gct*C*CGGCTTT TTCTCTATATGC* (SEQ ID NO: 61) |
| | | | A3-328r | AGCGGAGGGATGGTGTATACTTA*agc*T*GTTGGA TACAGTCTGAGG* (SEQ ID NO: 62) |
| Tag 6 | 404 | cagTGATTCGAAACCATT ACTCC<u>GCTAGC</u>Tcag (SEQ ID NO: 63) | A1-404f | TCGAAACCATTACTCCGCTAGCT*cag*T*TCGCTCT TCATGAAGC* (SEQ ID NO: 64) |
| | | | A1-404r | AGCGGAGTAATGGTTTCGAATCA*ctg*C*TGACCG ATACACGCAC* (SEQ ID NO: 65) |
| | | | A2-404f | TCGAAACCATTACTCCGCTAGCT*cag*T*TTGCCCT TCATGAAGC* (SEQ ID NO: 66) |
| | | | A2-404r | AGCGGAGTAATGGTTTCGAATCA*ctg*C*ATGCCG ATACAGGCC* (SEQ ID NO: 67) |
| | | | A3-404f | TCGAAACCATTACTCCGCTAGCT*cag*T*TTGCTCT TCAAGAAGCG* (SEQ ID NO: 68) |
| | | | A3-404r | AGCGGAGTAATGGTTTCGAATCA*ctg*C*ATGCCA ATACAAGCGC* (SEQ ID NO: 69) |
| C | C-term | — | A1-Cr | CAACAATTG*TTAAGTGCTAGGTGAAGGAATACC* (SEQ ID NO: 70) |
| | | | A2-Cr | CAACAATTG*TTATTCAGCTGCCTGGACGTC* (SEQ ID NO: 71) |
| | | | A3-Cr | CAACAATTG*TTATGCCTGTTCTTTTCTCTGTAC* (SEQ ID NO: 72) |

Bold letters: BsaXI recognition site; underline: NheI recognition site; Lower-case letters: consensus sequence (sticky ends by BsaXI digestion); Italic letters: complemental sequence to a parent for SCHEMA gene fragment amplification; Shadowed letters: BglII or MfeI recognition site of N-terminal or C-terminal primer, respectively.

The P450s A1H, A2H, and A3H share the same amino acids at each of the targeted crossover site. Because the tag sequences were designed to encode these consensus codons at the BsaXI cleavage sites, unique 3 bp overhangs were created on the both ends of each targeted fragment upon BsaXI digestion. After removing small tags (30 bp) by column purification, the DNA fragments from three parents were mixed and ligated with each other using the 3 bp overhangs of the consensus sequences, resulting in the half-length chimeric library without tag sequences between targeted SCHEMA fragments. A NheI site designed in the inserted tag sequence along with BsaXI were used after ligation to remove residual parental genes from a final library. After the PCR amplification of the half-length library, PCR products were cloned back into the TOPO vector and transformed into TOP10. The size of the half-length library was greater than 10,000, well exceeding the possible number of combinations, 81.

The N- and C-terminal libraries were then digested with BglII/SalI, and SalI/MfeI, respectively, and cloned into BamHI/EcoRI site of an expression vector, pCWori (Barnes et al., Proc. Natl. Acad. Sci. USA, 88:5597-5601 (1991)). The SalI recognition site corresponds to the targeted crossover site 216-217 and was introduced into all three P450 genes synonymously. This site was used to ligate the N- and C-terminal libraries together, yielding the full-length chimeric library.

The library plasmid DNA was transformed into a catalase free E. coli strain SN0037 (Nakagawa, et al., Biosci. Biotechnol. Biochem. 60, 415-420 (1996)) followed by culturing LB media containing ampicillin.

Detailed Construction Information
BsaXI Site Removal from A1H Gene

The wild type A1H sequence has a BsaXI recognition site in the middle of fragment 7. Prior to the construction of parental plasmid, this BsaXI site was removed by synonymous mutation at Gly368 by site directed mutagenesis (GGA to GGT). The N- and C -terminal gene fragments were amplified by PCR using pWCori-A1H as a template, and the primers set A123-Nf and A1-A1107Tr (5'-CCACATCGTC ACCCCAAATTGTTTTATCACGGTG-3', SEQ ID NO: 73) for N-terminal fragment, and A1-A1107Tf (5'-CAATTTGGGGTGACGATGTGGAAGAGTTCCG-3', SEQ ID NO: 74) and A1-Cr for C-terminal fragment. The underlined nucleotides correspond to the mutation site and the italics are complementary each other. These fragments were assembled by a second PCR. The PCR product was subcloned pCR-Blunt II-TOPO vector (Invitrogen) and transformed into TOP10. The parental plasmids were purified by QIAquick plasmid mini-prep kit (QIAGEN) and all tag-insertions were certified by DNA sequencing.

Insertion of Tag-Sequence into Targeted Sites of Parent Genes

Half length parental plasmids in which a variety of BsaXI recognition sequences were inserted into the targeted positions of each half-length P450 genes were created by stepwise assembly PCR, as described previously (Hiraga and Arnold, 2003). First, gene fragments that encode for fragments of P450s (A1H, A2H and A3H) were amplified by PCR from plasmids pCWori-A1H, pCWori-A2H, and pCWori-A3H, respectively, using a set of flanking primers listed in Table 2. A 50 µl reaction mixture contained: 1× vent DNA polymerase buffer, 0.2 mM each of dNTP, 10 pmol of each primer, 2 U of vent DNA polymerase, and 10 ng of template plasmid. Reaction mixtures was heated at 95° C. for 5 minutes, followed by 25 cycles of incubation at 95° C. for 1 minutes, 52° C. for 30 seconds, 72° C. for 30 seconds, and final incubation at 72° C. for 10 minutes.

The products were verified on and purified from Seakem GTG agarose gels (BioWhittaker Molecular Applications) by Zymoclean Gel DNA recovery Kit (Zymo Research), and resolved in 20 µl of 10 mM Tris-HCl (pH 8.5). Next, SCHEMA fragments 1-4 and 5-8 were assembled by PCR, respectively (1234 and 5678), using complementary sequences designed in tags (Table 2). Assembly reaction of DNA fragments was carried out in 1× vent DNA polymerase buffer, 0.2 mM each of dNTP, 5 µl each of DNA fragments, 20 pmol of each primer, and 4 U of vent DNA polymerase in a total volume of 100 µl. Reaction mixtures were heated at 95° C. for 5 minutes, followed by 25 cycles of incubation at 95° C. for 1 minutes, 52° C. for 30 seconds, 72° C. 30 seconds, and final incubation at 72° C. for 20 minutes. The half-length gene fragments were purified by agarose gel extraction, and were cloned into pCR-Blunt II-TOPO vector (Invitrogen) and transformed into TOP10. The parental plasmids were purified by QIAquick plasmid mini-prep kit (QIAGEN) and all tag-insertions were certified by DNA sequencing.

Construction of Half-Length Library

The half-length gene fragments with tag insertion were amplified again by PCR from the parental plasmids described above, using M13 forward and M13 reverse primers. DNA concentration of the fragment was determined spectrophotometrically, and 2 µg of each fragment was subjected to BsaXI digestion. After purification by DNA clean and concentrator kit (Zymo Research), the digested fragments from A1-1234, A2-1234 and A3-1234, or A1-5678, A2-1234 and A3-5678, were mixed and ligated by T4 DNA ligation kit (Roche) in 10 µl reaction mix. After removal of untreated DNA fragments with Nhe I and BsaXI, the recombined half-gene libraries were amplified by PCR using M13 forward and M13 reverse. The PCR products were purified by gel extraction and cloned back into pCR -Blunt II TOPO vector and transformed into TOP10. The number of independent clones in a half-length library was estimated by counting the number of colonies. Half-length library plasmids were purified by QIA quick plasmid mini-prep-kit (QIAGEN).

Construction of Full-Length Library

The half-length libraries were digested from TOPO vector with BglII/SalI (for the library 1-4) or SalI/MfeI (for the library 5-8). After gel purification and quantification, equal amount of the half-gene library fragments were mixed and cloned both together into BamHI/EcoRI sites of the expression plasmid pCWori by ligation. Competent E. coli SN0037 (Nakagawa, et al., Biosci. Biotechnol. Biochem. 60, 415-420 (1996)) cells were transformed with the ligation mixture and grown overnight at 37° C. on LB agar plates containing 100 µg/ml ampicillin.

Example 9

This example demonstrates one method by which the quality of the library produced can be examined. DNA probe hybridization was performed in order to evaluate the relative amount of each parent at each position within the library (Joern, et al., J Mol Biol, 316:643-656 (2002) and Meinhold, P. et al., Methods Mol Biol, 231:177-187(2003)).

Clones from the unselected (naive) library were analyzed by probe hybridization in a macroarray format as previously described (Joern, J. M., Meinhold, P., and Arnold, F. H. J. Mol. Biol., 316:643-656 (2002)). A 384-well plate was filled with 70 µl of LB medium containing 100 µg/ml ampicillin. Independent colonies from a naive library were picked randomly and inoculated into the filled wells along with two of each parents as controls. Following overnight incubation at 30° C. 200 rpm, the plate was replicated onto 16 pieces of Hybond-N+ 7.5 cm×11.5 cm (Amersham Pharmacia) placed on LB medium plates containing 100 µg/l ampicillin, using a 384 pin replicator. After overnight growth, cells were lysed and DNA was denatured and bound to the membrane by UV-crosslinking according to the manufacturer's protocol (Amersham Pharmacia) and previous methods (Meinhold, et al., *Methods Mol. Biol.* 231:177-187 (2003)). Oligonucleotide probes were designed to specifically bind to each of the three parents within each of the 8 fragments approximately the same $T_m$ (Table 3). The 24 probes for the libraries were obtained from QIAGEN Operon. They were labeled with fluorescein-11-dUTP using the terminal transferase reaction according to the Gene Images 3'-oligolabeling module protocol (Amersham Pharmacia). Labeled probes were hybridized to chimeric clones included in the naive library according to the Gene Images protocol. Approximately 90 ng of labeled probe was added to pre-hybridized membranes in 18 ml of hybridization buffer and incubated for two hours at 58° C. Stringency washes were carried out once in 1×SSC (0.015 mM sodium citrate, 0.15 mM NaCl, 0.1% SDS, pH 7) for 15 minutes at 53° C. The Gene Images CDP-Star detection module (Amersham) was used according to manufacturer's instruction to obtain a chemiluminescent signal.

TABLE 3

| Probe set | Parent | Sequence (5' to 3') |
|---|---|---|
| S1 | A1H (SEQ ID NO: 79) | GAC AAT TAA AGA AAT GCC TCA GCC AAA AAC GTT TGG |
|  | A2H (SEQ ID NO: 80) | GAA GGA AAC AAG CCC GAT TCC TCA GCC |
|  | A3H (SEQ ID NO: 81) | GAA ACA GGC AAG CGC AAT ACC TCA GCC |
| S2 | A1H (SEQ ID NO: 82) | GCG CAT AAT ATC TTA CTT CCA AGC TTC AGT CAG C |
|  | A2H (SEQ ID NO: 83) | GCG CAC AAC ATT CTG ATG CCG ACG TTC |
|  | A3H (SEQ ID NO: 84) | CC CAC CGC ATT TTG CTG CCG AGT TTT AG |
| S3 | A1H (SEQ ID NO: 85) | GAG CGT CTA AAT GGA GAT GAG CAT ATT GAA GTA CCG |
|  | A2H (SEQ ID NO: 86) | GCA AGG CTC AAC CCG AAT GAA GCA GTC |
|  | A3H (SEQ ID NO: 87) | G AGC CGG TTA AAC CCC AAT GAA GAA ATT GAT GTA G |
| S4 | A1H (SEQ ID NO: 88) | CCA GAC GAC CCA GCT TAT GAT GAA AAC AAG C |
| S4 | A2H (SEQ ID NO: 89) | GTT CAA GAT AAG CTT ATG GTC AGA ACA AAG CGG C |
|  | A3H (SEQ ID NO: 90) | CTG CAA GAT AAA ATG ATG GTG AAA ACG AAG CTG CAG |
| S5 | A1H (SEQ ID NO: 91) | GCA AGC GGT GAA CAA AGC GAT GAT TTA TTA ACG C |
|  | A2H (SEQ ID NO: 92) | GCG AAT GGA GAC CAG GAT GAA AAA GAT TTG CTC |
|  | A3H (SEQ ID NO: 93) | GCG AAT CCG GAT GAA AAC ATT AAG GAT CTC TTG TC |
| S6 | A1H (SEQ ID NO: 94) | GCA GCA CGA GTT CTA GTA GAT CCT GTT CC |
|  | A2H (SEQ ID NO: 95) | GTC GAT CGG GTG CTG ACG GAT GCA G |
|  | A3H (SEQ ID NO: 96) | GCG GAT CGC GTG TTA ACG GAT GAC AC |
| S7 | A1H (SEQ ID NO: 97) | CCA AGT GCG ATT CCG CAG CAT GCG |
|  | A2H (SEQ ID NO: 98) | CAG GAC CAA GTG CCT CAT CAT GCG TAC |
|  | A3H (SEQ ID NO: 99) | CCT TCA AGT ATC CCT CAC CAT GCG TAT AAG C |
| S8 | A1H (SEQ ID NO: 100) | ATC GAA AAA AAT TCC GCT TGG CGG TAT TCC TTC AC |
|  | A2H (SEQ ID NO: 101) | GCC GTC ATC AGG AAG CCA TTC ATG CAG A |
|  | A3H (SEQ ID NO: 102) | CGC GAA AAA CAG CGG CAA TCA ATG TAC AGA G |

Figure 9:
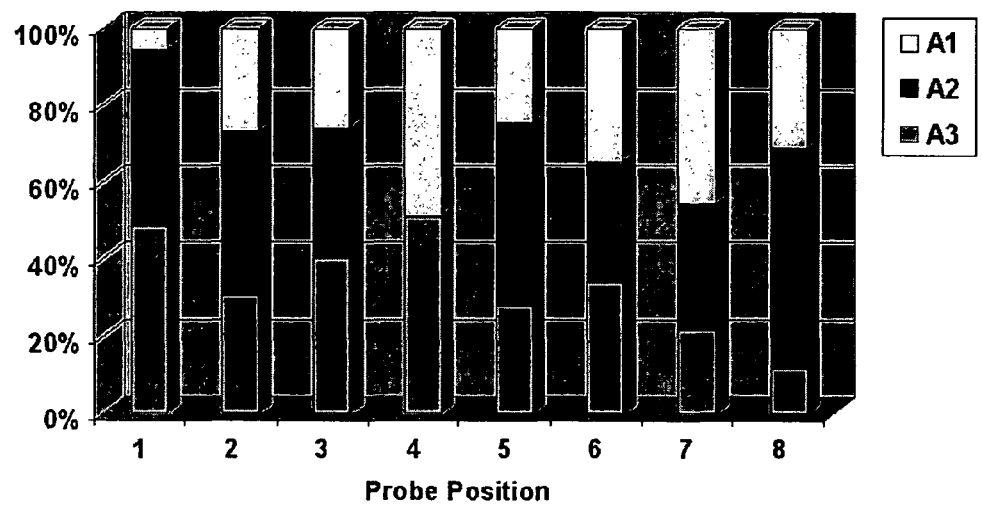
FIG. 9 is a bar chart displaying the relative amounts of A1, A2, and A3 in the chimeras of the library.

A DNA probe that binds uniquely to each position of the library for each parent was designed resulting in 24 probes. DNA probe hybridization was performed to assess library biases. The results can be seen in FIG. 9. There were two main biases in the library. One against parent A1 at position 1 and another against parent A3 at position 8. Only one chimera had A2 at position 4. The proportion of each parent at the other positions was acceptable.

Example 10

This example demonstrates a similar method as described above for identifying chimera folding, and reveals how that E values for folded proteins can be used to determine the percent of folded proteins in a more complex library. To approximate the percent of the library that is folded, 752 randomly picked chimeras were screened using high-throughput carbon monoxide (CO) binding (Otey, C. R. High-throughput carbon monoxide binding assay for cytochromes P450. Directed Enzyme Evolution: Screening and Selection Methods. F. H. Arnold and G. Georgiou. Totowa, N.J., Humana Press: 137-139 (2003)). It was found that 36% of 752 clones assayed were folded (displayed a Soret band at 450 or 420 nm). It was found that 40 out of 50 (80%) randomly picked colonies contained an insert of the correct size as determined by digestion with BsaXI. This yielded two bands of 3.0 and 3.1 kb using DNA gel electophoresis. The presence of no insert, unremoved tag or contaminant was accounted for by this. This resulted in approximately 45% of the library with correctly sized chimeric gene inserts forming a folded protein. 89% were P450s with the remaining 11% being P420s which results in 38.6% of the library yielding a folded P450.

Additionally, chimeras were sequenced that were both folded and unfolded using DNA probe hybridization. Of 384 chimeras, 207 full length sequences were obtained. It was found that those chimeras that folded into a P450 structure (e.g., displayed a Soret peak at 450 nm) have a lower average disruption ($<E>_{P450}$=24.7) and mutation ($<m>_{P450}$=58) than those that are unfolded ($<E>_{Unfolded}$=34.6 and $<m>_{Unfolded}$=66). The average of the entire library is $<E>$=32.6 and $<m>$=72.6. Thus, even for more complex libraries of P450s, involving more than two crossovers and three parents, the E value still appears to be an accurate indicator of protein folding. This allows one to customize E values to particular chimeric conditions. This also demonstrates that while a low E value is useful in creating an optimized library, adjusting the E value in light of the above experimental data can again result in a more accurate indicator of folding and function as an E value of 24.7 will allow for the selection of about half of the properly folded chimeras.

Figure 10:
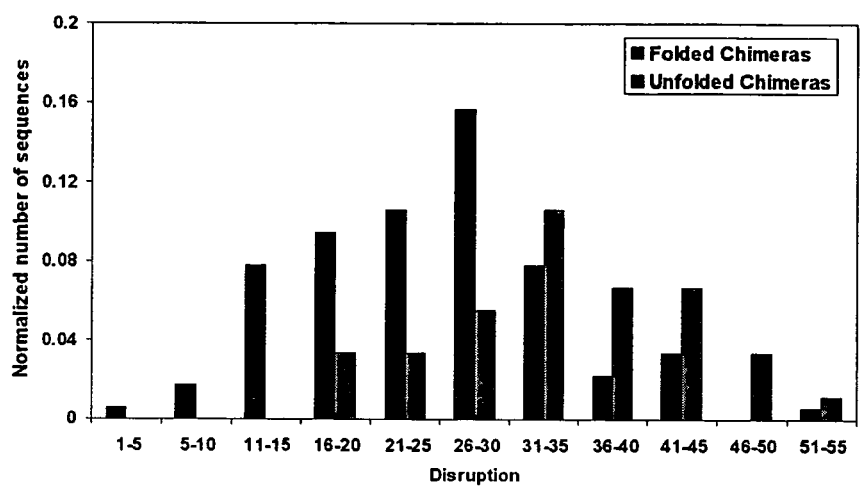
FIG. 10 is a bar graph showing the Enrichment of folded P450s at low E.

The enrichment of folded P450s vs. unfolded proteins at lower values of E can be seen in FIG. 10. Enrichment of folded P450s at low E. The distribution of 207 folded and unfolded chimeric p450s. Normalized number of sequences represents the number of folded or unfolded chimera within each disruption bin divided by the total of the unfolded and folded sequences Importantly, no chimera with an E of less than 15 was unfolded and only one chimera with an E greater than 45 was folded.

Example 11

This example demonstrates one way that the more complex chimeras from Example 10 and libraries of these chimeras may be examined. Chimeras from Example 10 that displayed a Soret band at 450 nm (see above) were condensed onto plates to remove unfolded variants along with the addition of parental sequences for controls. This resulted in a plate consisting of 4 wells of each parent, 4 wells of a null vector control and 80 chimeras that fold into P450s (hereinafter "library plate"). These library plates were replicated and grown in 96 deep-well plates in 900 μL of LB media with 100 μg/ml ampicillin overnight at 30° C. and 250 rpm. 150 μL of this was then transferred to 850 μL of induction media (TB-media with final concentrations of 100 μg/ml ampicillin, 25 μg/ml thiamine, 0.5 mM δ-aminolevulinic acid and 0.6 mM IPTG). These were grown for 20-24 hours at 25° C. and 190 rpm, harvested by centrifugation at 5000×g for 8 minutes and frozen at −20° C. for at least 24 hours. Cells were resuspended using a pipetting robot (Multimek 96, Beckman) and lysed in 400 μL of Epps or Tris buffer (100 mM, pH 8.2) containing 0.8 mg/ml lysozyme and 2 units/mL DNaseI for 1 hour at 37° C. Plates were then spun for 8 minutes at 5000×g and 4° C. to pellet cell debris. 80 μL of lysate was transferred into 4 separate 96 well plates for each library plate. This resulted in 4 screening plates per growth plate. On one plate, high-throughput carbon monoxide spectroscopy was done in order to assess relative amounts of P450 (Otey, C. R. High-throughput carbon monoxide binding assay for cytochromes P450. In Directed Enzyme Evolution: Screening and Selection Methods, F. H. Arnold and G. Georgiou, eds. (Totowa, N.J.: Humana Press) pp. 137-139 (2003)) with 0.1 M sodium hydrosulfite being used in place of 0.4 M. The other three plates were used to assay activity on different substrates. Examples of assays that have been or could be used include the 4-AAP (Otey, C. R., and Joern, J. M. High-throughput screen for aromatic hydroxylation. In Directed Enzyme Evolution: Screening and Selection Methods, F. H. Arnold and G. Georgiou, eds. (Totowa, N.J.: Humana Press), pp. 141-148 (2003)), 12-pNCA (Schwaneberg et al., *Anal. Biochem.,* 269: 359-366 (1999), NBP assay (Alcalde, et al., J Biomol Screen, 9:141-146 (2004)), 7-ethoxyresorufin (Sieber et al., *Nat Biotechnol.,* 19:456-460 (2001)), vivid substrate assays (Marks et al., Assay Drug Dev Technol 1, 73-81 (2002); Marks et al., AAPS PharmSci 5, E18 (2003)), and purpald assays (Peters et al., J Am Chem Soc 125:13442-13450 (2003)). Since the heme domains were being used, the hydrogen peroxide was used to drive the reactions via the peroxide shunt (Cirino, P. C., and Arnold, F. H., *Advanced Synthesis & Catalysis* 344, 932-937 (2002)).

The 4-AAP assay detects phenol-like compounds and consists of the addition of 40 μL of a 3.5× substrate solution (containing substrate concentrations dependent for each substrate) to 80 μL of lysate. For instance, the concentration used for 2-phenoxyethanol was 100 mM and the concentrations used for ethoxy-benzene, diphenyl ether and allyloxy-benzene were 50 mM. This resulted in the maximum substrate concentration while retaining a clear solution to accurately read the $A_{500}$, 3.5% (v/v) of both acetone and DMSO and 100 mM Epps or Tris buffer pH 8.2. Then a 7×(140 mM) $H_2O_2$ hydrogen peroxide solution was added resulting in a final concentration of 20 mM hydrogen peroxide. The reaction was mixed and left at room temperature without shaking for two hours and then quenched with 140 μL of 0.1 m NaOH and 4 M Urea. 38 μL of 0.6% 4-aminoantipyrine was added followed by blanking of the 96-well plate reader at 500 nm. 38 μL of 0.6% potassium persulfate was added and after 20 minutes the $A_{500}$ was read. Those with an $A_{500}$ greater than 2.5 standard deviations (based on the CV of the assay: 15%) from the average of the null vector are considered active. The endpoints of these assays reflected total turnovers and are normalized to P450 concentration using $A_{448}$-$A_{490}$ from high-throughput CO difference spectroscopy. It was found that the parents were active on three of five 'test' substrates.

Figure 11:
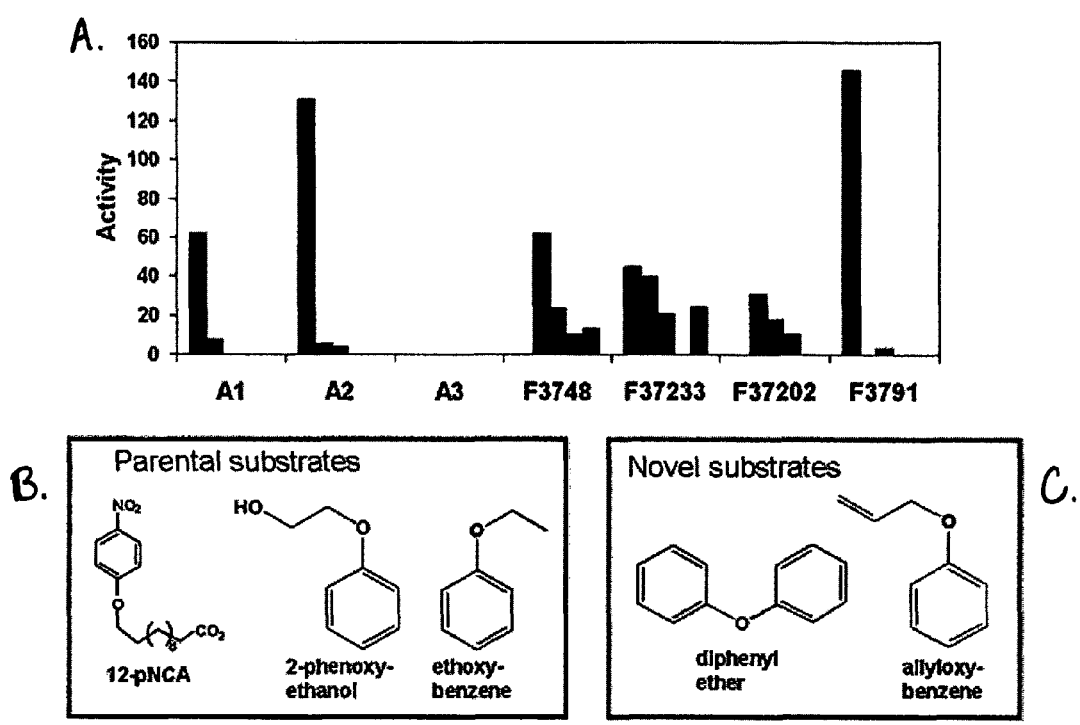
FIG. 11A is a bar graph displaying the relative amounts of activity of the parents and the chimeras
FIG. 11B is an illustration showing three substrates of the parents.
FIG. 11C is an illustration showing two novel substrates of the chimeras.

Activity of the parent and a few example chimeras can be seen in FIG. 11A. FIGS. 11B and 11C display the structure of the parental substrates (12-pNCA, 2-phenoxy-ethanol, and ethoxy-benzene) and the novel substrates (diphenyl ether and allyloxy-benzene) respectively. FIG. 11A demonstrates that three of the four chimeras tested for activity displayed activity on a novel substrate and one displayed activity on two novel substrates. The bars represent the chimeras' activity on 12-pNCA, 2-phenoxy -ethanol, ethoxybenzene, diphenyl ether, and allyloxy-benzene respectively. As can be observed, chimera F3791 displayed superior activity for 12-pNCA compared to any of the parent P450s. Additionally, F3748 (SEQ ID NO: 75), F37233 (SEQ ID NO: 76), and F37202 (SEQ ID NO: 77) each displayed activity that is novel over the parent chimeras. The sequence for F3791 is shown in SEQ ID NO: 78. Activity on propranolol has also been observed. Interestingly, while A3 displayed no activity towards any of the substrates tested, many of the chimeras still folded and displayed activity (see FIG. 11A).

Table 4 shows that chimeras with novel activity (on allyloxy-benzene and/or diphenyl ether) had a higher average mutation and disruption level than the folded chimeras that have been sequenced. They also had slightly lower disruption than the unfolded chimeras. This demonstrates that higher disruption and/or higher mutation levels is important in the acquisition of novel activities relative to the parental enzymes. It further demonstrates that low E values and high m values may be used to create, choose, or sort through libraries to find or create proteins with a high likelihood of functionality and novel activities.

TABLE 4

| Chimera type | Average mutation ($<m>$) | Average disruption ($<E>$) |
| --- | --- | --- |
| Novel activity | 73.2 ± 13.5 | 31.9 ± 9.0 |
| Parent-like activity | 64.4 ± 18.9 | 24.9 ± 9.2 |
| No activity | 63.0 ± 20.3 | 27.3 ± 10.7 |
| Folded (Naïve) | 57.7 ± 21.4 | 24.7 ± 9.3 |
| Unfolded (Naïve) | 66.3 ± 19.7 | 34.6 ± 8.6 |

Figure 12A:
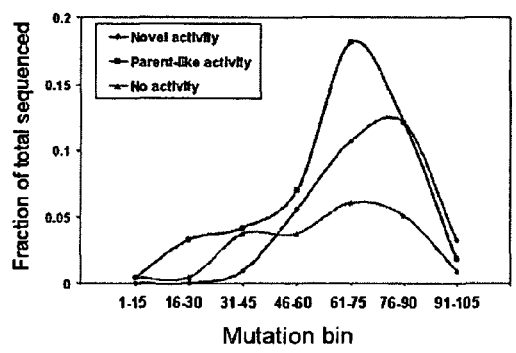
FIG. 12A is a graph displaying the distribution of functional properties for sequenced chimeric cytochromes P450, in particular with regard to the mutation number.
Figure 12B:
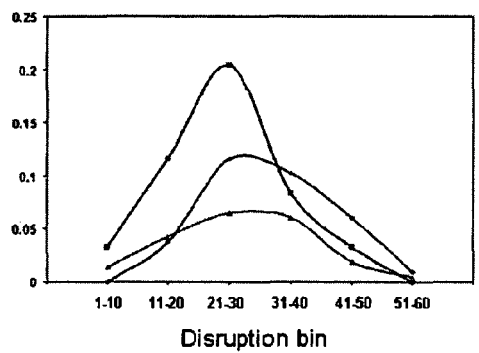
FIG. 12B is a graph displaying the distribution of functional properties for sequenced chimeric cytochromes P450, in particular with regard to the disruption number.

Additionally, FIGS. 12A and 12B show the distribution of functional properties for sequenced chimeric cytochromes P450. Diamonds represent novel activity, squares represent parent-like activity, and triangles represent no activity. Chimeras were placed into mutation or disruption bins and then normalized to the total number of chimeras sequenced. Those with novel activity had a higher average disruption and mutation than those with any parent-like activities. They also had a higher average mutation level than the unfolded chimeras but lower average disruption.

Example 12

Figure 13:
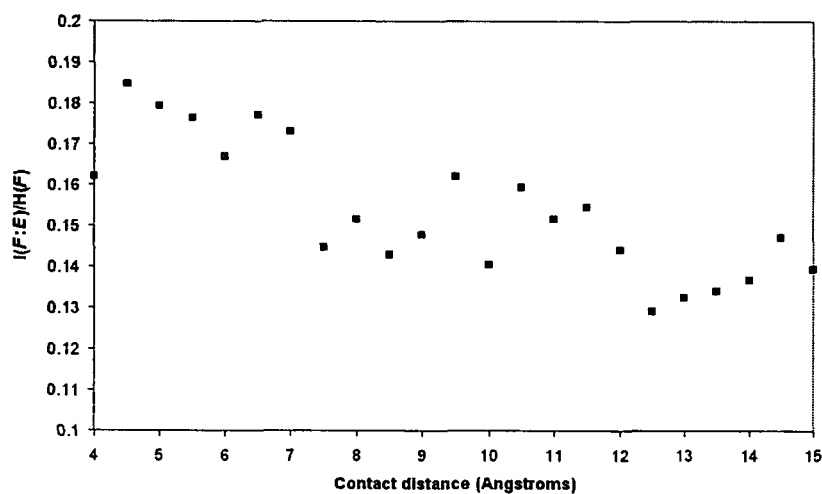
FIG. 13 is a graph displaying the dependence of SCHEMA calculations based on cutoff distances used.

This example demonstrates how one may determine or verify the optimal cutoff value used in the SCHEMA algorithm. Using information theory and the high-throughput folding data for cytochrome P450, the effect of contact distance on SCHEMA disruption was evaluated. The mix of folded and unfolded sequences in the data set was quantified by its entropy H(F). The information between folding and energy I(F:E) measured how much H(F) is reduced by knowing the SCHEMA disruption E of each sequence: I(F:E)=H(F)−H(F|E), where H(F|E) was the conditional entropy. Energy functions with higher information are more effective at protein design. The maximum possible information is the entropy H(F). The information content of SCHEMA disruption had a sensitivity range of 5% (13 to 18% of H(F)) relative to changes in the contact distance from 4 to 15 Angstroms. A contact distance of 4.5 Angstroms was optimal for this data set (see FIG. 13).

In one embodiment, the chimeras are useful for a broader array of substrates, for example, tacrine, naproxen, methoxychlor, diclofenac, zoxazolamine, ethyl 4-phenylbutyrate, and the substrates in Table 5 below. In one embodiment, the substrate may be any substrate that the chimera can assist in catalyzing a reaction to a product. In another embodiment, the chimera may catalyze a reaction with any substrate that any other P450 catalyzes, as demonstrated in the Example below.

Example 13

Some substrates that are hydroxylated by mammalian P450s, many of which are pharmaceuticals, were also analyzed (Lewis, D. F. V., Guide to cytochromes P450: structure and function (London; New York: Taylor & Francis) (2001)). Enzymes that hydroxylate such substrates are interesting since the metabolites that are produced could be useful for toxicity studies (Parikh et al., Nat Biotechnol 15:784-788 (1997), Kim, D., and Guengerich, F. P., Biochemistry 43:981-988 (2004), and Guengerich, F. P., Mol Interv 3, 194-204 (2003)) or could be used to produce hydroxylated variants of existing drugs that have greater efficacy. Table 3 shows some of these substrates along with their associated mammalian P450.

TABLE 5

| Compound (A.K.A) | Mammalian P450[1] | Concentration used (mM)[2] | Function (mechanism) | Structure |
| --- | --- | --- | --- | --- |
| Diclofenac (Voltaren) | CYP2C9 | 10 | Pain killer (nonsteroidal anti-inflammatory) | 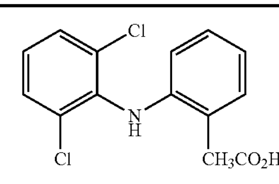 |
| 4-aminobiphenyl | CYP1A2 | 5 | Found in tobacco smoke, carcinogen | 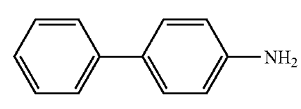 [SMILES: Nc1ccc(-c2ccccc2)cc1] |
| Tolbutamide | CYP2C9 | 20 | Treat type II diabetes (stimulates pancreatic release of insulin) | 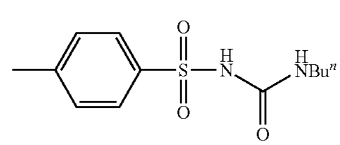 |

TABLE 5-continued

| Compound (A.K.A) | Mammalian P450[1] | Concentration used (mM)[2] | Function (mechanism) | Structure |
|---|---|---|---|---|
| methoxychlor | CYP2B6 | 4 | Pesticide | 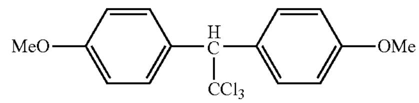 |
| p-acetophenetidide (Phenacetin, Acetphenetidin) | CYP1A2 | 10 | Mild analgesic | 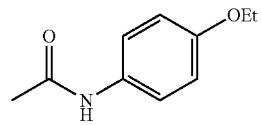 |
| Chlorzoxazone | CYP2E1 | 5 | Treat acute painful muscle conditions (unknown) | 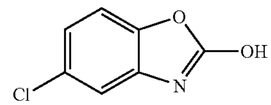 [SMILES: Oc1nc2cc(Cl)ccc2o1] |
| 2-amino-5-chlorobenzoxazole (Zoxazolamine) | CYP1A2 | 4 | Muscle relaxant | 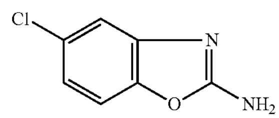 [SMILES: Nc1nc2cc(Cl)ccc2o1] |
| 9-amino-1,2,3,4-tetrahydroacridine hydrochloride hydrate (Tacrine) | CYP1A2 | 10 | Treat alzheimers (acetylcholinesterase inbibitor) | 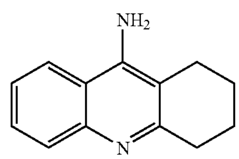 [SMILES: Nc1c2c(nc3ccccc13)CCCC2] |
| Naproxen | CYP2C9 | 10 | Pain killer (nonsteroidal anti-inflammatory) | 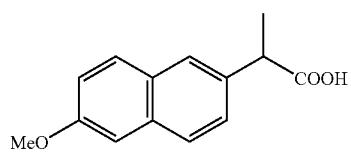 [SMILES: COc1ccc2cc(C(C)C(=O)O)ccc2c1] |
| Propranolol | CYP2D6 | 5 | Beta-Adrenergic Receptor Blocking Agent | 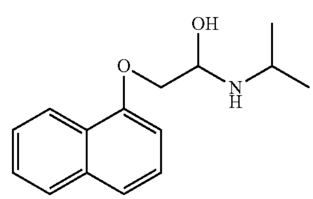 [SMILES: CC(C)NC(O)COc1cccc2ccccc12] |
| Ethyl 4-phenylbutyrate | — | 5 | Derivative of Phenylbutyrate which treats urea cycle disorder | 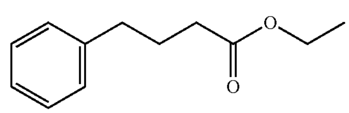 |

[1]Main mammalian P450 responsible for breakdown of each compound.
[2]Concentration of substrate used in 4-aminoantipyrine assay.

By screening condensed libraries on the maximum substrate concentrations allowed by the 4-aminoantipyrine assay (Table 5) chimeras with putatitive activities on the following substrates: 4-aminobiphenyl, chlorzoxazone, and tolbutamide were found.

Figure 14A:
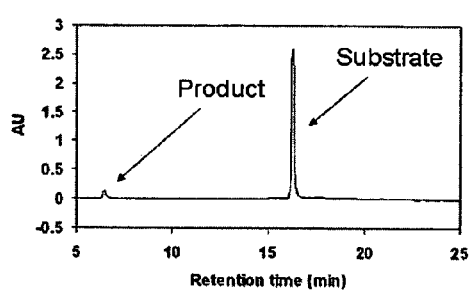
FIG. 14A is a HPLC trace of a bioconversion containing chimera C4H2 and chlorzoxazone.
Figure 14B:
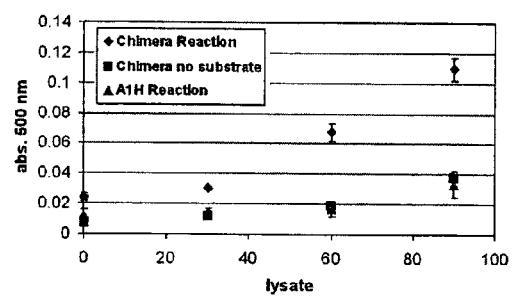
FIG. 14B is a graph displaying the linear increase in product as the amount of enzyme increases as measured by the 4-aminoantipyrine assay at 500 nm. This is the same bioconversion that is occurring in FIG. 14A.

To further verify activity on the above three substrates, bioconversions were done in the presence of increasing concentration of enzyme with the relevant substrate, without the substrate and the most active parent, A1H, with the relevant substrate. Hydroxylated products were monitored with the 4-AAP assay. As expected, the amount of product increases with increasing enzyme with the chimera and substrate present but not with the chimera without substrate or A1H with substrate (FIG. 14B). FIG. 14 shows the results for chlorzoxazone. Diamonds represent a chimera reaction. Squares represent chimera without substrate, and triangles represent a A1H reaction.

Furthermore, a product peak separate from the substrate can be seen in HPLC (FIG. 14A), as measured by the 4-aminoantipyrine assay at 500 nm. This consisted of a distinct product peak at a separate retention time than the substrate not present in the no substrate reaction. The retention times were 18.69 and 20.9 minutes for the products of 4-aminobiphenyl, 6.5 minutes for chlorzoxazone and 7.54, 9.5 and 12.3 minutes for products of tolbutamide. For HPLC, 400 μL bioconversions in 100 mM Epps pH 8.2 containing cell lysate, substrate, 1% DMSO, 1% acetone and 20 mM hydrogen peroxide were allowed to progress for two hours. After acidification with 40 μL 7% perchloric acid and 10 mg of ascorbic acid, centrifugation for 5 minutes at 5000×g, 30-100 ul of the supernatants were analyzed by HPLC. Separation was achieved on a Microsorb-MV phenyl column (250×4.6 mm, Varian, Palo Alto, Calif.). Mobile phase gradients consisted of an aqueous phase containing 1% triethylamine, 0.8% by volume phosphoric acid (pH 2.2) and acetonitrile. The HPLC gradient used for metabolite separation was 25% acetonitrile in aqueous buffer for 10 minutes followed by a linear increase to 70% acetonitrile over the next 10 minutes. After an additional 2 minutes at 70% acetonitrile, it was returned to 25% acetonitrile over the next 5 minutes. The flow rate was 1 ml/min. As can be seen in FIGS. 14A and 14B, the chimeras are capable of bioconversion of additional substrates.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A nucleic acid library of cytochrome P450 genes that encode proteins having a first set of intramolecular amino acid contacts, wherein said proteins are derived from:
   a first parental cytochrome P450 gene that encodes a parental protein having a second set of intramolecular amino acid contacts; and
   a second parental cytochrome P450 gene,
wherein less than 30 amino acid contacts differ between said first set and said second set of intramolecular amino acid contacts thereby providing genes that encode proteins with an E value of less than 30, and wherein said proteins encoded by the library of cytochrome P450 genes have enzymatic activity against a substrate, and wherein the P450 genes in the library are chimeric combinations of the first parental cytochrome P450 gene and the second parental cytochrome P450 gene, and wherein the encoded proteins have an average m value that is at least 22.

2. The library of claim 1, wherein said P450 genes encode proteins with an enzymatic activity against a first substrate, and wherein each of said first and second parental P450 genes encodes a parental protein with an enzymatic activity against a second substrate.

3. The library of claim 2, wherein said first and second substrates are the same substrate.

4. The library of claim 1, wherein the proteins encoded by said genes have an increase in enzymatic activity against said substrate compared to enzymatic activity of said parental cytochrome P450 protein.

5. The library of claim 1, wherein the proteins encoded by the library of cytochrome P450 genes have enzymatic activity against a third substrate, wherein said parental cytochrome P450 proteins do not have enzymatic activity against said third substrate.

6. The library of claim 5 wherein the proteins encoded by the library of cytochrome P450 genes differ from said parental cyctochrome P450 proteins by sixteen or more amino acids.

7. The library of claim 1, wherein said first parental cytochrome P450 gene and said second parental cytochrome P450 gene are at least 70% identical.

8. The library of claim 1, wherein said P450 genes are derived from cross-over events between said first parental cytochrome P450 gene and said second parental cytochrome P450 gene.

9. The library of claim 8, wherein said cross-over events result in at least one cytochrome P450 gene comprising at least 10 contiguous nucleotides from said first parental P450 gene.

10. The library of claim 8, wherein said cross-over events are selected from the group consisting of: 1, 2, 3, 4, 5, 6, 7, 8, 9, 10, 11, 12, 13, 14, and 15 cross-over events.

11. The library of claim 1, wherein said first set of intramolecular amino acid contacts is determined from the SCHEMA software program.

12. A nucleic acid library of cytochrome P450 genes that encode proteins having a first set of intramolecular amino acid contacts, wherein said proteins are derived from:
   a first parental cytochrome P450 gene that encodes a protein having a second set of intramolecular amino acid contacts; and
   a second parental cytochrome P450 gene,
wherein less than 30 intramolecular amino acid contacts are predicted to differ between said first set and said second set of intramolecular amino acid contacts thereby providing genes that encode proteins with an E value of less than 30, wherein said proteins encoded by the library of cytochrome P450 genes have enzymatic activity against a substrate, wherein the P450 genes in the library are chimeric combinations of the first parental cytochrome P450 gene and the second parental cytochrome P450 gene, and wherein said E value is defined by a SCHEMA algorithm, and wherein the encoded proteins have an average m value that is at least 22.

13. The library of claim 1, wherein the encoded protein has an m value that is at least 37.

14. The library of claim 1, wherein there are greater than 50 mutations on average in the encoded protein.

15. A nucleic acid library of cytochrome P450 genes that encode proteins having a first set of intramolecular amino acid contacts, wherein said proteins are derived from:
   a first parental cytochrome P450 gene that encodes a protein having a second set of intramolecular amino acid contacts; and
   a second parental cytochrome P450 gene,
wherein less than 30 intramolecular amino acid contacts are predicted to differ between said first set and said second set of intramolecular amino acid contacts thereby providing genes that encode proteins with an E value of less than 30, wherein said proteins encoded by the library of cytochrome P450 genes have enzymatic activity against a substrate, wherein the P450 genes in the library are chimeric combinations of the first parental cytochrome P450 gene and the second parental cytochrome P450 gene, wherein said E value is defined by a SCHEMA algorithm, and wherein the proteins encoded by the library of cytochrome P450 genes differ from said parental cyctochrome P450 proteins by an average of 22 or more amino acids.

* * * * *

UNITED STATES PATENT AND TRADEMARK OFFICE
CERTIFICATE OF CORRECTION

PATENT NO. : 8,603,949 B2  
APPLICATION NO. : 10/869813  
DATED : December 10, 2013  
INVENTOR(S) : Arnold et al.

Page 1 of 2

It is certified that error appears in the above-identified patent and that said Letters Patent is hereby corrected as shown below:

Title Page

In column 2 (page 1, item 56) at line 44, Under Other Publications, change "Comuunications," to --Communications,--.

In column 1 (page 2, item 56) at line 18, Under Other Publications, change ""Sterospecific" to --"Stereospecific--.

In column 1 (page 2, item 56) at line 19, Under Other Publications, change "speices,"" to --species,"--.

In column 2 (page 2, item 56) at line 4, Under Other Publications, change "extention,"" to --extension,"--.

In column 1 (page 3, item 56) at line 47, Under Other Publications, change "Benzycycloarene" to --Benzocycloarene--.

In column 2 (page 3, item 56) at line 16, Under Other Publications, change "Pressure-Indyced" to --Pressure-Induced--.

In column 2 (page 3, item 56) at line 47, Under Other Publications, change "Protoype" to --Prototype--.

In the Specification

In column 3 at line 38, Change "chimeras" to --chimeras.--.
In column 6 at line 19, Change "CYP102A2In" to --CYP102A2. In--.
In column 6 at line 20, Change "CYP102A 1" to --CYP102A1--.
In column 11 at line 1, Change "Optiniized" to --Optimized--.
In column 11 at line 29, Change "CYP102 μl," to --CYP102A1,--.
In column 11 at line 66, Change "beta-lactamses" to --beta-lactamases--.

Signed and Sealed this  
First Day of July, 2014

Michelle K. Lee  
*Deputy Director of the United States Patent and Trademark Office*

CERTIFICATE OF CORRECTION (continued)
U.S. Pat. No. 8,603,949 B2

In column 12 at line 21 (approx.), Change "CYP102A 1," to --CYP102A1,--.

In column 14 at line 54, Change "CYP102A 1" to --CYP102A1--.

In column 15 at line 1, Change "CYP102A 1" to --CYP102A1--.

In column 15 at line 62, Change "CYP102 μl," to --CYP102A1,--.

In column 16 at line 31 (approx.), Change "perioxidase" to --peroxidase--.

In column 16 at line 43, Change "CYP102 A1" to --CYP102A1--.

In column 17 at line 19, Change "CYP102 A1" to --CYP102A1--.

In column 17 at line 20, Change "library" to --library.--.

In column 20 at line 16, Change "CYP102 A1," to --CYP102A1,--.

In column 20 at line 41, Change "40fold" to --40 fold--.

In column 31 at line 56, Change "Half length" to --Half-length--.

In column 33 at line 51 (approx.), Change "GGA" to --GCA--.

In column 35 at line 22, Change "electophoresis." to --electrophoresis.--.

In columns 39-40 (TABLE 5) at line 14, Change "inbibitor)" to --inhibitor)--.

In column 39 at line 54 (approx.), Change "putatitive" to --putative--.

In the Claims

In column 145 at line 48 (approx.), In Claim 6, change "cyctochrome" to --cytochrome--.

In column 146 at line 39, In Claim 14, change "50mutations" to --50 mutations--.

In column 146 at line 58, In Claim 15, change "cyctochrome" to --cytochrome--.